(12) United States Patent
Harrison et al.

(10) Patent No.: US 6,967,100 B2
(45) Date of Patent: Nov. 22, 2005

(54) PANCREATIC ISLET CELL GROWTH FACTORS

(75) Inventors: Leonard C. Harrison, St Kilda West (AU); Fang-Xu Jiang, North Melbourne (AU); Edouard Guy Stanley, Ascot Vale (AU); Leonel Jorge Gonez, Chadstone (AU)

(73) Assignee: The Walter and Eliza Hall Institute of Medical Research, Victoria (AU)

( * ) Notice: Subject to any disclaimer, the term of this patent is extended or adjusted under 35 U.S.C. 154(b) by 278 days.

(21) Appl. No.: 09/784,911

(22) Filed: Feb. 16, 2001

(65) Prior Publication Data

US 2002/0072115 A1 Jun. 13, 2002

Related U.S. Application Data

(60) Provisional application No. 60/183,573, filed on Feb. 18, 2000.

(51) Int. Cl.$^7$ .............................. C12N 5/00; C12N 5/02
(52) U.S. Cl. ...................... 435/377; 435/375; 435/395; 435/398; 435/402
(58) Field of Search ................................ 435/375, 377, 435/395, 398, 402

(56) References Cited

U.S. PATENT DOCUMENTS 4,935,000 A * 6/1990 Dudek

OTHER PUBLICATIONS

Stem Cells: Scientific Progress and Future Research Directions. Department of Health and Human Services. Jun. 2001. http://www.nih.gov/news/stemcell/scireport.htm.*
Jiang et al. Bone morphogenetic proteins promote development of fetal pancreas epithelial colonies containing insulin-positive cells. J Cell Sci. Feb. 15, 2002;115(Pt 4):753–60.*
Kerr–Conte et al. Ductal cyst formation in collagen–embedded adult human islet preparations. A means to the reproduction of nesidioblastosis in vitro. Diabetes, Aug. 1996;45(8):1108–14.*
Bancroft J.D. et al., *Theory and Practice of Histological Techniques* (Churchill Livingstone, Edinburgh), 188–190.
Uehara Y. et al., "Phenotypic Change From Transformed To Normal Induced By Benzoquinonoid Ansamycins Accompanies Inactivation of p60$^{src}$ In Rat Kidney Cells Infected With Rous Sarcoma Virus", *Molecular and Cellular Biology* 6(6):2198–2206 (1986).
Bucci L.R. et al., "Isolation and Biochemical Studies Of Enriched Populations Of Spermatogonia And Early Primary Spermatocytes From Rat Testes", *Biology of Reproduction* 34:195–206 (1986).
Wozney J.M. et al., "Novel Regulators Of Bone Formation: Molecular Clones And Activities", *Science* 242:1528–1534 (1988).

McGuire P.G. et al., "The Interaction Of Plasminogen Activator With A Reconstituted Basement Membrane Matrix And Extracellular Macromolecules Produced By Cultured Epithelial Cells", *Journal of Cellular Biochemistry* 40:215–227 (1989).
Sonnenberg A. et al., "Integrin Recognition Of Different Cell–Binding Fragments Of Laminin (P1, E3, E8) And Evidence That $\alpha 6\beta 1$ But Not $\alpha 6\beta 4$ Functions As A Major Receptor For Fragment E8", *The Journal of Cell Biology* 110:2145–2155 (1990).
Ervasti J.M. et al., "A Role For The Dystrophin–Glycoprotein Complex As A Transmembrane Linker Between Laminin And Actin", *The Journal of Cell Biology* 122:809–822 (1993).
Vlahos C.J. et al., "A Specific Inhibitor Of Phosphatidylinositol 3–Kinase, 2–(4–Morpholinyl)–8–Phenyl–4H–1–Benzopyran–4–One (LY294002)", *The Journal of Biological Chemistry* 269(7):5241–5248 (1994).
Powis G. et al., "Wortmannin, A Potent And Selective Inhibitor Of Phosphatidylinositol–3–Kinase", *Cancer Research* 54:2419–2423 (1994).
Vukicevic S. et al., "Localization Of Osteogenic Protein–1 (Bone Morphogenetic Protein–7) During Human Embryonic Development: High Affinity Binding To Basement Membranes", *Biochemical and Biophysical Research Communications* 198(2): 693–700 (1994).
Jonsson J. et al., "Insulin–Promoter–Factor 1 Is Required For Pancreas Development In Mice", *Nature* 371:606–609 (1994).
Katagiri T. et al., "Bone Morphogenetic Protein–2 Converts The Differentiation Pathway Of C2C12 Myoblasts Into The Osteoblast Lineage", *The Journal of Cell Biology* 127(6):1755–1766 (1994).

(Continued)

*Primary Examiner*—Anne-Marie Falk
*Assistant Examiner*—Daniel M. Sullivan
(74) *Attorney, Agent, or Firm*—Scully, Scott, Murphy & Presser

(57) ABSTRACT

The present invention relates generally to growth factors and more particularly to growth factors which are capable of stimulating or otherwise facilitating formation of insulin-secreting cells. The identification of these growth factors permits the development of protocols to culture cells in vitro for transplantation into mammalian and in particular human subjects with insulin-dependent type 1 diabetes or related conditions. It is further contemplated that the endogenous expression of growth factors required for the development of insulin-producing cells may be manipulated in vivo, by the appropriate administration of agents including genetic agents capable of regulating the expression of growth factors in pancreatic duct epithelial cells. The growth factors ray also be administered to subjects with type 1 diabetes to stimulate the proliferation and differentiation of pancreatic cells into insulin-secreting cells. The present invention also provides modulators of growth factor-mediated pancreatic cell differentiation. Such modulators are useful in the treatment inter alia of $\beta$ cell tumors and/or pancreatic cancer.

12 Claims, 15 Drawing Sheets

OTHER PUBLICATIONS

Streuli C.H. et al., "Laminin Mediates Tissue–Specific Gene Expression In Mammary Epithelia", *The Journal of Cell Biology* 129:591–603 (1995).

Winnier G. et al., "Bone Morphogenetic Protein–4 Is Required For Mesoderm Formation And Patterning In The Mouse", *Genes & Development* 9:2105–2116 (1995).

Slack J.M.W., "Development Biology Of The Pancreas", *Development* 121:1569–1580 (1995).

Durbeej M. et al., "Non–Muscle α—Dystroglycan Is Involved In Epithelial Development", *The Journal of Cell Biology* 130(1):79–91 (1995).

Dudley D.T. et al., "A Synthetic Inhibitor Of The Mitogen–Activated Protein Kinase Cascade", *Proc. Natl. Acad. Sci. USA* 92:7686–7689 (1995).

Dudley A.T. et al., "A Requirement For Bone Morphogenetic Protein–7 During Development Of The Mammalian Kidney And Eye", *Genes and Development* 9:2795–2807 (1995).

Almeida E.A.C. et al., "Mouse Egg Integrin α6β1 Functions As A Sperm Receptor", *Cell* 81:1095–1104 (1995).

Lyons K.M. et al., "Colocalization of BMP 7 And BMP 2 RNAs Suggests That These Factors Cooperatively Mediate Tissue Interactions During Murine Development", *Mechanisms of Development* 50:71–83 (1995).

Luo G. et al., "BMP–7 Is An Inducer of Nephrogenesis, And Is Also Required For Eye Development And Skeletal Patterning", *Genes & Development* 9:2808–2820 (1995).

Aono A. et al., "Potent Ectopic Bone–Inducing Activity Of Bone Morphogenetic Protein–4/7 Heterodimer", *Biochemical & Biophysical Research Communication* 210(3):670–677 (1995).

Hogan B.LM., "Bone Morphogenetic Proteins In Development", *Current Opinion in Genetics & Development* 6:432–438 (1996).

Kerr–Conte J. et al., "Ductal Cyst Formation In Collagen–Embedded Adult Human Islet Preparations–A Means To The Reproduction Of Nesidioblastosis In Vitro", *Diabetes* 45:1108–1114 (1996).

Schuger L. et al., "Laminin And Heparan Sulfate Proteoglycan Mediate Epithelial Cell Polarization In Organotypic Cultures Of Embryonic Lung Cells: Evidence Implicating Involvement Of The Inner Globular Region Of Laminin β1 Chain And The Heparan Sulfate Groups Of Heparan Sulfate Proteoglycan", *Development Biology* 179:264–273 (1996).

Yuan S. et al., "Transdifferentiation Of Human Islets To Pancreatic Ductal Cells In Collagen Matrix Culture", *Differentiation* 61:67–75 (1996).

Zhang H. et al., "Mice Deficient For BMP2 Are Nonviable And Have Defects In Amnion/Chorion And Cardiac Development", *Development* 122:2977–2986 (1996).

Pall E.A. et al., "Differential Heparin Inhibition Of Skeletal Muscle α–Dystroglycan Binding To Laminins", *The Journal of Biological Chemistry* 271(7):3817–3821 (1996).

Offield M.F. et al., "PDX–1 Is Required For Pancreatic Outgrowth And Differentiation Of The Rostral Duodenum", *Development* 122:983–995 (1996).

Lelievre S. et al., "Extracellular Matrix Signaling From The Cellular Membrane Skeleton To The Nuclear Skeleton: A Model Of Gene Regulation", *Recent Progress in Hormone Research* 51:417–432 (1996).

Georges–Labouesse E. et al., "Absence Of Integrin α6 Leads To Epidermolysis Bullosa And Neonatal Death In Mice", *Nature Genetics* 13:370–373 (1996).

Gao Z–Y. et al., "Wortmannin Inhibits Insulin Secretion In Pancreatic Islets And β—TC3 Cells Independent Of Its Inhibition Of Phosphatidylinositol 3–Kinase", *Diabetes* 45:854–862 (1996).

Frade J.M. et al., "Laminin–1 Selectively Stimulates Neuron Generation From Cultured Retinal Neuroepithelial Cells", *Experimental Cell Research* 222:140–149 (1996).

Ekblom P., "Receptors For Laminins During Epithelial Morphogenesis", *Current Opinion in Cell Biology* 8:700–706 (1996).

Falk M. et al., "Integrin α 6Bβ1 Is Involved In Kidney Tubulogenesis In Vitro", *Journal of Cell Science* 109:2801–2810 (1996).

Bottinger E.P. et al., "Expression Of A Dominant–Negative Mutant TGF–β Type II Receptor In Transgenic Mice Reveals Essential Roles For TFG–β In Regulation Of Growth And Differentiation In The Exocrine Pancreas", *The EMBO Journal* 16(10):2621–2633 (1997).

Durbeej M. et al., "Dystroglycan In Development And Disease", *Current Opinion in Cell Biology* 10:594–601 (1998).

Hebrok M. et al., "Notochord Repression Of Endodermal Sonic Hedgehog Permits Pancreas Development", *Genes & Development* 12:1705–1713 (1998).

Chan Y–M. et al., "Molecular Organization Of Sarcoglycan Complex In Mouse Myotubes In Culture", *The Journal of Cell Biology* 143(7):2033–2044 (1998).

Yamaoka T. et al., "Hypoplasia of Pancreatic Islets In Transgenic Mice Expressing Activin Receptor Mutants", *J. Clin. Invest.* 102(2):294–301 (1998).

Brown S.C. et al., "Dystrophic Phenotype Induced In Vitro By Antibody Blockade Of Muscle α—Dystroglycan–Laminin Interaction", *Journal of Cell Science* 112:209–216 (1999).

Weaver M. et al., "Bmp Signaling Regulates Proximal–Distal Differentiation Of Endoderm In Mouse Lung Development", *Development* 126:4005–4015 (1999).

Bonner–Weir S. et al., "In Vitro Cultivation Of Human Islets From Expanded Ductal Tissue", *PNAS* 97(14):7999–8004 (2000).

\* cited by examiner

SEQUENCE LISTING

```
<160> NUMBER OF SEQ ID NOS: 30

<210> SEQ ID NO 1
<211> LENGTH: 1260
<212> TYPE: DNA
<213> ORGANISM: mouse
<220> FEATURE:
<221> NAME/KEY: CDS
<222> LOCATION: (1)..(1260)
<221> NAME/KEY: UNSURE
<222> LOCATION: (186)
<223> OTHER INFORMATION: Xaa at position 186 is Tyr or His

<400> SEQUENCE: 1 atg gcg cgc ctg atg att cct ggt aac cga atg ctg atg gtc gtt tta        48
Met Ala Arg Leu Met Ile Pro Gly Asn Arg Met Leu Met Val Val Leu
1               5                   10                  15 tta tgc caa gtc ctg cta gga ggc gcg agc cat gct agt ttg ata cct        96
Leu Cys Gln Val Leu Leu Gly Gly Ala Ser His Ala Ser Leu Ile Pro
            20                  25                  30 gag acc ggg aag aaa aaa gtc gcc gag att cag ggc cac gcg gga gga       144
Glu Thr Gly Lys Lys Lys Val Ala Glu Ile Gln Gly His Ala Gly Gly
        35                  40                  45 cgc cgc tca ggg cag agc cat gag ctc ctg cgg gac ttc gag gcg aca       192
Arg Arg Ser Gly Gln Ser His Glu Leu Leu Arg Asp Phe Glu Ala Thr
    50                  55                  60 ctt cta cag atg ttt ggg ctg cgc cgc cgt ccg cag cct agc aag agc       240
Leu Leu Gln Met Phe Gly Leu Arg Arg Arg Pro Gln Pro Ser Lys Ser
65                  70                  75                  80 gcc gtc att ccg gat tac atg agg gat ctt tac cgg ctc cag tct ggg       288
Ala Val Ile Pro Asp Tyr Met Arg Asp Leu Tyr Arg Leu Gln Ser Gly
                85                  90                  95 gag gag gag gag gaa gag cag agc cag gga acc ggg ctt gag tac ccg       336
Glu Glu Glu Glu Glu Glu Gln Ser Gln Gly Thr Gly Leu Glu Tyr Pro
            100                 105                 110 gag cgt ccc gcc agc cga gcc aac act gtg agg agt ttc cat cac gaa       384
Glu Arg Pro Ala Ser Arg Ala Asn Thr Val Arg Ser Phe His His Glu
        115                 120                 125 gaa cat ctg gag aac atc cca ggg acc agt gag agc tct gct ttt cgt       432
Glu His Leu Glu Asn Ile Pro Gly Thr Ser Glu Ser Ser Ala Phe Arg
    130                 135                 140 ttc ctc ttc aac ctc agc agc atc cca gaa aat gag gtg atc tcc tcg       480
Phe Leu Phe Asn Leu Ser Ser Ile Pro Glu Asn Glu Val Ile Ser Ser
145                 150                 155                 160 gca gag ctc cgg ctc ttt cgg gag cag gtg gac cag ggc cct gac tgg       528
```

-continued

```
        Ala Glu Leu Arg Leu Phe Arg Glu Gln Val Asp Gln Gly Pro Asp Trp
                        165                 170                 175 gaa cag ggc ttc cac cgt ata aac att yat gag gtt atg aag ccc cca           576
Glu Gln Gly Phe His Arg Ile Asn Ile Xaa Glu Val Met Lys Pro Pro
                180                 185                 190 gca gaa atg gtt cct gga cac ctc atc aca cga cta ctg gac acc aga           624
Ala Glu Met Val Pro Gly His Leu Ile Thr Arg Leu Leu Asp Thr Arg
            195                 200                 205 cta gtc cat cac aat gtg aca cgg tgg gaa act ttc gat gtg agc cct           672
Leu Val His His Asn Val Thr Arg Trp Glu Thr Phe Asp Val Ser Pro
        210                 215                 220 gca gtc ctt cgc tgg acc cgg gaa aag caa ccc aat tat ggg ctg gcc           720
Ala Val Leu Arg Trp Thr Arg Glu Lys Gln Pro Asn Tyr Gly Leu Ala
225                 230                 235                 240 att gag gtg act cac ctc cac cag aca cgg acc cac cag ggc cag cat           768
Ile Glu Val Thr His Leu His Gln Thr Arg Thr His Gln Gly Gln His
                245                 250                 255 gtc aga atc agc cga tcg tta cct caa ggg agt gga gat tgg gcc caa           816
Val Arg Ile Ser Arg Ser Leu Pro Gln Gly Ser Gly Asp Trp Ala Gln
            260                 265                 270 ctc cgg ccc ctc ctg gtc act ttt ggc cat gat ggc cgg ggc cat acc           864
Leu Arg Pro Leu Leu Val Thr Phe Gly His Asp Gly Arg Gly His Thr
        275                 280                 285 ttg acc cgc agg agg gcc aaa cgt agt ccc aag acg cgc cag gag gag           912
Leu Thr Arg Arg Arg Ala Lys Arg Ser Pro Lys Thr Arg Gln Glu Glu
    290                 295                 300 gaa tac atg ccc atg gag acg cgt agg aag aag aat aag aac tgc cgt           960
Glu Tyr Met Pro Met Glu Thr Arg Arg Lys Lys Asn Lys Asn Cys Arg
305                 310                 315                 320 cgc cat tca cta tac gtg gac ttc agt gac gtg ggc tgg aat gat tgg          1008
Arg His Ser Leu Tyr Val Asp Phe Ser Asp Val Gly Trp Asn Asp Trp
                325                 330                 335 att gtg gcc cca ccc ggc tac cag gcc ttc tac tgc cat ggg gac tgt          1056
Ile Val Ala Pro Pro Gly Tyr Gln Ala Phe Tyr Cys His Gly Asp Cys
            340                 345                 350 ccc ttt cca ctg gct gat cac ctc aac tca acc aac cat gcc att gtg          1104
Pro Phe Pro Leu Ala Asp His Leu Asn Ser Thr Asn His Ala Ile Val
        355                 360                 365 cag acc cta gtc aac tct gtt aat tct agt atc cct aag gcc tgt tgt          1152
Gln Thr Leu Val Asn Ser Val Asn Ser Ser Ile Pro Lys Ala Cys Cys
    370                 375                 380 gtc ccc act gaa ctg agt gcc att tcc atg ttg tac ctg gat gag tat          1200
Val Pro Thr Glu Leu Ser Ala Ile Ser Met Leu Tyr Leu Asp Glu Tyr
385                 390                 395                 400 gac aag gtg gtg ttg aaa aat tat cag gag atg gtg gta gag ggg tgt          1248
Asp Lys Val Val Leu Lys Asn Tyr Gln Glu Met Val Val Glu Gly Cys
                405                 410                 415 gga tgc cgc tga                                                          1260
Gly Cys Arg
```

<210> SEQ ID NO 2
<211> LENGTH: 419
<212> TYPE: PRT
<213> ORGANISM: mouse
<220> FEATURE:
<221> NAME/KEY: UNSURE
<222> LOCATION: (186)
<223> OTHER INFORMATION: Xaa at position 186 is Tyr or His

<400> SEQUENCE: 2

Met Ala Arg Leu Met Ile Pro Gly Asn Arg Met Leu Met Val Val Leu

-continued

```
1               5                    10                   15
Leu Cys Gln Val Leu Gly Gly Ala Ser His Ala Ser Leu Ile Pro
                20                  25                  30
Glu Thr Gly Lys Lys Val Ala Glu Ile Gln Gly His Ala Gly Gly
            35                  40              45
Arg Arg Ser Gly Gln Ser His Glu Leu Leu Arg Asp Phe Glu Ala Thr
    50              55              60
Leu Leu Gln Met Phe Gly Leu Arg Arg Arg Pro Gln Pro Ser Lys Ser
65              70              75              80
Ala Val Ile Pro Asp Tyr Met Arg Asp Leu Tyr Arg Leu Gln Ser Gly
                85                  90              95
Glu Glu Glu Glu Glu Glu Gln Ser Gln Gly Thr Gly Leu Glu Tyr Pro
                100                 105                 110
Glu Arg Pro Ala Ser Arg Ala Asn Thr Val Arg Ser Phe His His Glu
            115                 120             125
Glu His Leu Glu Asn Ile Pro Gly Thr Ser Glu Ser Ser Ala Phe Arg
    130             135             140
Phe Leu Phe Asn Leu Ser Ser Ile Pro Glu Asn Glu Val Ile Ser Ser
145             150             155             160
Ala Glu Leu Arg Leu Phe Arg Glu Gln Val Asp Gln Gly Pro Asp Trp
                165                 170                 175
Glu Gln Gly Phe His Arg Ile Asn Ile Xaa Glu Val Met Lys Pro Pro
                180                 185             190
Ala Glu Met Val Pro Gly His Leu Ile Thr Arg Leu Leu Asp Thr Arg
        195             200             205
Leu Val His His Asn Val Thr Arg Trp Glu Thr Phe Asp Val Ser Pro
    210             215             220
Ala Val Leu Arg Trp Thr Arg Glu Lys Gln Pro Asn Tyr Gly Leu Ala
225             230             235             240
Ile Glu Val Thr His Leu His Gln Thr Arg Thr His Gln Gly Gln His
                245                 250                 255
Val Arg Ile Ser Arg Ser Leu Pro Gln Gly Ser Gly Asp Trp Ala Gln
            260                 265             270
Leu Arg Pro Leu Leu Val Thr Phe Gly His Asp Gly Arg Gly His Thr
    275             280             285
Leu Thr Arg Arg Arg Ala Lys Arg Ser Pro Lys Thr Arg Gln Glu Glu
    290             295             300
Glu Tyr Met Pro Met Glu Thr Arg Lys Lys Asn Lys Asn Cys Arg
305             310             315             320
Arg His Ser Leu Tyr Val Asp Phe Ser Asp Val Gly Trp Asn Asp Trp
                325                 330                 335
Ile Val Ala Pro Pro Gly Tyr Gln Ala Phe Tyr Cys His Gly Asp Cys
                340                 345             350
Pro Phe Pro Leu Ala Asp His Leu Asn Ser Thr Asn His Ala Ile Val
        355                 360             365
Gln Thr Leu Val Asn Ser Val Asn Ser Ser Ile Pro Lys Ala Cys Cys
    370             375             380
Val Pro Thr Glu Leu Ser Ala Ile Ser Met Leu Tyr Leu Asp Glu Tyr
385             390             395             400
Asp Lys Val Val Leu Lys Asn Tyr Gln Glu Met Val Val Glu Gly Cys
            405             410             415
Gly Cys Arg
```

```
<210> SEQ ID NO 3
<211> LENGTH: 1362
<212> TYPE: DNA
<213> ORGANISM: mouse
<220> FEATURE:
<221> NAME/KEY: CDS
<222> LOCATION: (1)..(1311)
<221> NAME/KEY: UNSURE
<222> LOCATION: (186)
<223> OTHER INFORMATION: Xaa at position 186 is Tyr or His

<400> SEQUENCE: 3
```

| | | | | | | | | | | | | | | | | |
|---|---|---|---|---|---|---|---|---|---|---|---|---|---|---|---|---|
| atg | gcg | cgc | ctg | atg | att | cct | ggt | aac | cga | atg | ctg | atg | gtc | gtt | tta | 48 |
| Met | Ala | Arg | Leu | Met | Ile | Pro | Gly | Asn | Arg | Met | Leu | Met | Val | Val | Leu | |
| 1 | | | | 5 | | | | | 10 | | | | | 15 | | |
| tta | tgc | caa | gtc | ctg | cta | gga | ggc | gcg | agc | cat | gct | agt | ttg | ata | cct | 96 |
| Leu | Cys | Gln | Val | Leu | Leu | Gly | Gly | Ala | Ser | His | Ala | Ser | Leu | Ile | Pro | |
| | | | 20 | | | | | 25 | | | | | 30 | | | |
| gag | acc | ggg | aag | aaa | aaa | gtc | gcc | gag | att | cag | ggc | cac | gcg | gga | gga | 144 |
| Glu | Thr | Gly | Lys | Lys | Lys | Val | Ala | Glu | Ile | Gln | Gly | His | Ala | Gly | Gly | |
| | | 35 | | | | | 40 | | | | | 45 | | | | |
| cgc | cgc | tca | ggg | cag | agc | cat | gag | ctc | ctg | cgg | gac | ttc | gag | gcg | aca | 192 |
| Arg | Arg | Ser | Gly | Gln | Ser | His | Glu | Leu | Leu | Arg | Asp | Phe | Glu | Ala | Thr | |
| | 50 | | | | | 55 | | | | | 60 | | | | | |
| ctt | cta | cag | atg | ttt | ggg | ctg | cgc | cgc | cgt | ccg | cag | cct | agc | aag | agc | 240 |
| Leu | Leu | Gln | Met | Phe | Gly | Leu | Arg | Arg | Arg | Pro | Gln | Pro | Ser | Lys | Ser | |
| 65 | | | | | 70 | | | | | 75 | | | | | 80 | |
| gcc | gtc | att | ccg | gat | tac | atg | agg | gat | ctt | tac | cgg | ctc | cag | tct | ggg | 288 |
| Ala | Val | Ile | Pro | Asp | Tyr | Met | Arg | Asp | Leu | Tyr | Arg | Leu | Gln | Ser | Gly | |
| | | | | 85 | | | | | 90 | | | | | 95 | | |
| gag | gag | gag | gag | gaa | gag | cag | agc | cag | gga | acc | ggg | ctt | gag | tac | ccg | 336 |
| Glu | Glu | Glu | Glu | Glu | Glu | Gln | Ser | Gln | Gly | Thr | Gly | Leu | Glu | Tyr | Pro | |
| | | | 100 | | | | | 105 | | | | | 110 | | | |
| gag | cgt | ccc | gcc | agc | cga | gcc | aac | act | gtg | agg | agt | ttc | cat | cac | gaa | 384 |
| Glu | Arg | Pro | Ala | Ser | Arg | Ala | Asn | Thr | Val | Arg | Ser | Phe | His | His | Glu | |
| | | 115 | | | | | 120 | | | | | 125 | | | | |
| gaa | cat | ctg | gag | aac | atc | cca | ggg | acc | agt | gag | agc | tct | gct | ttt | cgt | 432 |
| Glu | His | Leu | Glu | Asn | Ile | Pro | Gly | Thr | Ser | Glu | Ser | Ser | Ala | Phe | Arg | |
| | 130 | | | | | 135 | | | | | 140 | | | | | |
| ttc | ctc | ttc | aac | ctc | agc | agc | atc | cca | gaa | aat | gag | gtg | atc | tcc | tcg | 480 |
| Phe | Leu | Phe | Asn | Leu | Ser | Ser | Ile | Pro | Glu | Asn | Glu | Val | Ile | Ser | Ser | |
| 145 | | | | | 150 | | | | | 155 | | | | | 160 | |
| gca | gag | ctc | cgg | ctc | ttt | cgg | gag | cag | gtg | gac | cag | ggc | cct | gac | tgg | 528 |
| Ala | Glu | Leu | Arg | Leu | Phe | Arg | Glu | Gln | Val | Asp | Gln | Gly | Pro | Asp | Trp | |
| | | | | 165 | | | | | 170 | | | | | 175 | | |
| gaa | cag | ggc | ttc | cac | cgt | ata | aac | att | yat | gag | gtt | atg | aag | ccc | cca | 576 |
| Glu | Gln | Gly | Phe | His | Arg | Ile | Asn | Ile | Xaa | Glu | Val | Met | Lys | Pro | Pro | |
| | | | 180 | | | | | 185 | | | | | 190 | | | |
| gca | gaa | atg | gtt | cct | gga | cac | ctc | atc | aca | cga | cta | ctg | gac | acc | aga | 624 |
| Ala | Glu | Met | Val | Pro | Gly | His | Leu | Ile | Thr | Arg | Leu | Leu | Asp | Thr | Arg | |
| | | 195 | | | | | 200 | | | | | 205 | | | | |
| cta | gtc | cat | cac | aat | gtg | aca | cgg | tgg | gaa | act | ttc | gat | gtg | agc | cct | 672 |
| Leu | Val | His | His | Asn | Val | Thr | Arg | Trp | Glu | Thr | Phe | Asp | Val | Ser | Pro | |
| | 210 | | | | | 215 | | | | | 220 | | | | | |
| gca | gtc | ctt | cgc | tgg | acc | cgg | gaa | aag | caa | ccc | aat | tat | ggg | ctg | gcc | 720 |
| Ala | Val | Leu | Arg | Trp | Thr | Arg | Glu | Lys | Gln | Pro | Asn | Tyr | Gly | Leu | Ala | |
| 225 | | | | | 230 | | | | | 235 | | | | | 240 | |
| att | gag | gtg | act | cac | ctc | cac | cag | aca | cgg | acc | cac | cag | ggc | cag | cat | 768 |
| Ile | Glu | Val | Thr | His | Leu | His | Gln | Thr | Arg | Thr | His | Gln | Gly | Gln | His | |
| | | | | 245 | | | | | 250 | | | | | 255 | | |
| gtc | aga | atc | agc | cga | tcg | tta | cct | caa | ggg | agt | gga | gat | tgg | gcc | caa | 816 |

-continued

```
Val Arg Ile Ser Arg Ser Leu Pro Gln Gly Ser Gly Asp Trp Ala Gln
            260                 265                 270 ctc cgg ccc ctc ctg gtc act ttt ggc cat gat ggc cgg ggc cat acc      864
Leu Arg Pro Leu Leu Val Thr Phe Gly His Asp Gly Arg Gly His Thr
            275                 280                 285 ttg acc cgc agg agg gcc aaa cgt agt ccc aag acg cgc cag gag gag      912
Leu Thr Arg Arg Arg Ala Lys Arg Ser Pro Lys Thr Arg Gln Glu Glu
        290                 295                 300 gaa tac atg ccc atg gag acg cgt acc cag tcg cag gac gtg tcc cgg      960
Glu Tyr Met Pro Met Glu Thr Arg Thr Gln Ser Gln Asp Val Ser Arg
305                 310                 315                 320 ggc tcc ggt tct tca gac tac aac ggc agt gag tta aaa aca gct tgc     1008
Gly Ser Gly Ser Ser Asp Tyr Asn Gly Ser Glu Leu Lys Thr Ala Cys
                325                 330                 335 aag aag cat gag ctc tat gtg agc ttc cag gac ctg gga tgg cag gac     1056
Lys Lys His Glu Leu Tyr Val Ser Phe Gln Asp Leu Gly Trp Gln Asp
            340                 345                 350 tgg atc att gca ccc aaa ggc tac gct gcc aac tac tgt gat gga gag     1104
Trp Ile Ile Ala Pro Lys Gly Tyr Ala Ala Asn Tyr Cys Asp Gly Glu
            355                 360                 365 tgt tcc ttc cca ctc aac gca cac atg aat gcc acc aac cac gcc att     1152
Cys Ser Phe Pro Leu Asn Ala His Met Asn Ala Thr Asn His Ala Ile
        370                 375                 380 gta cag acc ttg gtc cac ctt atg aat ccc gag tac gtc ccc aaa cca     1200
Val Gln Thr Leu Val His Leu Met Asn Pro Glu Tyr Val Pro Lys Pro
385                 390                 395                 400 tgc tgc gca cca acc aaa ctg aat gcc atc tcg gtt ctt tac ttc gat     1248
Cys Cys Ala Pro Thr Lys Leu Asn Ala Ile Ser Val Leu Tyr Phe Asp
                405                 410                 415 gat aac tcc aat gtc atc ttg aaa aag tac agg aat atg gtc gtg aga     1296
Asp Asn Ser Asn Val Ile Leu Lys Lys Tyr Arg Asn Met Val Val Arg
            420                 425                 430 gct tgt ggt tgc cat taagttgaag ctggtgtgtg tgtgtgggtg ggggcatggt     1351
Ala Cys Gly Cys His
            435 tctgccttgg a                                                         1362

<210> SEQ ID NO 4
<211> LENGTH: 437
<212> TYPE: PRT
<213> ORGANISM: mouse
<220> FEATURE:
<221> NAME/KEY: UNSURE
<222> LOCATION: (186)
<223> OTHER INFORMATION: Xaa at position 186 is Tyr or His

<400> SEQUENCE: 4

Met Ala Arg Leu Met Ile Pro Gly Asn Arg Met Leu Met Val Val Leu
1               5                  10                  15

Leu Cys Gln Val Leu Leu Gly Gly Ala Ser His Ala Ser Leu Ile Pro
                20                  25                  30

Glu Thr Gly Lys Lys Lys Val Ala Glu Ile Gln Gly His Ala Gly Gly
            35                  40                  45

Arg Arg Ser Gly Gln Ser His Glu Leu Leu Arg Asp Phe Glu Ala Thr
        50                  55                  60

Leu Leu Gln Met Phe Gly Leu Arg Arg Arg Pro Gln Pro Ser Lys Ser
65                  70                  75                  80

Ala Val Ile Pro Asp Tyr Met Arg Asp Leu Tyr Arg Leu Gln Ser Gly
                85                  90                  95
```

```
Glu Glu Glu Glu Glu Glu Gln Ser Gln Gly Thr Gly Leu Glu Tyr Pro
            100                 105                 110

Glu Arg Pro Ala Ser Arg Ala Asn Thr Val Arg Ser Phe His His Glu
        115                 120                 125

Glu His Leu Glu Asn Ile Pro Gly Thr Ser Glu Ser Ser Ala Phe Arg
    130                 135                 140

Phe Leu Phe Asn Leu Ser Ser Ile Pro Glu Asn Glu Val Ile Ser Ser
145                 150                 155                 160

Ala Glu Leu Arg Leu Phe Arg Glu Gln Val Asp Gln Gly Pro Asp Trp
                165                 170                 175

Glu Gln Gly Phe His Arg Ile Asn Ile Xaa Glu Val Met Lys Pro Pro
            180                 185                 190

Ala Glu Met Val Pro Gly His Leu Ile Thr Arg Leu Leu Asp Thr Arg
        195                 200                 205

Leu Val His His Asn Val Thr Arg Trp Glu Thr Phe Asp Val Ser Pro
    210                 215                 220

Ala Val Leu Arg Trp Thr Arg Glu Lys Gln Pro Asn Tyr Gly Leu Ala
225                 230                 235                 240

Ile Glu Val Thr His Leu His Gln Thr Arg Thr His Gln Gly Gln His
                245                 250                 255

Val Arg Ile Ser Arg Ser Leu Pro Gln Gly Ser Gly Asp Trp Ala Gln
            260                 265                 270

Leu Arg Pro Leu Leu Val Thr Phe Gly His Asp Gly Arg Gly His Thr
        275                 280                 285

Leu Thr Arg Arg Arg Ala Lys Arg Ser Pro Lys Thr Arg Gln Glu Glu
    290                 295                 300

Glu Tyr Met Pro Met Glu Thr Arg Thr Gln Ser Gln Asp Val Ser Arg
305                 310                 315                 320

Gly Ser Gly Ser Ser Asp Tyr Asn Gly Ser Glu Leu Lys Thr Ala Cys
                325                 330                 335

Lys Lys His Glu Leu Tyr Val Ser Phe Gln Asp Leu Gly Trp Gln Asp
            340                 345                 350

Trp Ile Ile Ala Pro Lys Gly Tyr Ala Ala Asn Tyr Cys Asp Gly Glu
        355                 360                 365

Cys Ser Phe Pro Leu Asn Ala His Met Asn Ala Thr Asn His Ala Ile
    370                 375                 380

Val Gln Thr Leu Val His Leu Met Asn Pro Glu Tyr Val Pro Lys Pro
385                 390                 395                 400

Cys Cys Ala Pro Thr Lys Leu Asn Ala Ile Ser Val Leu Tyr Phe Asp
                405                 410                 415

Asp Asn Ser Asn Val Ile Leu Lys Lys Tyr Arg Asn Met Val Val Arg
            420                 425                 430

Ala Cys Gly Cys His
        435

<210> SEQ ID NO 5
<211> LENGTH: 1289
<212> TYPE: DNA
<213> ORGANISM: mouse
<220> FEATURE:
<221> NAME/KEY: CDS
<222> LOCATION: (1)..(1281)
<221> NAME/KEY: UNSURE
<222> LOCATION: (186)
<223> OTHER INFORMATION: Xaa at position 186 is Tyr or His

<400> SEQUENCE: 5
```

```
atg gcg cgc ctg atg att cct ggt aac cga atg ctg atg gtc gtt tta     48
Met Ala Arg Leu Met Ile Pro Gly Asn Arg Met Leu Met Val Val Leu
1               5                  10                  15 tta tgc caa gtc ctg cta gga ggc gcg agc cat gct agt ttg ata cct     96
Leu Cys Gln Val Leu Leu Gly Gly Ala Ser His Ala Ser Leu Ile Pro
            20                  25                  30 gag acc ggg aag aaa aaa gtc gcc gag att cag ggc cac gcg gga gga    144
Glu Thr Gly Lys Lys Lys Val Ala Glu Ile Gln Gly His Ala Gly Gly
        35                  40                  45 cgc cgc tca ggg cag agc cat gag ctc ctg cgg gac ttc gag gcg aca    192
Arg Arg Ser Gly Gln Ser His Glu Leu Leu Arg Asp Phe Glu Ala Thr
50                  55                  60 ctt cta cag atg ttt ggg ctg cgc cgc cgt ccg cag cct agc aag agc    240
Leu Leu Gln Met Phe Gly Leu Arg Arg Arg Pro Gln Pro Ser Lys Ser
65                  70                  75                  80 gcc gtc att ccg gat tac atg agg gat ctt tac cgg ctc cag tct ggg    288
Ala Val Ile Pro Asp Tyr Met Arg Asp Leu Tyr Arg Leu Gln Ser Gly
                85                  90                  95 gag gag gag gag gaa gag cag agc cag gga acc ggg ctt gag tac ccg    336
Glu Glu Glu Glu Glu Glu Gln Ser Gln Gly Thr Gly Leu Glu Tyr Pro
            100                 105                 110 gag cgt ccc gcc agc cga gcc aac act gtg agg agt ttc cat cac gaa    384
Glu Arg Pro Ala Ser Arg Ala Asn Thr Val Arg Ser Phe His His Glu
        115                 120                 125 gaa cat ctg gag aac atc cca ggg acc agt gag agc tct gct ttt cgt    432
Glu His Leu Glu Asn Ile Pro Gly Thr Ser Glu Ser Ser Ala Phe Arg
130                 135                 140 ttc ctc ttc aac ctc agc agc atc cca gaa aat gag gtg atc tcc tcg    480
Phe Leu Phe Asn Leu Ser Ser Ile Pro Glu Asn Glu Val Ile Ser Ser
145                 150                 155                 160 gca gag ctc cgg ctc ttt cgg gag cag gtg gac cag ggc cct gac tgg    528
Ala Glu Leu Arg Leu Phe Arg Glu Gln Val Asp Gln Gly Pro Asp Trp
                165                 170                 175 gaa cag ggc ttc cac cgt ata aac att yat gag gtt atg aag ccc cca    576
Glu Gln Gly Phe His Arg Ile Asn Ile Xaa Glu Val Met Lys Pro Pro
            180                 185                 190 gca gaa atg gtt cct gga cac ctc atc aca cga cta ctg gac acc aga    624
Ala Glu Met Val Pro Gly His Leu Ile Thr Arg Leu Leu Asp Thr Arg
        195                 200                 205 cta gtc cat cac aat gtg aca cgg tgg gaa act ttc gat gtg agc cct    672
Leu Val His His Asn Val Thr Arg Trp Glu Thr Phe Asp Val Ser Pro
210                 215                 220 gca gtc ctt cgc tgg acc cgg gaa aag caa ccc aat tat ggg ctg gcc    720
Ala Val Leu Arg Trp Thr Arg Glu Lys Gln Pro Asn Tyr Gly Leu Ala
225                 230                 235                 240 att gag gtg act cac ctc cac cag aca cgg acc cac cag ggc cag cat    768
Ile Glu Val Thr His Leu His Gln Thr Arg Thr His Gln Gly Gln His
                245                 250                 255 gtc aga atc agc cga tcg tta cct caa ggg agt gga gat tgg gcc caa    816
Val Arg Ile Ser Arg Ser Leu Pro Gln Gly Ser Gly Asp Trp Ala Gln
            260                 265                 270 ctc cgg ccc ctc ctg gtc act ttt ggc cat gat ggc cgg ggc cat acc    864
Leu Arg Pro Leu Leu Val Thr Phe Gly His Asp Gly Arg Gly His Thr
        275                 280                 285 ttg acc cgc agg agg gcc aaa cgt agt ccc aag cat cac cca cag cgg    912
Leu Thr Arg Arg Arg Ala Lys Arg Ser Pro Lys His His Pro Gln Arg
290                 295                 300 tcc acg cgc cag gag cag aag ctt atc tcg gag gag gac ctg acg cgt    960
Ser Thr Arg Gln Glu Gln Lys Leu Ile Ser Glu Glu Asp Leu Thr Arg
```

-continued

```
           305                 310                 315                 320
agg aag aag aat aag aac tgc cgt cgc cat tca cta tac gtg gac ttc      1008
Arg Lys Lys Asn Lys Asn Cys Arg Arg His Ser Leu Tyr Val Asp Phe
                325                 330                 335 agt gac gtg ggc tgg aat gat tgg att gtg gcc cca ccc ggc tac cag      1056
Ser Asp Val Gly Trp Asn Asp Trp Ile Val Ala Pro Pro Gly Tyr Gln
    340                 345                 350 gcc ttc tac tgc cat ggg gac tgt ccc ttt cca ctg gct gat cac ctc      1104
Ala Phe Tyr Cys His Gly Asp Cys Pro Phe Pro Leu Ala Asp His Leu
355                 360                 365 aac tca acc aac cat gcc att gtg cag acc cta gtc aac tct gtt aat      1152
Asn Ser Thr Asn His Ala Ile Val Gln Thr Leu Val Asn Ser Val Asn
        370                 375                 380 tct agt atc cct aag gcc tgt tgt gtc ccc act gaa ctg agt gcc att      1200
Ser Ser Ile Pro Lys Ala Cys Cys Val Pro Thr Glu Leu Ser Ala Ile
385                 390                 395                 400 tcc atg ttg tac ctg gat gag tat gac aag gtg gtg ttg aaa aat tat      1248
Ser Met Leu Tyr Leu Asp Glu Tyr Asp Lys Val Val Leu Lys Asn Tyr
                405                 410                 415 cag gag atg gtg gta gag ggg tgt gga tgc cgc tgacgcgt                 1289
Gln Glu Met Val Val Glu Gly Cys Gly Cys Arg
            420                 425
```

<210> SEQ ID NO 6
<211> LENGTH: 427
<212> TYPE: PRT
<213> ORGANISM: mouse
<220> FEATURE:
<221> NAME/KEY: UNSURE
<222> LOCATION: (186)
<223> OTHER INFORMATION: Xaa at position 186 is Tyr or His

<400> SEQUENCE: 6

```
Met Ala Arg Leu Met Ile Pro Gly Asn Arg Met Leu Met Val Val Leu
1               5                   10                  15

Leu Cys Gln Val Leu Leu Gly Gly Ala Ser His Ala Ser Leu Ile Pro
            20                  25                  30

Glu Thr Gly Lys Lys Val Ala Glu Ile Gln Gly His Ala Gly Gly
        35                  40                  45

Arg Arg Ser Gly Gln Ser His Glu Leu Leu Arg Asp Phe Glu Ala Thr
    50                  55                  60

Leu Leu Gln Met Phe Gly Leu Arg Arg Arg Pro Gln Pro Ser Lys Ser
65                  70                  75                  80

Ala Val Ile Pro Asp Tyr Met Arg Asp Leu Tyr Arg Leu Gln Ser Gly
                85                  90                  95

Glu Glu Glu Glu Glu Gln Ser Gln Gly Thr Gly Leu Glu Tyr Pro
            100                 105                 110

Glu Arg Pro Ala Ser Arg Ala Asn Thr Val Arg Ser Phe His His Glu
        115                 120                 125

Glu His Leu Glu Asn Ile Pro Gly Thr Ser Glu Ser Ser Ala Phe Arg
    130                 135                 140

Phe Leu Phe Asn Leu Ser Ser Ile Pro Glu Asn Glu Val Ile Ser Ser
145                 150                 155                 160

Ala Glu Leu Arg Leu Phe Arg Glu Gln Val Asp Gln Gly Pro Asp Trp
                165                 170                 175

Glu Gln Gly Phe His Arg Ile Asn Ile Xaa Glu Val Met Lys Pro Pro
            180                 185                 190

Ala Glu Met Val Pro Gly His Leu Ile Thr Arg Leu Leu Asp Thr Arg
```

-continued

```
                    195                 200                 205
Leu Val His His Asn Val Thr Arg Trp Glu Thr Phe Asp Val Ser Pro
    210                 215                 220

Ala Val Leu Arg Trp Thr Arg Glu Lys Gln Pro Asn Tyr Gly Leu Ala
225                 230                 235                 240

Ile Glu Val Thr His Leu His Gln Thr Arg Thr His Gln Gly Gln His
                245                 250                 255

Val Arg Ile Ser Arg Ser Leu Pro Gln Gly Ser Gly Asp Trp Ala Gln
            260                 265                 270

Leu Arg Pro Leu Leu Val Thr Phe Gly His Asp Gly Arg Gly His Thr
        275                 280                 285

Leu Thr Arg Arg Arg Ala Lys Arg Ser Pro Lys His His Pro Gln Arg
    290                 295                 300

Ser Thr Arg Gln Glu Gln Lys Leu Ile Ser Glu Asp Leu Thr Arg
305                 310                 315                 320

Arg Lys Lys Asn Lys Asn Cys Arg Arg His Ser Leu Tyr Val Asp Phe
                325                 330                 335

Ser Asp Val Gly Trp Asn Asp Trp Ile Val Ala Pro Pro Gly Tyr Gln
            340                 345                 350

Ala Phe Tyr Cys His Gly Asp Cys Pro Phe Pro Leu Ala Asp His Leu
        355                 360                 365

Asn Ser Thr Asn His Ala Ile Val Gln Thr Leu Val Asn Ser Val Asn
    370                 375                 380

Ser Ser Ile Pro Lys Ala Cys Cys Val Pro Thr Glu Leu Ser Ala Ile
385                 390                 395                 400

Ser Met Leu Tyr Leu Asp Glu Tyr Asp Lys Val Val Leu Lys Asn Tyr
                405                 410                 415

Gln Glu Met Val Val Glu Gly Cys Gly Cys Arg
            420                 425
```

```
<210> SEQ ID NO 7
<211> LENGTH: 1350
<212> TYPE: DNA
<213> ORGANISM: mouse
<220> FEATURE:
<221> NAME/KEY: CDS
<222> LOCATION: (1)..(1299)

<400> SEQUENCE: 7 atg cac gtg cgc tcg ctg cgc gct gcg gcg cca cac agc ttc gtg gcg     48
Met His Val Arg Ser Leu Arg Ala Ala Ala Pro His Ser Phe Val Ala
1               5                  10                  15 ctc tgg gcg cct ctg ttc ttg ctg cgc tcc gcc ctg gcc gat ttc agc     96
Leu Trp Ala Pro Leu Phe Leu Leu Arg Ser Ala Leu Ala Asp Phe Ser
            20                  25                  30 ctg gac aac gag gtg cac tcc agc ttc atc cac cgg cgc ctc cgc agc    144
Leu Asp Asn Glu Val His Ser Ser Phe Ile His Arg Arg Leu Arg Ser
        35                  40                  45 cag gag cgg cgg gag atg cag cgg gag atc ctg tcc atc tta ggg ttg    192
Gln Glu Arg Arg Glu Met Gln Arg Glu Ile Leu Ser Ile Leu Gly Leu
    50                  55                  60 ccc cat cgc ccg cgc ccg cac ctc cag gga aag cat aat tcg gcg ccc    240
Pro His Arg Pro Arg Pro His Leu Gln Gly Lys His Asn Ser Ala Pro
65                  70                  75                  80 atg ttc atg ttg gac ctg tac aac gcc atg gcg gtg gag gag agc ggg    288
Met Phe Met Leu Asp Leu Tyr Asn Ala Met Ala Val Glu Glu Ser Gly
                85                  90                  95
```

```
                                          -continued ccg gac gga cag ggc ttc tcc tac ccc tac aag gcc gtc ttc agt acc      336
Pro Asp Gly Gln Gly Phe Ser Tyr Pro Tyr Lys Ala Val Phe Ser Thr
            100                 105                 110 cag ggc ccc cct tta gcc agc ctg cag gac agc cac ttc ctc act gac      384
Gln Gly Pro Pro Leu Ala Ser Leu Gln Asp Ser His Phe Leu Thr Asp
            115                 120                 125 gcc gac atg gtc atg agc ttc gtc aac cta gtg gaa cat gac aaa gaa      432
Ala Asp Met Val Met Ser Phe Val Asn Leu Val Glu His Asp Lys Glu
        130                 135                 140 ttc ttc cac cct cga tac cac cat cgg gag ttc cgg ttt gat ctt tcc      480
Phe Phe His Pro Arg Tyr His His Arg Glu Phe Arg Phe Asp Leu Ser
145                 150                 155                 160 aag atc ccc gag ggc gaa cgg gtg acc gca gcc gaa ttc agg atc tat      528
Lys Ile Pro Glu Gly Glu Arg Val Thr Ala Ala Glu Phe Arg Ile Tyr
                165                 170                 175 aag gac tac atc cgg gag cga ttt gac aac gag acc ttc cag atc aca      576
Lys Asp Tyr Ile Arg Glu Arg Phe Asp Asn Glu Thr Phe Gln Ile Thr
            180                 185                 190 gtc tat cag gtg ctc cag gag cac tca ggc agg gag tcg gac ctc ttc      624
Val Tyr Gln Val Leu Gln Glu His Ser Gly Arg Glu Ser Asp Leu Phe
            195                 200                 205 ttg ctg gac agc cgc acc atc tgg gct tct gag gag ggc tgg ttg gtg      672
Leu Leu Asp Ser Arg Thr Ile Trp Ala Ser Glu Glu Gly Trp Leu Val
        210                 215                 220 ttt gat atc aca gcc acc agc aac cac tgg gtg gtc aac cct cgg cac      720
Phe Asp Ile Thr Ala Thr Ser Asn His Trp Val Val Asn Pro Arg His
225                 230                 235                 240 aac ctg ggc tta cag ctc tct gtg gag acc ctg gat ggg cag agc atc      768
Asn Leu Gly Leu Gln Leu Ser Val Glu Thr Leu Asp Gly Gln Ser Ile
                245                 250                 255 aac ccc aag ttg gca ggc ctg att gga cgg cat gga ccc cag aac aag      816
Asn Pro Lys Leu Ala Gly Leu Ile Gly Arg His Gly Pro Gln Asn Lys
            260                 265                 270 caa ccc ttc atg gtg gcc ttc ttc aag gcc acg gaa gtc cat ctc cgt      864
Gln Pro Phe Met Val Ala Phe Phe Lys Ala Thr Glu Val His Leu Arg
            275                 280                 285 agt atc cgg tcc acg ggg ggc acg cgc cag gag gag gaa tac atg ccc      912
Ser Ile Arg Ser Thr Gly Gly Thr Arg Gln Glu Glu Glu Tyr Met Pro
        290                 295                 300 atg gag acg cgt acc cag tcg cag gac gtg tcc cgg ggc tcc ggt tct      960
Met Glu Thr Arg Thr Gln Ser Gln Asp Val Ser Arg Gly Ser Gly Ser
305                 310                 315                 320 tca gac tac aac ggc agt gag tta aaa aca gct tgc aag aag cat gag     1008
Ser Asp Tyr Asn Gly Ser Glu Leu Lys Thr Ala Cys Lys Lys His Glu
                325                 330                 335 ctc tat gtg agc ttc cag gac ctg gga tgg cag gac tgg atc att gca     1056
Leu Tyr Val Ser Phe Gln Asp Leu Gly Trp Gln Asp Trp Ile Ile Ala
            340                 345                 350 ccc aaa ggc tac gct gcc aac tac tgt gat gga gag tgt tcc ttc cca     1104
Pro Lys Gly Tyr Ala Ala Asn Tyr Cys Asp Gly Glu Cys Ser Phe Pro
        355                 360                 365 ctc aac gca cac atg aat gcc acc aac cac gcc att gta cag acc ttg     1152
Leu Asn Ala His Met Asn Ala Thr Asn His Ala Ile Val Gln Thr Leu
370                 375                 380 gtc cac ctt atg aat ccc gag tac gtc ccc aaa cca tgc tgc gca cca     1200
Val His Leu Met Asn Pro Glu Tyr Val Pro Lys Pro Cys Cys Ala Pro
385                 390                 395                 400 acc aaa ctg aat gcc atc tcg gtt ctt tac ttc gat gat aac tcc aat     1248
Thr Lys Leu Asn Ala Ile Ser Val Leu Tyr Phe Asp Asp Asn Ser Asn
                405                 410                 415
```

-continued

```
gtc atc ttg aaa aag tac agg aat atg gtc gtg aga gct tgt ggt tgc         1296
Val Ile Leu Lys Lys Tyr Arg Asn Met Val Val Arg Ala Cys Gly Cys
            420                 425                 430 cat taagttgaag ctggtgtgtg tgtgtgggtg gggcatggt tctgccttgg a              1350
His
```

<210> SEQ ID NO 8
<211> LENGTH: 433
<212> TYPE: PRT
<213> ORGANISM: mouse

<400> SEQUENCE: 8

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270

Gln Pro Phe Met Val Ala Phe Phe Lys Ala Thr Glu Val His Leu Arg
        275                 280                 285

Ser Ile Arg Ser Thr Gly Gly Thr Arg Gln Glu Glu Tyr Met Pro
    290                 295                 300

Met Glu Thr Arg Thr Gln Ser Gln Asp Val Ser Arg Gly Ser Gly Ser
305                 310                 315                 320

Ser Asp Tyr Asn Gly Ser Glu Leu Lys Thr Ala Cys Lys Lys His Glu
                325                 330                 335
```

```
Leu Tyr Val Ser Phe Gln Asp Leu Gly Trp Gln Asp Trp Ile Ile Ala
            340                 345                 350

Pro Lys Gly Tyr Ala Ala Asn Tyr Cys Asp Gly Glu Cys Ser Phe Pro
        355                 360                 365

Leu Asn Ala His Met Asn Ala Thr Asn His Ala Ile Val Gln Thr Leu
    370                 375                 380

Val His Leu Met Asn Pro Glu Tyr Val Pro Lys Pro Cys Cys Ala Pro
385                 390                 395                 400

Thr Lys Leu Asn Ala Ile Ser Val Leu Tyr Phe Asp Asp Asn Ser Asn
                405                 410                 415

Val Ile Leu Lys Lys Tyr Arg Asn Met Val Val Arg Ala Cys Gly Cys
                420                 425                 430
His

<210> SEQ ID NO 9
<211> LENGTH: 1353
<212> TYPE: DNA
<213> ORGANISM: mouse
<220> FEATURE:
<221> NAME/KEY: CDS
<222> LOCATION: (1)..(1353)

<400> SEQUENCE: 9
```

| | | | | | | | | | | | | | | | | |
|---|---|---|---|---|---|---|---|---|---|---|---|---|---|---|---|---|
| atg | cac | gtg | cgc | tcg | ctg | cgc | gct | gcg | gcg | cca | cac | agc | ttc | gtg | gcg | 48 |
| Met | His | Val | Arg | Ser | Leu | Arg | Ala | Ala | Ala | Pro | His | Ser | Phe | Val | Ala | |
| 1 | | | 5 | | | | | 10 | | | | | 15 | | | |
| ctc | tgg | gcg | cct | ctg | ttc | ttg | ctg | cgc | tcc | gcc | ctg | gcc | gat | ttc | agc | 96 |
| Leu | Trp | Ala | Pro | Leu | Phe | Leu | Leu | Arg | Ser | Ala | Leu | Ala | Asp | Phe | Ser | |
| | | | 20 | | | | | 25 | | | | | 30 | | | |
| ctg | gac | aac | gag | gtg | cac | tcc | agc | ttc | atc | cac | cgg | cgc | ctc | cgc | agc | 144 |
| Leu | Asp | Asn | Glu | Val | His | Ser | Ser | Phe | Ile | His | Arg | Arg | Leu | Arg | Ser | |
| | | 35 | | | | | 40 | | | | | 45 | | | | |
| cag | gag | cgg | cgg | gag | atg | cag | cgg | gag | atc | ctg | tcc | atc | tta | ggg | ttg | 192 |
| Gln | Glu | Arg | Arg | Glu | Met | Gln | Arg | Glu | Ile | Leu | Ser | Ile | Leu | Gly | Leu | |
| 50 | | | | | 55 | | | | | 60 | | | | | | |
| ccc | cat | cgc | ccg | cgc | ccg | cac | ctc | cag | gga | aag | cat | aat | tcg | gcg | ccc | 240 |
| Pro | His | Arg | Pro | Arg | Pro | His | Leu | Gln | Gly | Lys | His | Asn | Ser | Ala | Pro | |
| 65 | | | | | 70 | | | | | 75 | | | | | 80 | |
| atg | ttc | atg | ttg | gac | ctg | tac | aac | gcc | atg | gcg | gtg | gag | gag | agc | ggg | 288 |
| Met | Phe | Met | Leu | Asp | Leu | Tyr | Asn | Ala | Met | Ala | Val | Glu | Glu | Ser | Gly | |
| | | | | 85 | | | | | 90 | | | | | 95 | | |
| ccg | gac | gga | cag | ggc | ttc | tcc | tac | ccc | tac | aag | gcc | gtc | ttc | agt | acc | 336 |
| Pro | Asp | Gly | Gln | Gly | Phe | Ser | Tyr | Pro | Tyr | Lys | Ala | Val | Phe | Ser | Thr | |
| | | | 100 | | | | | 105 | | | | | 110 | | | |
| cag | ggc | ccc | cct | tta | gcc | agc | ctg | cag | gac | agc | cac | ttc | ctc | act | gac | 384 |
| Gln | Gly | Pro | Pro | Leu | Ala | Ser | Leu | Gln | Asp | Ser | His | Phe | Leu | Thr | Asp | |
| | | 115 | | | | | 120 | | | | | 125 | | | | |
| gcc | gac | atg | gtc | atg | agc | ttc | gtc | aac | cta | gtg | gaa | cat | gac | aaa | gaa | 432 |
| Ala | Asp | Met | Val | Met | Ser | Phe | Val | Asn | Leu | Val | Glu | His | Asp | Lys | Glu | |
| | 130 | | | | | 135 | | | | | 140 | | | | | |
| ttc | ttc | cac | cct | cga | tac | cac | cat | cgg | gag | ttc | cgg | ttt | gat | ctt | tcc | 480 |
| Phe | Phe | His | Pro | Arg | Tyr | His | His | Arg | Glu | Phe | Arg | Phe | Asp | Leu | Ser | |
| 145 | | | | | 150 | | | | | 155 | | | | | 160 | |
| aag | atc | ccc | gag | ggc | gaa | cgg | gtg | acc | gca | gcc | gaa | ttc | agg | atc | tat | 528 |
| Lys | Ile | Pro | Glu | Gly | Glu | Arg | Val | Thr | Ala | Ala | Glu | Phe | Arg | Ile | Tyr | |
| | | | | 165 | | | | | 170 | | | | | 175 | | |
| aag | gac | tac | atc | cgg | gag | cga | ttt | gac | aac | gag | acc | ttc | cag | atc | aca | 576 |
| Lys | Asp | Tyr | Ile | Arg | Glu | Arg | Phe | Asp | Asn | Glu | Thr | Phe | Gln | Ile | Thr | |
| | | | 180 | | | | | 185 | | | | | 190 | | | |
| gtc | tat | cag | gtg | ctc | cag | gag | cac | tca | ggc | agg | gag | tcg | gac | ctc | ttc | 624 |

``` ttg ctg gac agc cgc acc atc tgg gct tct gag gag ggc tgg ttg gtg        672
Leu Leu Asp Ser Arg Thr Ile Trp Ala Ser Glu Glu Gly Trp Leu Val
    210                 215                 220 ttt gat atc aca gcc acc agc aac cac tgg gtg gtc aac cct cgg cac        720
Phe Asp Ile Thr Ala Thr Ser Asn His Trp Val Val Asn Pro Arg His
225                 230                 235                 240 aac ctg ggc tta cag ctc tct gtg gag acc ctg gat ggg cag agc atc        768
Asn Leu Gly Leu Gln Leu Ser Val Glu Thr Leu Asp Gly Gln Ser Ile
                245                 250                 255 aac ccc aag ttg gca ggc ctg att gga cgg cat gga ccc cag aac aag        816
Asn Pro Lys Leu Ala Gly Leu Ile Gly Arg His Gly Pro Gln Asn Lys
            260                 265                 270 caa ccc ttc atg gtg gcc ttc ttc aag gcc acg gaa gtc cat ctc cgt        864
Gln Pro Phe Met Val Ala Phe Phe Lys Ala Thr Glu Val His Leu Arg
        275                 280                 285 agt atc cgg tcc acg ggg ggc acg cgc cag gag cag aag ctt atc tcg        912
Ser Ile Arg Ser Thr Gly Gly Thr Arg Gln Glu Gln Lys Leu Ile Ser
    290                 295                 300 gag gag gac ctg acg cgt acc cag tcg cag gac gtg tcc cgg ggc tcc        960
Glu Glu Asp Leu Thr Arg Thr Gln Ser Gln Asp Val Ser Arg Gly Ser
305                 310                 315                 320 ggt tct tca gac tac aac ggc agt gag tta aaa aca gct tgc aag aag       1008
Gly Ser Ser Asp Tyr Asn Gly Ser Glu Leu Lys Thr Ala Cys Lys Lys
                325                 330                 335 cat gag ctc tat gtg agc ttc cag gac ctg gga tgg cag gac tgg atc       1056
His Glu Leu Tyr Val Ser Phe Gln Asp Leu Gly Trp Gln Asp Trp Ile
            340                 345                 350 att gca ccc aaa ggc tac gct gcc aac tac tgt gat gga gag tgt tcc       1104
Ile Ala Pro Lys Gly Tyr Ala Ala Asn Tyr Cys Asp Gly Glu Cys Ser
        355                 360                 365 ttc cca ctc aac gca cac atg aat gcc acc aac cac gcc att gta cag       1152
Phe Pro Leu Asn Ala His Met Asn Ala Thr Asn His Ala Ile Val Gln
    370                 375                 380 acc ttg gtc cac ctt atg aat ccc gag tac gtc ccc aaa cca tgc tgc       1200
Thr Leu Val His Leu Met Asn Pro Glu Tyr Val Pro Lys Pro Cys Cys
385                 390                 395                 400 gca cca acc aaa ctg aat gcc atc tcg gtt ctt tac ttc gat gat aac       1248
Ala Pro Thr Lys Leu Asn Ala Ile Ser Val Leu Tyr Phe Asp Asp Asn
                405                 410                 415 tcc aat gtc atc ttg aaa aag tac agg aat atg gtc gtg aga gct tgt       1296
Ser Asn Val Ile Leu Lys Lys Tyr Arg Asn Met Val Val Arg Ala Cys
            420                 425                 430 ggt tgc cat gtt gaa gct ggt gtg tgt gtg tgg gtg ggg gca tgg ttc       1344
Gly Cys His Val Glu Ala Gly Val Cys Val Trp Val Gly Ala Trp Phe
        435                 440                 445 tgc ctt gga                                                            1353
Cys Leu Gly
    450

<210> SEQ ID NO 10
<211> LENGTH: 451
<212> TYPE: PRT
<213> ORGANISM: mouse

<400> SEQUENCE: 10

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
```

-continued

```
                20                  25                  30
Leu Asp Asn Glu Val His Ser Ser Phe Ile His Arg Arg Leu Arg Ser
            35                  40                  45
Gln Glu Arg Arg Glu Met Gln Arg Glu Ile Leu Ser Ile Leu Gly Leu
        50                  55                  60
Pro His Arg Pro Arg Pro His Leu Gln Gly Lys His Asn Ser Ala Pro
65                  70                  75                  80
Met Phe Met Leu Asp Leu Tyr Asn Ala Met Ala Val Glu Glu Ser Gly
                85                  90                  95
Pro Asp Gly Gln Gly Phe Ser Tyr Pro Tyr Lys Ala Val Phe Ser Thr
            100                 105                 110
Gln Gly Pro Pro Leu Ala Ser Leu Gln Asp Ser His Phe Leu Thr Asp
        115                 120                 125
Ala Asp Met Val Met Ser Phe Val Asn Leu Val Glu His Asp Lys Glu
    130                 135                 140
Phe Phe His Pro Arg Tyr His His Arg Glu Phe Arg Phe Asp Leu Ser
145                 150                 155                 160
Lys Ile Pro Glu Gly Glu Arg Val Thr Ala Ala Glu Phe Arg Ile Tyr
                165                 170                 175
Lys Asp Tyr Ile Arg Glu Arg Phe Asp Asn Glu Thr Phe Gln Ile Thr
            180                 185                 190
Val Tyr Gln Val Leu Gln Glu His Ser Gly Arg Glu Ser Asp Leu Phe
        195                 200                 205
Leu Leu Asp Ser Arg Thr Ile Trp Ala Ser Glu Glu Gly Trp Leu Val
    210                 215                 220
Phe Asp Ile Thr Ala Thr Ser Asn His Trp Val Val Asn Pro Arg His
225                 230                 235                 240
Asn Leu Gly Leu Gln Leu Ser Val Glu Thr Leu Asp Gly Gln Ser Ile
                245                 250                 255
Asn Pro Lys Leu Ala Gly Leu Ile Gly Arg His Gly Pro Gln Asn Lys
            260                 265                 270
Gln Pro Phe Met Val Ala Phe Phe Lys Ala Thr Glu Val His Leu Arg
        275                 280                 285
Ser Ile Arg Ser Thr Gly Gly Thr Arg Gln Glu Gln Lys Leu Ile Ser
    290                 295                 300
Glu Glu Asp Leu Thr Arg Thr Gln Ser Gln Asp Val Ser Arg Gly Ser
305                 310                 315                 320
Gly Ser Ser Asp Tyr Asn Gly Ser Glu Leu Lys Thr Ala Cys Lys Lys
                325                 330                 335
His Glu Leu Tyr Val Ser Phe Gln Asp Leu Gly Trp Gln Asp Trp Ile
            340                 345                 350
Ile Ala Pro Lys Gly Tyr Ala Ala Asn Tyr Cys Asp Gly Glu Cys Ser
        355                 360                 365
Phe Pro Leu Asn Ala His Met Asn Ala Thr Asn His Ala Ile Val Gln
    370                 375                 380
Thr Leu Val His Leu Met Asn Pro Glu Tyr Val Pro Lys Pro Cys Cys
385                 390                 395                 400
Ala Pro Thr Lys Leu Asn Ala Ile Ser Val Leu Tyr Phe Asp Asp Asn
                405                 410                 415
Ser Asn Val Ile Leu Lys Lys Tyr Arg Asn Met Val Val Arg Ala Cys
            420                 425                 430
Gly Cys His Val Glu Ala Gly Val Cys Val Trp Val Gly Ala Trp Phe
        435                 440                 445
```

```
Cys Leu Gly
    450

<210> SEQ ID NO 11
<211> LENGTH: 1346
<212> TYPE: DNA
<213> ORGANISM: mouse
<220> FEATURE:
<221> NAME/KEY: CDS
<222> LOCATION: (1)..(1299)

<400> SEQUENCE: 11 atg cac gtg cgc tcg ctg cgc gct gcg gcg cca cac agc ttc gtg gcg      48
Met His Val Arg Ser Leu Arg Ala Ala Ala Pro His Ser Phe Val Ala
1               5                   10                  15 ctc tgg gcg cct ctg ttc ttg ctg cgc tcc gcc ctg gcc gat ttc agc      96
Leu Trp Ala Pro Leu Phe Leu Leu Arg Ser Ala Leu Ala Asp Phe Ser
                20                  25                  30 ctg gac aac gag gtg cac tcc agc ttc atc cac cgg cgc ctc cgc agc     144
Leu Asp Asn Glu Val His Ser Ser Phe Ile His Arg Arg Leu Arg Ser
            35                  40                  45 cag gag cgg cgg gag atg cag cgg gag atc ctg tcc atc tta ggg ttg     192
Gln Glu Arg Arg Glu Met Gln Arg Glu Ile Leu Ser Ile Leu Gly Leu
        50                  55                  60 ccc cat cgc ccg cgc ccg cac ctc cag gga aag cat aat tcg gcg ccc     240
Pro His Arg Pro Arg Pro His Leu Gln Gly Lys His Asn Ser Ala Pro
65                  70                  75                  80 atg ttc atg ttg gac ctg tac aac gcc atg gcg gtg gag gag agc ggg     288
Met Phe Met Leu Asp Leu Tyr Asn Ala Met Ala Val Glu Glu Ser Gly
                85                  90                  95 ccg gac gga cag ggc ttc tcc tac ccc tac aag gcc gtc ttc agt acc     336
Pro Asp Gly Gln Gly Phe Ser Tyr Pro Tyr Lys Ala Val Phe Ser Thr
            100                 105                 110 cag ggc ccc cct tta gcc agc ctg cag gac agc cac ttc ctc act gac     384
Gln Gly Pro Pro Leu Ala Ser Leu Gln Asp Ser His Phe Leu Thr Asp
        115                 120                 125 gcc gac atg gtc atg agc ttc gtc aac cta gtg gaa cat gac aaa gaa     432
Ala Asp Met Val Met Ser Phe Val Asn Leu Val Glu His Asp Lys Glu
    130                 135                 140 ttc ttc cac cct cga tac cac cat cgg gag ttc cgg ttt gat ctt tcc     480
Phe Phe His Pro Arg Tyr His His Arg Glu Phe Arg Phe Asp Leu Ser
145                 150                 155                 160 aag atc ccc gag ggc gaa cgg gtg acc gca gcc gaa ttc agg atc tat     528
Lys Ile Pro Glu Gly Glu Arg Val Thr Ala Ala Glu Phe Arg Ile Tyr
                165                 170                 175 aag gac tac atc cgg gag cga ttt gac aac gag acc ttc cag atc aca     576
Lys Asp Tyr Ile Arg Glu Arg Phe Asp Asn Glu Thr Phe Gln Ile Thr
            180                 185                 190 gtc tat cag gtg ctc cag gag cac tca ggc agg gag tcg gac ctc ttc     624
Val Tyr Gln Val Leu Gln Glu His Ser Gly Arg Glu Ser Asp Leu Phe
        195                 200                 205 ttg ctg gac agc cgc acc atc tgg gct tct gag gag ggc tgg ttg gtg     672
Leu Leu Asp Ser Arg Thr Ile Trp Ala Ser Glu Glu Gly Trp Leu Val
    210                 215                 220 ttt gat atc aca gcc acc agc aac cac tgg gtg gtc aac cct cgg cac     720
Phe Asp Ile Thr Ala Thr Ser Asn His Trp Val Val Asn Pro Arg His
225                 230                 235                 240 aac ctg ggc tta cag ctc tct gtg gag acc ctg gat ggg cag agc atc     768
Asn Leu Gly Leu Gln Leu Ser Val Glu Thr Leu Asp Gly Gln Ser Ile
                245                 250                 255
```

```
aac ccc aag ttg gca ggc ctg att gga cgg cat gga ccc cag aac aag        816
Asn Pro Lys Leu Ala Gly Leu Ile Gly Arg His Gly Pro Gln Asn Lys
        260                 265                 270 caa ccc ttc atg gtg gcc ttc ttc aag gcc acg gaa gtc cat ctc cgt        864
Gln Pro Phe Met Val Ala Phe Phe Lys Ala Thr Glu Val His Leu Arg
            275                 280                 285 agt atc cgg tcc acg ggg ggc acg cgc cag gag gag gaa tac atg ccc        912
Ser Ile Arg Ser Thr Gly Gly Thr Arg Gln Glu Glu Glu Tyr Met Pro
290                 295                 300 atg gag acg cgt cca aag aac caa gag gcc ctg agg atg gcc agt gtg        960
Met Glu Thr Arg Pro Lys Asn Gln Glu Ala Leu Arg Met Ala Ser Val
305                 310                 315                 320 gca gaa aac agc agc agt gac cag agg cag gcc tgc aag aaa cat gag       1008
Ala Glu Asn Ser Ser Ser Asp Gln Arg Gln Ala Cys Lys Lys His Glu
                325                 330                 335 ctg tac gtc agc ttc cga gac ctt ggc tgg cag gac tgg atc att gca       1056
Leu Tyr Val Ser Phe Arg Asp Leu Gly Trp Gln Asp Trp Ile Ile Ala
            340                 345                 350 cct gaa ggc tat gct gcc tac tac tgt gag gga gag tgc gcc ttc cct       1104
Pro Glu Gly Tyr Ala Ala Tyr Tyr Cys Glu Gly Glu Cys Ala Phe Pro
        355                 360                 365 ctg aac tcc tac atg aac gcc acc aac cac gcc atc gtc cag aca ctg       1152
Leu Asn Ser Tyr Met Asn Ala Thr Asn His Ala Ile Val Gln Thr Leu
    370                 375                 380 gtt cac ttc atc aac cca gac aca gta ccc aag ccc tgc tgt gcg ccc       1200
Val His Phe Ile Asn Pro Asp Thr Val Pro Lys Pro Cys Cys Ala Pro
385                 390                 395                 400 acc cag ctc aac gcc atc tct gtc ctc tac ttc gac gac agc tct aat       1248
Thr Gln Leu Asn Ala Ile Ser Val Leu Tyr Phe Asp Asp Ser Ser Asn
                405                 410                 415 gtc atc ctg aag aag tac aga aac atg gtg gtc cgg gcc tgt ggc tgc       1296
Val Ile Leu Lys Lys Tyr Arg Asn Met Val Val Arg Ala Cys Gly Cys
            420                 425                 430 cac tagctcttcc tgagaccctg acctttgcgg ggccacacct ttccaaa               1346
His

<210> SEQ ID NO 12
<211> LENGTH: 433
<212> TYPE: PRT
<213> ORGANISM: mouse

<400> SEQUENCE: 12

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125
```

```
Ala Asp Met Val Met Ser Phe Val Asn Leu Val Glu His Asp Lys Glu
    130                 135                 140

Phe Phe His Pro Arg Tyr His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
                180                 185                 190

Val Tyr Gln Val Leu Gln Glu His Ser Gly Arg Glu Ser Asp Leu Phe
                195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
                260                 265                 270

Gln Pro Phe Met Val Ala Phe Phe Lys Ala Thr Glu Val His Leu Arg
                275                 280                 285

Ser Ile Arg Ser Thr Gly Gly Thr Arg Gln Glu Glu Tyr Met Pro
    290                 295                 300

Met Glu Thr Arg Pro Lys Asn Gln Glu Ala Leu Arg Met Ala Ser Val
305                 310                 315                 320

Ala Glu Asn Ser Ser Ser Asp Gln Arg Gln Ala Cys Lys Lys His Glu
                325                 330                 335

Leu Tyr Val Ser Phe Arg Asp Leu Gly Trp Gln Asp Trp Ile Ile Ala
                340                 345                 350

Pro Glu Gly Tyr Ala Ala Tyr Tyr Cys Glu Gly Glu Cys Ala Phe Pro
                355                 360                 365

Leu Asn Ser Tyr Met Asn Ala Thr Asn His Ala Ile Val Gln Thr Leu
    370                 375                 380

Val His Phe Ile Asn Pro Asp Thr Val Pro Lys Pro Cys Cys Ala Pro
385                 390                 395                 400

Thr Gln Leu Asn Ala Ile Ser Val Leu Tyr Phe Asp Asp Ser Ser Asn
                405                 410                 415

Val Ile Leu Lys Lys Tyr Arg Asn Met Val Val Arg Ala Cys Gly Cys
                420                 425                 430
His

<210> SEQ ID NO 13
<211> LENGTH: 1352
<212> TYPE: DNA
<213> ORGANISM: mouse
<220> FEATURE:
<221> NAME/KEY: CDS
<222> LOCATION: (1)..(1305)

<400> SEQUENCE: 13 atg cac gtg cgc tcg ctg cgc gct gcg gcg cca cac agc ttc gtg gcg    48
Met His Val Arg Ser Leu Arg Ala Ala Ala Pro His Ser Phe Val Ala
1                 5                  10                  15 ctc tgg gcg cct ctg ttc ttg ctg cgc tcc gcc ctg gcc gat ttc agc    96
Leu Trp Ala Pro Leu Phe Leu Leu Arg Ser Ala Leu Ala Asp Phe Ser
                20                  25                  30 ctg gac aac gag gtg cac tcc agc ttc atc cac cgg cgc ctc cgc agc   144
Leu Asp Asn Glu Val His Ser Ser Phe Ile His Arg Arg Leu Arg Ser
```

-continued

| | | |
|---|---|---|
| cag gag cgg cgg gag atg cag cgg gag atc ctg tcc atc tta ggg ttg<br>Gln Glu Arg Arg Glu Met Gln Arg Glu Ile Leu Ser Ile Leu Gly Leu<br>50               55                  60 | 192 | |
| ccc cat cgc ccg cgc ccg cac ctc cag gga aag cat aat tcg gcg ccc<br>Pro His Arg Pro Arg Pro His Leu Gln Gly Lys His Asn Ser Ala Pro<br>65           70                  75                  80 | 240 | |
| atg ttc atg ttg gac ctg tac aac gcc atg gcg gtg gag gag agc ggg<br>Met Phe Met Leu Asp Leu Tyr Asn Ala Met Ala Val Glu Glu Ser Gly<br>               85                  90                  95 | 288 | |
| ccg gac gga cag ggc ttc tcc tac ccc tac aag gcc gtc ttc agt acc<br>Pro Asp Gly Gln Gly Phe Ser Tyr Pro Tyr Lys Ala Val Phe Ser Thr<br>         100                 105                 110 | 336 | |
| cag ggc ccc cct tta gcc agc ctg cag gac agc cac ttc ctc act gac<br>Gln Gly Pro Pro Leu Ala Ser Leu Gln Asp Ser His Phe Leu Thr Asp<br>     115                 120                 125 | 384 | |
| gcc gac atg gtc atg agc ttc gtc aac cta gtg gaa cat gac aaa gaa<br>Ala Asp Met Val Met Ser Phe Val Asn Leu Val Glu His Asp Lys Glu<br>130                 135                 140 | 432 | |
| ttc ttc cac cct cga tac cac cat cgg gag ttc cgg ttt gat ctt tcc<br>Phe Phe His Pro Arg Tyr His His Arg Glu Phe Arg Phe Asp Leu Ser<br>145                 150                 155                 160 | 480 | |
| aag atc ccc gag ggc gaa cgg gtg acc gca gcc gaa ttc agg atc tat<br>Lys Ile Pro Glu Gly Glu Arg Val Thr Ala Ala Glu Phe Arg Ile Tyr<br>                 165                 170                 175 | 528 | |
| aag gac tac atc cgg gag cga ttt gac aac gag acc ttc cag atc aca<br>Lys Asp Tyr Ile Arg Glu Arg Phe Asp Asn Glu Thr Phe Gln Ile Thr<br>             180                 185                 190 | 576 | |
| gtc tat cag gtg ctc cag gag cac tca ggc agg gag tcg gac ctc ttc<br>Val Tyr Gln Val Leu Gln Glu His Ser Gly Arg Glu Ser Asp Leu Phe<br>         195                 200                 205 | 624 | |
| ttg ctg gac agc cgc acc atc tgg gct tct gag gag ggc tgg ttg gtg<br>Leu Leu Asp Ser Arg Thr Ile Trp Ala Ser Glu Glu Gly Trp Leu Val<br>     210                 215                 220 | 672 | |
| ttt gat atc aca gcc acc agc aac cac tgg gtg gtc aac cct cgg cac<br>Phe Asp Ile Thr Ala Thr Ser Asn His Trp Val Val Asn Pro Arg His<br>225                 230                 235                 240 | 720 | |
| aac ctg ggc tta cag ctc tct gtg gag acc ctg gat ggg cag agc atc<br>Asn Leu Gly Leu Gln Leu Ser Val Glu Thr Leu Asp Gly Gln Ser Ile<br>                 245                 250                 255 | 768 | |
| aac ccc aag ttg gca ggc ctg att gga cgg cat gga ccc cag aac aag<br>Asn Pro Lys Leu Ala Gly Leu Ile Gly Arg His Gly Pro Gln Asn Lys<br>             260                 265                 270 | 816 | |
| caa ccc ttc atg gtg gcc ttc ttc aag gcc acg gaa gtc cat ctc cgt<br>Gln Pro Phe Met Val Ala Phe Phe Lys Ala Thr Glu Val His Leu Arg<br>         275                 280                 285 | 864 | |
| agt atc cgg tcc acg ggg ggc acg cgc cag gag cag aag ctt atc tcg<br>Ser Ile Arg Ser Thr Gly Gly Thr Arg Gln Glu Gln Lys Leu Ile Ser<br>     290                 295                 300 | 912 | |
| gag gag gac ctg acg cgt cca aag aac caa gag gcc ctg agg atg gcc<br>Glu Glu Asp Leu Thr Arg Pro Lys Asn Gln Glu Ala Leu Arg Met Ala<br>305                 310                 315                 320 | 960 | |
| agt gtg gca gaa aac agc agc agt gac cag agg cag gcc tgc aag aaa<br>Ser Val Ala Glu Asn Ser Ser Ser Asp Gln Arg Gln Ala Cys Lys Lys<br>                 325                 330                 335 | 1008 | |
| cat gag ctg tac gtc agc ttc cga gac ctt ggc tgg cag gac tgg atc<br>His Glu Leu Tyr Val Ser Phe Arg Asp Leu Gly Trp Gln Asp Trp Ile<br>             340                 345                 350 | 1056 | |
| att gca cct gaa ggc tat gct gcc tac tac tgt gag gga gag tgc gcc | 1104 | |

```
          Ile Ala Pro Glu Gly Tyr Ala Ala Tyr Tyr Cys Glu Gly Glu Cys Ala
                          355                 360                 365 ttc cct ctg aac tcc tac atg aac gcc acc aac cac gcc atc gtc cag            1152
Phe Pro Leu Asn Ser Tyr Met Asn Ala Thr Asn His Ala Ile Val Gln
            370                 375                 380 aca ctg gtt cac ttc atc aac cca gac aca gta ccc aag ccc tgc tgt            1200
Thr Leu Val His Phe Ile Asn Pro Asp Thr Val Pro Lys Pro Cys Cys
385                 390                 395                 400 gcg ccc acc cag ctc aac gcc atc tct gtc ctc tac ttc gac gac agc            1248
Ala Pro Thr Gln Leu Asn Ala Ile Ser Val Leu Tyr Phe Asp Asp Ser
                405                 410                 415 tct aat gtc atc ctg aag aag tac aga aac atg gtg gtc cgg gcc tgt            1296
Ser Asn Val Ile Leu Lys Lys Tyr Arg Asn Met Val Val Arg Ala Cys
                    420                 425                 430 ggc tgc cac tagctcttcc tgagaccctg acctttgcgg ggccacacct ttccaaa            1352
Gly Cys His
            435

<210> SEQ ID NO 14
<211> LENGTH: 435
<212> TYPE: PRT
<213> ORGANISM: mouse

<400> SEQUENCE: 14

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255
```

-continued

```
            Asn Pro Lys Leu Ala Gly Leu Ile Gly Arg His Gly Pro Gln Asn Lys
                            260                 265                 270

Gln Pro Phe Met Val Ala Phe Phe Lys Ala Thr Glu Val His Leu Arg
                        275                 280                 285

Ser Ile Arg Ser Thr Gly Gly Thr Arg Gln Glu Gln Lys Leu Ile Ser
                        290                 295                 300

Glu Glu Asp Leu Thr Arg Pro Lys Asn Gln Glu Ala Leu Arg Met Ala
            305                 310                 315                 320

Ser Val Ala Glu Asn Ser Ser Asp Gln Arg Gln Ala Cys Lys Lys
                            325                 330                 335

His Glu Leu Tyr Val Ser Phe Arg Asp Leu Gly Trp Gln Asp Trp Ile
                            340                 345                 350

Ile Ala Pro Glu Gly Tyr Ala Ala Tyr Tyr Cys Glu Gly Glu Cys Ala
                        355                 360                 365

Phe Pro Leu Asn Ser Tyr Met Asn Ala Thr Asn His Ala Ile Val Gln
                        370                 375                 380

Thr Leu Val His Phe Ile Asn Pro Asp Thr Val Pro Lys Pro Cys Cys
            385                 390                 395                 400

Ala Pro Thr Gln Leu Asn Ala Ile Ser Val Leu Tyr Phe Asp Asp Ser
                            405                 410                 415

Ser Asn Val Ile Leu Lys Lys Tyr Arg Asn Met Val Val Arg Ala Cys
                            420                 425                 430

Gly Cys His
                    435

<210> SEQ ID NO 15
<211> LENGTH: 25
<212> TYPE: DNA
<213> ORGANISM: primer

<400> SEQUENCE: 15
gtggaggaac ttccagagat gagtg                                           25

<210> SEQ ID NO 16
<211> LENGTH: 26
<212> TYPE: DNA
<213> ORGANISM: primer

<400> SEQUENCE: 16
atttattctt gctgtgctaa cgacac                                          26

<210> SEQ ID NO 17
<211> LENGTH: 26
<212> TYPE: DNA
<213> ORGANISM: primer

<400> SEQUENCE: 17
catcccaggg accagtgaga gctctg                                          26

<210> SEQ ID NO 18
<211> LENGTH: 25
<212> TYPE: DNA
<213> ORGANISM: primer

<400> SEQUENCE: 18
tccgccctcc ggactgcctg atctc                                           25

<210> SEQ ID NO 19
<211> LENGTH: 25
```

```
<212> TYPE: DNA
<213> ORGANISM: primer

<400> SEQUENCE: 19
gagcacagca aggcttggga acatg                                    25

<210> SEQ ID NO 20
<211> LENGTH: 24
<212> TYPE: DNA
<213> ORGANISM: primer

<400> SEQUENCE: 20
gctggagatt ataataccag tgaa                                     24

<210> SEQ ID NO 21
<211> LENGTH: 26
<212> TYPE: DNA
<213> ORGANISM: primer

<400> SEQUENCE: 21
gttcttcaga ctacaacggc agtgag                                   26

<210> SEQ ID NO 22
<211> LENGTH: 25
<212> TYPE: DNA
<213> ORGANISM: primer

<400> SEQUENCE: 22
gttaggaatc caaggcagaa ccatg                                    25

<210> SEQ ID NO 23
<211> LENGTH: 26
<212> TYPE: DNA
<213> ORGANISM: primer

<400> SEQUENCE: 23
gtgtggcaga aaacagcagc agtgac                                   26

<210> SEQ ID NO 24
<211> LENGTH: 25
<212> TYPE: DNA
<213> ORGANISM: primer

<400> SEQUENCE: 24
gacatcgaag atttggaaag gtgtg                                    25

<210> SEQ ID NO 25
<211> LENGTH: 25
<212> TYPE: DNA
<213> ORGANISM: primer

<400> SEQUENCE: 25
accaactatt gcttcagctc cacag                                    25

<210> SEQ ID NO 26
<211> LENGTH: 25
<212> TYPE: DNA
<213> ORGANISM: primer

<400> SEQUENCE: 26
gcaggagcgc acaatcatgt tggac                                    25

<210> SEQ ID NO 27
```

-continued

```
<211> LENGTH: 25
<212> TYPE: DNA
<213> ORGANISM: primer

<400> SEQUENCE: 27
cttggagtgc gacggcaagg tcaac                                              25

<210> SEQ ID NO 28
<211> LENGTH: 20
<212> TYPE: DNA
<213> ORGANISM: primer

<400> SEQUENCE: 28
gtgggccgcc ctaggcacca                                                    20

<210> SEQ ID NO 29
<211> LENGTH: 25
<212> TYPE: DNA
<213> ORGANISM: primer

<400> SEQUENCE: 29
cattttctct gggacctggc gactc                                              25

<210> SEQ ID NO 30
<211> LENGTH: 24
<212> TYPE: DNA
<213> ORGANISM: primer

<400> SEQUENCE: 30
ctctttgatg tcacgcacga tttc                                               24
```

PANCREATIC ISLET CELL GROWTH FACTORS

CROSS-REFERENCE TO RELATED APPLICATIONS

This application claims benefit of U.S. Provisional Application No. 60/183,573, filed Feb. 18, 2000.

FIELD OF THE INVENTION

The present invention relates generally to growth factors and more particularly to growth factors which are capable of stimulating or otherwise facilitating formation of insulin-secreting cells. The identification of these growth factors permits the development of protocols to culture cells in vitro for transplantation into mammalian and in particular human subjects with insulin-dependent type 1 diabetes or related conditions. It is further contemplated that the endogenous expression of growth factors required for the development of insulin-producing cells may be manipulated in vivo, by the appropriate administration of agents including genetic agents capable of regulating the expression of growth factors in pancreatic duct epithelial cells. The growth factors may also be administered to subjects with type 1 diabetes to stimulate the proliferation and differentiation of pancreatic cells into insulin-secreting cells. The present invention also provides modulators of growth factor-mediated pancreatic cell differentiation. Such modulators are useful in the treatment inter alia of β cell tumors and/or pancreatic cancer.

BACKGROUND OF THE INVENTION

Reference to any prior art in this specification is not, and should not be taken as, an acknowledgment or any form of suggestion that this prior art forms part of the common general knowledge in Australia or any other country.

Bibliographic details of the publications referred to by author in this specification are collected at the end of the description.

Insulin-dependent type 1 diabetes is caused by lack of insulin, due to autoimmune-mediated destruction of pancreatic islet cells. People with type 1 diabetes need regular insulin injections to control their blood glucose level, a matter of life or death. Pancreas transplantation is currently the only curative therapy for type 1 diabetes, but it is hampered by the requirement for potentially toxic, life-long immunosuppressive drugs and by the dearth of human donors. These barriers could be overcome by discovery of growth factors to (re)generate cells.

The factors and mechanisms which regulate lineage differentiation of islet cells from multi-potent precursors are poorly understood. Broadly speaking, two classes of co-operative signals guide cellular proliferation, differentiation and apoptosis: soluble signals including hormones and growth factors and insoluble signals delivered by extracellular matrix (ECM) proteins (Lelievre et al., 1996). Classical hormones play important roles in regulating endocrine cell development. For example, pituitary luteinizing hormone (LH) controls lineage differentiation of Leydig cells in the testis and of granulosa cells in the ovary, while thyroid stimulating hormone (TSH) and adrenocortico trophic hormone (ACTH) maintain differentiation of thyroid follicular cells and adrenocortical cells, respectively. Islet cell development seems to be an exception, as no hormonal control has been demonstrated.

The mammalian pancreatic primordia evaginate from foregut endoderm in early fetal life. The adult pancreas consists of two distinct tissue types: endocrine tissue, the islets of Langerhans, which secrete hormones into the bloodstream, and exocrine tissue, which secretes digestive enzymes into the intestinal tract. The islets contain four main types of endocrine cells that synthesize insulin, glucagon, somatostatin and pancreatic polypeptide. These hormones, notably insulin, play critical roles in glucose metabolism and homeostatis. All four types of endocrine cells are believed to arise from common multi-potent precursors which express the PDX-1 (also called IPF-1, STF-1 and IDX-1) transcription factor and co-express several hormones and neuronal markers as they begin to differentiate (Slack, 1995). Several soluble extracellular factors have been implicated in pancreatic epithelial cell development, including members of the TGF-β1 superfamily of transforming growth factors. Transgenic mice expressing a dominant negative TGF-β receptor II controlled by the mouse metallothionein 1 promoter display increased proliferation and impaired differentiation of pancreatic acinar cells (Bottinger et al., 1997). Transgenic mice expressing a dominant negative activin receptor controlled by the human insulin promoter have hypoplasia of pancreatic islets (Yamaoka et al., 1998). Hebrok et al. (1998) found that Activin B is expressed in the notochord adjacent to the domain of foregut endoderm from which the pancreatic primordia derives. Activin B represses endodermal expression of sonic hedgehog, a prerequisite for expression of the homeodomain transcription factor, PDX-1, required for pancreatic development (Jonsson et al., 1994; Offield et al, 1996). The bone morphogenetics (BMPs), members of the TGF-β superfamily, have been shown to be important in development of kidney tubule, lung and other organ epithelia (Hogan, B. L, 1996; Weaver et al., 1999) and are expressed in the pancreas. BMP 7 was detected immunocytochemically in human fetal pancreas duct epithelium (Vukicevic et al., 1994) and by mRNA in situ hybridization in mouse pancreas epithelium between E12.5 and E14.5 (Lyons et al, 1995). The appropriate and timely expression of these factors contributes to the appropriate embryonic development of the pancreas.

Laminin-1 is a heterotrimeric cellular matrix glycoprotein (Mr=850,000) composed of (400 kDa), (210 kDa) and (200 kDa) disulfide-bonded chains (Ekblom, 1996). Laminin-1 has been shown to induce specifically β-casein gene expression in mammary epithelia (Streuli et al., 1995) and neuron generation from retinal neuroepithelial cells (Frade et al., 1996). The cross region of laminin-1 selectively promotes fetal lung epithelial cell proliferation, the outer globular region of the α1 and β1 chains mediates epithelial cell polarization, and the inner globular region of the β1 chain binds to heparin sulfate proteoglycan and stimulates lumen formation (Schuger et al., 1996). There are at least two types of laminin-1 receptor: the $\alpha_6$ integrins and the non-integrin α-dystroglycan (αDG) (Ekblom, 1996). Integrins are a well-characterized family of heterodimeric cell adhesion molecules composed of non-covalently bound (120–180 kDa) and (90–110 kDa) subunits. αDG is a 156 kDa extracellular peripheral membrane glycoprotein associating with a transmembrane glycoprotein, which binds laminin-1 with high affinity but does not bind nidogen, fibronectin or collagen IV (Ekblom, 1996). The present inventors have found by RT-PCR that mRNAs for $\alpha_6$ integrin and αDG are expressed in the developing mouse pancreas from at least 13.5 dpc and $\alpha_6$ integrin protein is detected by immunofluorescence from at least 15.5 dpc. Coincident with these laminin-1 studies, the present inventors also carried out a representational difference analysis (RDA) in which genes expressed in normal human pancreas were subtracted from genes expressed in pancreas from a child with diffuse islet cell hyperplasia (nesidioblastosis). One of the genes found to be differentially expressed in nesidioblastosis was bone morphogenetic protein (BMP) 7. BMPs were originally identified as proteins that induce bone and cartilage formation in ectopic extraskeletal sites in vivo (Wozney, 1989). In vitro studies have revealed that BMPs have multiple effects on various cells types. BMP-2 deficient mice have amnion/chorion malformation and defective cardiac development, and die between 7.5–9 dpc (Zhang and Bradley, 1996). BMP 4 deficient mice have defects in extra-embryonic and posterior/ventral mesoderm formation and die between 6.5–9.5 dpc (Winnier et al., 1995). BMP 7 deficient mice have defects in kidneys and eyes and die shortly after birth (Dudley et al., 1995; Luo et al., 1995).

In work leading up to the present invention, the inventors developed a low cell density, serum-free culture system for dissociated pancreatic cells from 13.5 day-postcoitum (dpc) mouse fetuses and investigated the effects of four major ECM proteins, collagens I and IV, fibronectin and laminin-1, on the differentiation of fetal pancreatic cells into islet cells (Jiang et al., 1999). Following four days of culture in complete HYBRIDOMA medium, the total cell number decreased to one-third of that plated, but the number of insulin-positive cells increased 10-fold. Both collagens I and IV inhibited (by over 50%) the survival of pancreatic cells compared to medium alone, whereas fibronectin had no effect. However, in the presence of soluble laminin-1, the number of cells increased linearly by 60-fold. Laminin-1 was also shown to be expressed in the epithelial basement membrane of the 13.5–17.5 day fetal pancreas (Jiang et al., 1999). These results provided the first evidence that laminin-1 plays an important role in promoting differentiation of pancreatic cells. The present inventors have further developed an in vivo culture system in which the interaction of laminin-1 with particular BMPs has a synergistic effect which result in an increased frequency in the formation of cystic epithelial colonies that contain insulin-producing cells. The subject inventors showed that they are able to regulate the development and formation of cystic epithelial colonies which contain cells that express insulin by modulating the quantity of particular BMPs and/or laminin-1. The present inventors further identified that TGF β1 and Activin A antagonize the activity of particular BMPs. Thus, the present inventors are now able to regulate the development of insulin-producing β-cells from pancreatic epithelial cells in vitro. The present invention further permits the development of protocols for treating diabetes as well as conditions such as β cell hyperplasia, nesidioblastosis and pancreatic cancer.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier, i.e. <400>1, <400>2, etc. A sequence listing is provided after the claims.

One aspect of the present invention contemplates a method of stimulating or otherwise facilitating formation of colonies of pancreatic cells containing insulin-secreting cells, said method comprising culturing pancreatic cells in the presence of a bone morphogenetic protein (BMP) or a functional derivative, homologue, mimetic, analogue or agonist thereof for a time and under conditions sufficient for colonies to form comprising insulin-secreting cells.

Another aspect of the present invention provides a method of stimulating or otherwise facilitating formation of colonies of pancreatic cells containing insulin-secreting cells, said method comprising culturing pancreatic cells in the presence of laminin-1 or laminin-1-containing extracellular matrix (ECM) or a functional derivative, homologue, mimetic, analogue or agonist thereof for a time and under conditions sufficient for colonies to form comprising insulin-secreting cells.

A further aspect of the present invention provides a method for stimulating or otherwise facilitating formation of colonies of pancreatic cells containing insulin-secreting cells, said method comprising culturing mammalian pancreatic cells in the presence of a BMP or a functional derivative, homologue, mimetic, analogue or agonist thereof and laminin-1 or laminin-1-containing ECM or a functional derivative, homologue, mimetic, analogue or agonist thereof for a time and under conditions sufficient for colonies to form comprising insulin-secreting cells.

Still another aspect of the present invention provides a method of stimulating or otherwise facilitating formation of cystic epithelial colonies containing insulin-secreting cells, said method comprising culturing pancreatic cells in the presence of one or both of a BMP or a functional derivative or homologue, mimetic, analogue or agonist thereof and laminin-1 or laminin-1-containing ECM or a functional derivative, homologue, mimetic, analogue or agonist thereof for a time and under conditions sufficient for colonies to form comprising insulin-secreting cells.

Yet another aspect of the present invention contemplates a method of stimulating or otherwise facilitating the formation of colonies of pancreatic cells containing insulin-secreting cells, said method comprising culturing pancreatic cells in the presence of a BMP selected from the group consisting of BMP 2, BMP 3, BMP 4, BMP 5, BMP 6 and BMP 7 or any other molecule having BMP properties or functional derivatives or homologues or mimetics or analogues or agonists thereof and laminin-1 or laminin-1-containing ECM or a functional derivative, homologue, mimetic, analogue or agonist thereof under time and conditions sufficient for colonies to form comprising insulin-secreting cells.

Even still another aspect of the present invention provides a method of stimulating or otherwise facilitating formation of colonies containing insulin-secreting cells from pancreatic cells, said method comprising culturing pancreatic cells in the presence of a BMP or a heterodimer formed from two or more BMPs or a functional derivative, homologue, mimetic, analogue or agonist forms thereof for a time and under conditions sufficient for colonies to form comprising insulin-secreting cells.

Even yet another aspect of the present invention is directed to a method of stimulating or otherwise facilitating formation of colonies containing insulin-secreting cells from pancreatic cells, said method comprising culturing pancreatic cells in the presence of a BMP or a heterodimer formed from two or more BMPs and laminin-1 or laminin-1-containing ECM or functional derivatives, homologues, mimetics, analogues or agonists thereof for a time and under conditions sufficient for colonies to form comprising insulin-secreting cells.

Another aspect of the present invention contemplates a method of treating comprising modulating the expression of one or more endogenous genetic sequences encoding a BMP to facilitate the formation of colonies of insulin-secreting cells.

A further aspect of the present invention contemplates a method for the treatment of a subject with type 1 diabetes or a related condition, said method comprising transplanting to said subject, insulin-secreting cells produced following the in vitro culture of pancreatic cells in the presence of a BMP or a heterodimer formed from two or more BMs or functional derivatives, homologues, mimetics, analogues or agonists thereof and optionally in the presence of laminin-1 or laminin-1-containing ECM or derivatives, homologues, mimetics, analogues or agonists thereof comprising insulin-secreting cells for at time and under conditions sufficient for colonies to form.

Still a further aspect of the present invention provides a method for the treatment or prophylaxis of islet/β cell hyperplasia adenoma or a related condition including pancreatic cancer, said method comprising administering to a subject an effective amount of an antagonist of a BMP for a time and under conditions sufficient to inhibit the formation or maintenance of insulin-producing β cells.

DETAILED DESCRIPTION OF THE PREFERRED EMBODIMENTS

Figure 1:
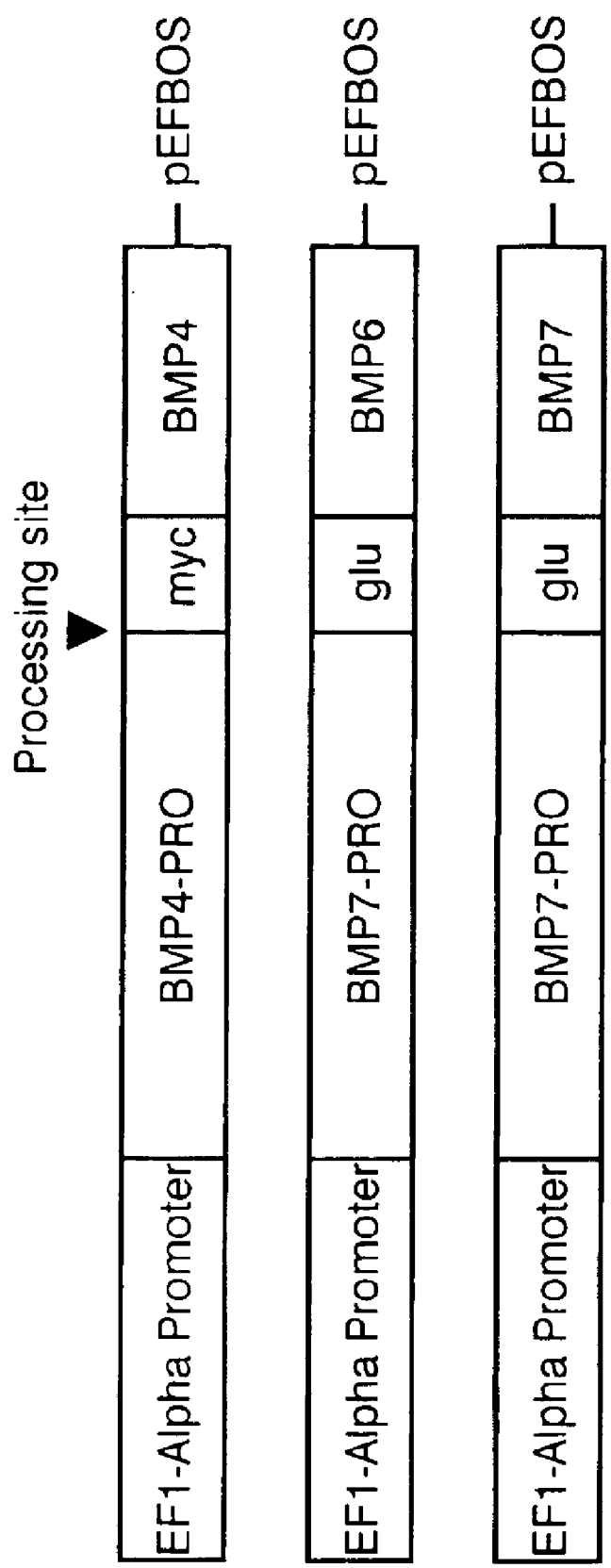
FIG. 1 is a schematic representation of BMP expression vectors showing the relative positions of the pro-domains, epitope tag (glu or myc) and the active peptide within the vector pEFBOS. The processing site at which proteolytic cleavage occurs to release the tagged active peptide is indicated. In addition to the vectors shown, other combinations of epitope, tag, pro-domain and active peptide were constructed.

In accordance with the present invention, the inventors have identified that certain BMP molecules are expressed in the developing pancreas and are capable of stimulating formation of insulin-positive cells. In a related embodiment, the inventors have identified that laminin-1 or laminin-1-containing extracellular matirx (ECM) also promotes formation of insulin-secreting cells.

Accordingly, one aspect of the present invention contemplates a method of stimulating or otherwise facilitating formation of colonies of pancreatic cells containing insulin-secreting cells, said method comprising culturing pancreatic cells in the presence of a bone morphogenetic protein (BMP) or a functional derivative, homologue, mimetic, analogue or agonist thereof for a time and under conditions sufficient for colonies to form comprising insulin-secreting cells.

In a related embodiment, the present invention provides a method for stimulating or otherwise facilitating formation of mammalian colonies of pancreatic cells containing insulin-secreting cells, said method comprising culturing pancreatic cells in the presence of laminin-1 or laminin-1-containing ECM or a functional derivative, homologue, mimetic, analogue or agonist thereof for a time and under conditions sufficient for colonies to form comprising insulin-secreting cells.

The term "pancreatic cells" is used herein in its broadest context to include any pancreatic or precursor cell which is acted upon by a BMP, generally but not exclusively in the presence of laminin-1. Examples of such cells include progenitor cells, stem cells, duct cells or any other cell precursor. Reference to "progenitor cells" and "stem cells" includes any embryonic stem (ES) cell committed to a pancreatic cell lineage. All such cell types are encompassed by the term "pancreatic cells" or "pancreatic cell". Preferred pancreatic cells are of human, primate, livestock or laboratory test animal origin. Most preferred cells are of human origin. Reference herein to a "subject" includes reference to a mammal and in particular a human.

In accordance with the present invention, the cell culture conditions necessary to promote the formation of colonies comprising insulin-producing cells from pancreatic cells include the presence of an ECM at concentrations suitable to promote the formation of colonies of pancreatic cells expressing insulin. It is preferable that the extracellular protein of the present invention is laminin-1. Generally but not exclusively the extra laminin-1 may be added to a cell culture medium from about 1 βg/ml to about 1000 μg/ml or more preferably from about 10 μg/ml to about 500 μg/ml or even more preferably from about 50 μg/ml to about 500 μg/ml to stimulate the formation of cystic colonies containing insulin positive cells. Although it preferable that ECM of the present invention is laminin-1 the present invention further contemplates the use of laminin-1, and its functional derivatives, homologues, mimetics or analogues including recombinant peptides, polypeptides and proteins that comprises a laminin-1 derived amino acid sequence.

Another aspect of the present invention contemplates a method for stimulating or otherwise facilitating formation of colonies of pancreatic cells containing insulin-secreting cells, said method comprising culturing pancreatic cells in the presence of laminin-1 or a laminin-1-containing ECM or a functional derivative, homologue, mimetic, analogue or agonist thereof, and a BMP or a functional derivative or homologue, mimetic, analogue or agonist thereof for a time and under conditions sufficient for colonies to form comprising insulin-secreting cells.

In still another aspect, the present invention provides a method of stimulating or otherwise facilitating formation of cystic epithelial colonies containing insulin-secreting cells, said method comprising culturing pancreatic cells in the presence of laminin-1 or a laminin-1-containing ECM or a functional derivative, homologue, mimetic, analogue or agonist thereof, and a BMP or a functional derivative or homologue, mimetic, analogue or agonist thereof for a time and under conditions sufficient for colonies to form comprising insulin-secreting cells.

Reference herein to a "bone morphogenetic protein" or "BMP" or a specific BMP such as but not limited to "BMP 2", "BMP 3", "BMP 4", "BMP 5", "BMP 6" and "BMP 7" includes reference to a polypeptide having BMP properties including the ability to stimulate or otherwise facilitate the formation of insulin-secreting cells. BMPs contemplated herein are those belonging to the TGF-β family of molecules. These terms also encompass functional derivatives, homologues, mimetics and analogues of the BMP molecule including homodimeric and heterodimeric forms. A derivative of a BMP is a mutant, part, portion or fragment including a BMP carrying a single or multiple amino acid substitution, addition and/or deletion to its amino acid sequence. Such derivatives, homologues, mimetics and analogues are considered functional in that they are capable of stimulating or otherwise facilitating formation of insulin-secreting cells. A derivative may also include an agonist or antagonist. An antagonist is particularly useful in the treatment or prevention of islet/cell hyperplasia/adenoma which causes the clinical syndrome of hyperinsulinemic hypoglycemia. Antagonists of some BMPs such as BMP 7 are particularly useful for the treatment of nesidioblatosis and other β cell hyperplasias such as hyperinsulinemia or hyperglycemic syndrome of infancy, β cell tumors (insulinomas) and/or pancreatic cancer (carcinoma) in mammals and in particular humans.

The present invention encompasses agonists and antagonists, even if they are not derivatives of a BMP. Antagonists may, for example, be chemical molecules identified from a chemical library or identified from natural product screening or may be secreted antagonists such as those which inhibit the signalling pathway of a BMP. Useful antagonists include Activin A and/or TGF-β or their homologues or derivatives.

In one aspect of the present invention, it is preferable that a BMP or combination of BMPs and/or laminin-1 or laminin-1-containing ECM alone or laminin-1 or laminin-1-containing ECM and a BMP are present in a culture of pancreatic cells to facilitate the formation of cystic epithelial colonies containing insulin-producing β cells. It is further contemplated that the concentration of the BMPs present in a culture of pancreatic cells may be modulated such that the cell culture is exposed to a regimen of BMPs and laminin-1 or laminin-1-containing ECM to stimulate the production of insulin-producing cells. In this regard, any BMP may be used which have BMP properties for stimulating the formation of insulin-producing cells. The BMPs may be used either individually or together with each other or with any other member of the BMP family for the purpose stimulating the formation of insulin-producing cells. Specific BMPs contemplated herein include BMP 2, BMP 3, BMP 4, BMP 5, BMP 6 and BMP 7 or heterodimers thereof or any BMP member of the TGF-β family.

In yet a further related embodiment, the present invention contemplates a method of stimulating or otherwise facilitating the formation of colonies of pancreatic cells containing insulin-secreting cells, said method comprising culturing pancreatic cells in the presence of laminin-1 or laminin-1-containing ECM or a functional derivative, homologue, mimetic, analogue or agonist thereof and a BMP selected from the group consisting of BMP 2, BMP 3, BMP 4, BMP 5, BMP 6 and BMP 7 or functional derivatives or homologues or mimetics or analogues or agonists thereof under time and conditions sufficient for colonies to form comprising insulin-secreting cells.

The nucleotide and amino acid sequences for a range of BMP monomers are listed in the sequence listing. A summary of the sequence listing is shown just prior to the Examples. The present invention is not to be limited to the BMPs exemplified.

Other derivatives contemplated by the present invention include a range of glycosylation variants from a completely unglycosylated molecule to a modified glycosylated molecule. Altered glycosylation patterns may result from expression of recombinant molecules in different host cells.

A homologue of a BMP includes a structurally or functionally related BMP from another species or from within the same species and includes a polymorphic variant.

Analogues of the BMP molecules contemplated herein include, but are not limited to, modifications to side chains, incorporation of unnatural amino acids and/or their derivatives during peptide, polypeptide or protein synthesis and the use of crosslinkers and other methods which impose conformational constraints on the proteinaceous molecule or its analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilize BMPs for use in in vitro culture or as a therapeutic agent.

Preferably, the BMP is in recombinant form. The recombinant form of the BMP may comprise the identical amino acid sequence of the naturally occurring BMP or it may contain one or more amino acid substitutions, additions and/or deletions including a deletion of the start methionine. A nucleotide sequence encoding a BMP may also be optimized for expression in a particular host cell. This may result in a change in the amino acid sequence such as the inclusion of a cleavage site.

Generally, the origin of BMP is the same as the origin of the pancreatic cells. For example, human-derived recombinant BMP is preferably used on human pancreatic cells. However, the present invention extends to "humanized" forms of non-human derived BMP molecules. A humanized murine BMP, for example, comprises a murine BMP backbone with amino acid substitutions, additions and/or deletions to render the molecule functionally, structurally and/or antigenically similar to a human BMP.

The recombinant BMP molecules may also comprise homo- or heterodimeric forms. A heterodimer may comprise monomers from different BMPs from the same species or different monomers from different specimens. BMPs of heterodimers include dimers between BMP4 and BMP 5, BMP4 and BMP6, BMP4 and BMP7,BMP2 and BMP 5, BMP 2 and BMP 6, BMP 2 and BMP 7, BMP 6 and BMP 7 and BMP 5 and BMP 6 amongst others. A BMP for use in a human subject is preferably of human origin or is a humaized form of a non-human form of BMP.

A "functional" BMP derivative, homologue, mimetic or analogue retains the ability to stimulate or otherwise facilitate the development of insulin-secreting cells in vitro. The "ability", however, may be more or less than a "parent" BMP.

Accordingly, another aspect of the present invention provides a method of stimulating or otherwise facilitating formation of colonies containing insulin-secreting cells from pancreatic cells, said method comprising culturing pancreatic cells in the presence of a BMP or a heterodimer formed from two or more BMPs or functional derivatives, homologues, mimetics, analogues or agonists forms thereof for a time and under conditions sufficient for colonies to form comprising insulin-secreting cells.

In a preferred embodiment, the cells are cultured in the presence of both a BMP and a differentiation inducer such as but not limited to laminin-1 or a laminin-1 -containing ECM or its functional derivatives, homologues, mimetics, analogues or agonists. A functional laminin-1 derivative, homologue, mimetic or analogue is a molecule which is capable of inducing the production of insulin-secreting cells in the presence of a BMP.

More particularly, the present invention is directed to a method of stimulating or otherwise facilitating formation of colonies containing insulin-secreting cells from pancreatic cells, said method comprising culturing pancreatic cells in the presence of a BMP such as BMP 2, BMP 3, BMP 4, BMP 5 and/or BMP 6 or a heterodimer formed from two or more BMPs and laminin-1 or a laminin-1-containing ECM or functional derivatives, homologues, mimetics, analogues or agonists thereof for a time and under conditions sufficient for colonies to form comprising insulin-secreting cells.

A further aspect of the present invention contemplates the modulation of the expression of endogenous BMPs in order to facilitate the formation of colonies of insulin-secreting cells. In this aspect of the present invention, agonists are used to modulate the expression of genetic sequences encoding BMPs. Such agonist of bone morphogenetic gene expression may be small molecule agonists such as peptides polypeptides or proteins. The agonist of BMP expression may be added to a culture medium in which cells are contained or be transferred directly to pancreatic cells by means such as but not limited to transfection.

Accordingly, this aspect of the present invention provides a method for the in vivo modulation of BMP expression, said method comprising culturing pancreatic cells in the presence of an agonist of a BMP, wherein the agonist stimulates the expression of a BMP gene selected from the group of BMP 2, BMP 3, BMP 4, BMP 5, BMP 6, BMP 7 wherein the agonist can promote the formation of a heteromeric form of two or more BMPs.

The BMP and laminin-1 may co-exist in the culture medium or may be sequentially added in either order. Sequential addition includes a time differential of from seconds or minutes to hours or days.

It is proposed in accordance with the present invention that cells generated in vitro are then transplanted to subjects with type 1 diabetes or a related condition. Generally, the transplantation process requires appropriate treatment to prevent recurrent autoimmunity and/or immune-mediated rejection. A related condition to type 1 diabetes includes any condition resulting in a lack of insulin following destruction of pancreatic islet cells. Reference to "type 1 diabetes" means insulin dependent type 1 diabetes or a related condition.

Generally BMP gene expression is required for pancreatic epithelial cell development, and in particular for the development of insulin-secreting cells. In this aspect of the invention, some members of the transforming growth factor (TGF)-β1 superfamily antagonize the formation of colonies of insulin-secreting cells. In particular, TGF-β1 and Activin A antagonize the formation of colonies of insulin forming cells. Thus, in this aspect of the present invention the antagonistic activity of TGF-β1 and Activin A in relation to the development of insulin-secreting cells may be alleviated by the addition of antagonist of TGF-β1 and Activin A permitting the formation of colonies of insulin-secreting cells.

Accordingly, this embodiment of the present invention provides a method of stimulating or otherwise facilitating formation of colonies containing insulin-secreting cells from pancreatic cells, said method comprising culturing pancreatic cells in the presence of a BMP and in the presence of an antagonist of Activin A or TGF-β1.

The term "antagonize" means and includes reducing inhibiting, or otherwise adversely affecting the normal function or activity of a molecule or molecules or agent or agents. In this regard, the functional result of such antagonism of Activin A or TGF-β1 is the inability or at least a reduced capacity of Activin A or TGF-β1 to inhibit the development insulin-producing cells from pancreatic cells, particularly in the presence of BMPs.

In accordance with this aspect of the present invention, there is provided a method of stimulating or otherwise facilitating the formation of colonies containing insulin-secreting cells from pancreatic cells, said method comprising culturing pancreatic cells in the presence of a BMP or a heterodimer formed from two or more BMPs or a functional derivative, homologue, mimetic, analogue or agonist forms thereof and an antagonist of Activin A or TGF-β1 for a time and under conditions sufficient for colonies to form comprising insulin-secreting cells.

Another aspect of the present invention contemplates a method for the treatment of a subject with type 1 diabetes or a related condition, said method comprising transplanting to said subject insulin-secreting cells produced following the in vitro culture of pancreatic cells in the presence of a BMP or a heterodimer formed from two or more BMPs or functional derivatives, homologues, mimetics, analogues or agonists thereof and optionally in the presence of laminin-1 or laminin-1-containing ECM or derivatives, homologues, mimetics, analogues or agonists thereof for at time and under conditions sufficient for colonies to form comprising insulin-secreting cells.

An antagonist of Activin A or TGF-β1 may be a peptide, polypeptide, protein, antibody, small or large chemical entities or combinations thereof and may be in isolated naturally occurring form or may be in a recombinant or chemically synthetic form Screening for antagonists may be accomplished in any number of ways. In one method for the identification of an antagonist of Activin A or TGF-β1, pancreatic cells are incubated in the presence of a BMP and an inhibitory concentration of Activin A or TGF-β1 and subjected to exposure by a potential antagonist. An immunoassay may be used to assay treated cells for the presence of insulin-producing cells.

There are many variations to assays for the screening agonists and antagonists and all are encompassed by the present invention.

In a related embodiment, the present invention provides a method for the modulation (e.g. reduction) of Activin A and TGF-β1 mRNA levels in the pancreatic tissue of individuals suffering from type 1 diabetes, said method comprising the administration of a therapeutic quantity of a sense or an antisense oligonucleotide or modified sense or antisense oligonucleotide complementary to an Activin A and TGF-β1 mRNA over time and under conditions such that Activin A and TGF-β1 mRNA levels are modified (e.g. reduced).

In a further related aspect, the present invention contemplates a method for reduction of expression of Activin A and TGF-β1 mRNA, said method comprising the administration of a therapeutic quantity of an antisense oligonucleotide or modified antisense oligonucleotide complementary to regulatory regions of the Activin A and TGF-β1 mRNA such as but not limited to 5' untranslated regions, 3' untranslated regions, introns or other polynucleotide sequences required for the expression of mRNA.

In yet a further related embodiment, the present invention provides a method for stimulating or otherwise facilitating the formation of colonies containing insulin-secreting cells from pancreatic cells in pancreatic tissues of an individual with type 1 diabetes, said method comprising the administration of a therapeutic quantity of an antisense oligonucleotide complementary to an Activin A or TGF-β1 mRNA capable of hybridizing to an Activin A or TGF-β1 mRNA and using means provided by the biological system to reduce the level of Activin A or TGF-β1 mRNA levels.

Another aspect of the present invention provides a method for modulating the quantity of mRNA transcribed by an endogenous form of the human Activin A or TGF-β1 mRNA gene, said method comprising the construction of polynucleotide sequences for the expression of an antisense polynucleotide sequence complementary to the regulatory regions of Activin A or TGF-β1 mRNA gene, wherein expression of the antisense polynucleotide sequence permits the expression of the antisense oligonucleotide in pancreatic cells facilitating the formation of colonies containing insulin-secreting cells.

As used herein, the term "antisense oligonucleotide" describes a sequence of nucleotides to form a polynucleotide that is complementary to a given target polynucleotide sequence. The antisense oligonucleotide may be complementary to an entire given sequence of a polynucleotide or may be complementary to a region of the polynucleotide sequence. An antisense polynucleotide may be any length and hybridizes to a sequence under particular stringency conditions and may be produced so that it will hybridize to a complementary polynucleotide sequence only under certain hybridiziation conditions. Antisense molecules may be constructed such that they hybridize selectively under physiological conditions. Selective hybridization under physiological conditions requires that the antisense oligonucleotide should comprise at least 10 contiguous nucleotides which are complementary to the target polynucleotide sequence and in some instances it maybe required that the complementarity of an antisense molecule may be interrupted by a sequence of one or more nucleotides in length, such nucleotide sequences may hybridize to their target sequences under specified conditions.

The term "modified oligonucleotide" as used herein describes an oligonucleotide that has at least two nucleotide elements covalently linked by a phosphodiester linkage between the 5' end of one nucleotide and the 3' end of the other nucleotide and a chemical group not normally associated with nucleic acids covalently linked to the polynucleotide. Preferred synthetic internucleotide linkages include but are not limited to phosphorothioates, alkyl phosphonates, phosphorodithioates, alklphosphonates, phosphorodithioates, phosphate esters, alklyphosphonates, carbamates, phosphate triesters, acetamides and carboxymethyl esters. The term "modified oligonucleotide" also encompasses oligonucleotides with a convalently modified base and or sugar. Modified nucleosides include but are not limited to covalently attached molecules other than a hydroxyl group at the 3' position and other than a phosphate group at the 5' position. Thus, modified oligonucleotides may include a 2'-O-alkylated ribose group. In addition, a modified oligonucleotide may comprise sugars such as but not limited to arabinose or ribose. A modified oligonucleotide includes a C5 propyne modification.

Generally, the pancreatic cells cultured in vitro are not from the subject being treated. The term "pancreatic cells" is as described above. Any source of pancreatic cells may be used. One particularly useful source is fetal pancreas cells.

A further aspect of the present invention provides for the use of a BMP or a heterodimer formed from two or more BMPs in the manufacture of an agent for use in stimulating or otherwise facilitating formation of colonies of insulin-secreting cells from pancreatic cells following in vitro culture of said pancreatic cells.

In an alternative embodiment, the BMP is administered to a subject with type 1 diabetes or a related condition in order to stimulate the proliferation and differentiation of cells and to thereby restore insulin secretion in the host pancreas.

Accordingly, the present invention contemplates a method for the treatment of a subject with type 1 diabetes or a related condition, said method comprising administering to said subject an effective amount of a BMP or a heterodimer formed from two or more BMPs or derivatives, homologues, mimetics, analogues and/or agonists thereof for a time and under conditions sufficient to facilitate insulin secretion in the pancreas of said subject.

Generally, the time of conditions for administration of the BMP are such to permit stimulation of the proliferation and differentiation of pancreatic cells into insulin-secreting β cells. Generally, reference to "facilitating" insulin secretion includes initiating, enhancing, promoting or inducing insulin secretion.

The BMP may be administered alone or in combination with other agents such as laminin-1 and/or immune suppressive agents. In addition to laminin-1, other agents include cytokines, interferons and interleukins as well as laminin-1-containing ECM.

Accordingly, the present invention further provides a composition comprising a BMP or a heterodimer formed from two or more BMPs and optionally one or more other therapeutic agents and one or more pharmaceutically acceptable carriers and/or diluents.

The composition is for use in stimulating proliferation and differentiation of pancreatic cells into insulin-secreting β cells. The term "for use" in this context also means "when used" for this purpose.

The composition according to this aspect of the present invention may be referred to as a "pharmaceutical composition".

The preparation of pharmaceutical compositions is well known in the art and reference can conveniently be made to Remington's Pharmaceutical Sciences, Mack Publishing, Company, Easton, Pa., USA.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients including therapeutic agents can also be incorporated into the compositions. In one embodiment, laminin-1 is also included in the composition.

Alternatively or in addition, anti-$\alpha_6$ integrin antibody, GoH3, is included. Alternatively, or in addition to, the component is an agent capable of inhibiting P13K, MAP kinase or actin polymerization. This is predicated on the observation that blocking laminin-1 binding to $\alpha_6$ integrin receptors by the monoclonal antibody GoH3 or inhibiting P13K, MAP kinase or actin polymerizatin downstream of $\alpha_6$ integrins abolished cell division and significantly increased β cell number in fetal mouse pancreas cell cultures. These findings suggest that the $\alpha_6$ integrins normally mediate a proliferative signal from laminin-1 through the MAP kinase pathway and exert an inhibitory effect on β cell survival and cell differentiation.

Administration may be by any number of means including intravenous, intraperitoneal, subcutaneous, intranasal, intrapharyngeal, intrabronchial, oral or rectal administration. The composition may be in a liquid, solid or gas or vapour form. Administration may be by pump, injection, tablet or via aerosol means. Delivery may also be "on-site" such as during surgery, biopsy or other interventionist therapy. Targeted delivery may also be accomplished.

The effective amount of BMP includes an amount in the range of from about 10 µg/kg body weight to about 1 mg/kg body weight or from about 100 µg/kg body weight to about 500 µg/kg body weight. Expressed alternatively, the effective amounts are preferably in the order of 0.5–100 mg/per dose/subject.

In a further embodiment, the present invention provides a two part pharmaceutical pack comprising a first compartment comprising a BMP or a functional derivative, homologue, mimetic or analogue thereof at a second compartment comprising laminin-1 or laminin-1-containing ECM or a functional derivative, homologue, mimetic or analogue thereof.

In one embodiment, the contents of both compartments are mixed together prior to use or are prepared separately and administered simultaneously or sequentially.

The above-mentioned pharmaceutical pack may further comprise instructions for use.

In an additional embodiment, the method may be practised by administering DNA encoding the BMP. The DNA may be cDNA or genomic DNA or is a DNA:RNA hybrid.

In still yet another embodiment, the present invention extends to the use of a BMP or a heterodimer formed from two or more BMPs in the manufacture of a medicament in the treatment of type 1 diabetes or a related condition in a subject.

The treatment protocol proposed herein may be extended to people genetically at risk from developing type 1 diabetes or a related condition or who are at risk for non-genetic reasons such as age. Accordingly, the present invention extends to the treatment and/or prophylaxis of type 1 diabetes or a related condition.

In yet another embodiment, an antagonist of a BMP is used in the manufacture of a medicament for the treatment or prophylaxis of islet/β cell hyperplasia/adenoma which causes the clinical syndrome of hyperinsulinemic hypoglycemia or other related condition.

Accordingly, another aspect of the present invention contemplates a method for the treatment or prophylaxis of islet/β cell hyperplasia adenoma or a related condition including pancreatic cancer, said method comprising administering to a subject an effective amount of an antagonist of a BMP for a time and under conditions sufficient to inhibit the formation or maintenance of insulin-producing β cells. Preferably, the antagonist is an antagonist of a BMP such as BMP 7 and the condition is nesidioblastosis. An antagonist may be a derivative of a BMP or it may be, for example, identified following screening of a natural product or chemical library.

Aspects of this invention are described in Jiang et al. (1999) which is incorporated herein by reference. This article describes the development of a low cell density serum-free culture system for dissociated pancreatic cells from the 13.5-day mouse fetus and investigated the effects of extracellular matrix proteins on differentiation of islet β cells. After four days in culture, total cell number decreased by two-thirds, but insulin-positive cell number increased 10-fold. Both of collagens I and IV inhibited β cell survival (by >50%), whereas fibronectin had no effect. In the presence of soluble laminin-1, however, the number of β cells increased linearly by 60-fold without an increase in the total cell number; glucagon-positive cell number was unchanged, and somatostatin and pancreatic polypeptide-positive β cells were not detected. The effect of laminin-1 was completely blocked by a monoclonal rat anti-laminin-1 antibody. In the presence of laminin-1, the thymidine analogue BrdU, was incorporated into only 2.5% of cells, which were mainly insulin-negative at days 1–3. Laminin-1 appeared, therefore, to induce differentiation of cells from precursor cells in day 13.5 fetal pancreas. Laminin-1 was shown to be expressed in the epithelial basement membrane of the 13.5 to 17.5 day fetal pancreas. These findings show a role for laminin-1 in promoting differentiation of pancreatic β cells.

The present invention is further described by the following non-limiting Examples.

| SUMMARY OF SEQUENCE LISTING | |
|---|---|
| DESCRIPTION | SEQUENCE IDENTIFIER |
| BMP 4/4 glu: nucleotide | <400>1 |
| BMP 4/4 glu: amino acid | <400>2 |
| BMP 4/6 glu: nucleotide | <400>3 |
| BMP 4/6 glu: amino acid | <400>4 |
| BMP 4/6 myc: nucleotide | <400>5 |
| BMP 4/6 myc: amino acid | <400>6 |
| BMP 7/6 glu: nucleotide | <400>7 |
| BMP 7/6 glu: amino acid | <400>8 |
| BMP 7/6 myc: nucleotide | <400>9 |
| BMP 7/6 myc: amino acid | <400>10 |
| BMP 7/7 glu: nucleotide | <400>11 |
| BMP 7/7 glu: amino acid | <400>12 |
| BMP 7/7 myc: nucleotide | <400>13 |
| BMP 7/7 myc: amino acid | <400>14 |
| BMP 2 forward primer | <400>15 |
| BMP 2 reverse primer | <400>16 |
| BMP 4 forward primer | <400>17 |
| BMP 4 reverse primer | <400>18 |
| BMP 5 forward primer | <400>19 |
| BMP 5 reverse primer | <400>20 |
| BMP 6 forward primer | <400>21 |
| BMP 6 reverse primer | <400>22 |
| BMP 7 forward primer | <400>23 |
| BMP 7 reverse primer | <400>24 |
| TGFβ-1 forward primer | <400>25 |
| TGFβ-1 reverse primer | <400>26 |
| Activin A forward primer | <400>27 |
| Activin A reverse primer | <400>28 |
| β actin forward primer | <400>29 |
| β actin reverse primer | <400>30 |

BMP = bone morphogenetic protein
BMP 4/4 = BMP 4 homodimer
BMP 7/7 = BMP 7 homodimer
BMP 4/6 = BMP 4 and BMP 6 heterodimer
BMP 4/7 = BMP 4 and BMP 7 heterodimer

EXAMPLE 1

Cloning and Expression of Mouse BMP

The coding sequences of BMPs 3, 4, 6 and 7 were amplified from a 7 dpc mouse cDNA library by a PCR-based approach. This yielded two fragments for BMP 4 and BMP 7, representing the pro-domain and active peptide (cystine knot). For BMP 6 and BMP 3, only the active peptide region was amplified. The PCR products were cloned into pGEM T-easy and the nucleotide sequences determined. Individual clones containing inserts which possessed only the consensus sequence for each fragment were then selected. The inserts representing the pro-domains of BMP 4 and 7 were excised from these clones with MluI and the isolated fragments ligated into the AscI site of pEFBOS myc or pEFBOS glu/glu. Recombinant plasmids resulting from this ligation contained the pro-domain N-terminal to the epitope tag (myc or glu). These plasmids were subsequently digested with MluI and ligated to MluI fragments representing the active peptides to yield a series of vectors (FIG. 1). Restriction mapping and sequence analysis was then used to verify the correct configuration of the resultant recombinants.

EXAMPLE 2

BMP-producing CHO Cell Lines

Figure 2:
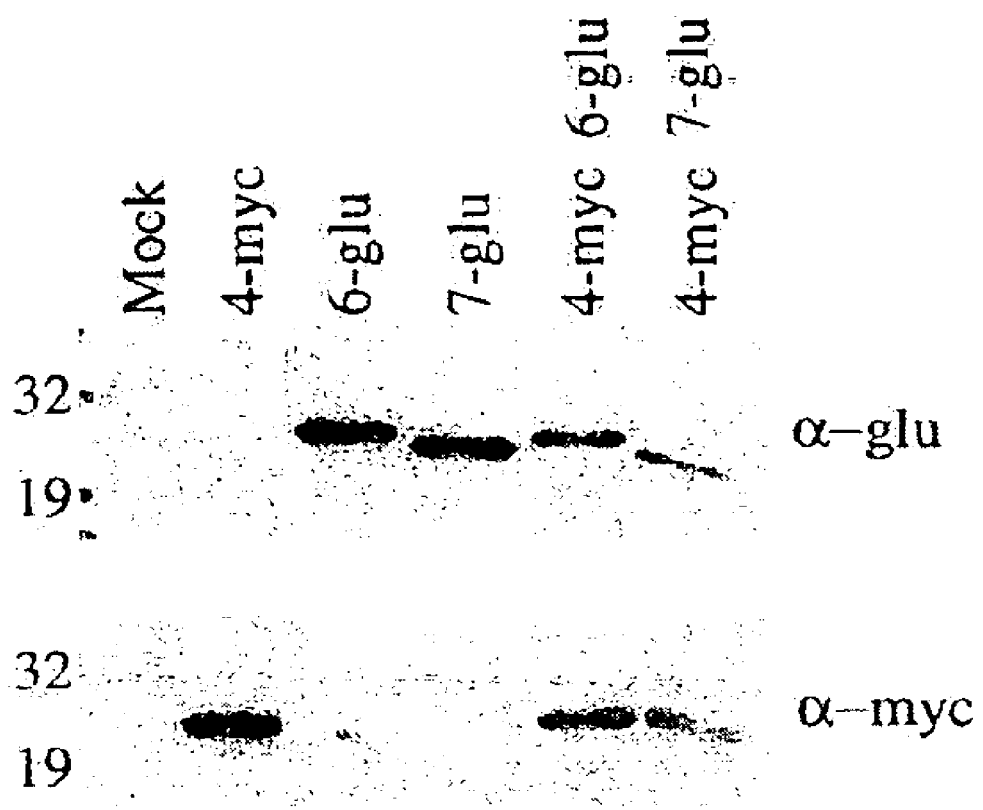
FIG. 2 is a photographic representation of Western blot analysis of conditioned media from COS cells transfected with pEFBOS constructs encoding myc tagged BMP 4 (4-myc), glu/glu tagged BMP 6 (6-glu), glu/glu tagged BMP 7 (7-glu) or combinations thereof Approximately 20 μl of medium was subjected to SDS-PAGE and the separated sample electrotransferred to filter membrane. The filters were blocked with 0.1% w/v BSA in PBS and incubated with mouse anti-myc or anti-glu/glu antibody. Bound antibody was visualized with peroxidase-conjugated anti-mouse Ig ECL (Amersham) detection kit. The position and size (in kD) of the molecular weight markers is shown on the left of each panel and antibody used for detection shown on the right. The proteins encoded by the constructs used to transfect the COS cells are indicated above.
Figure 3:
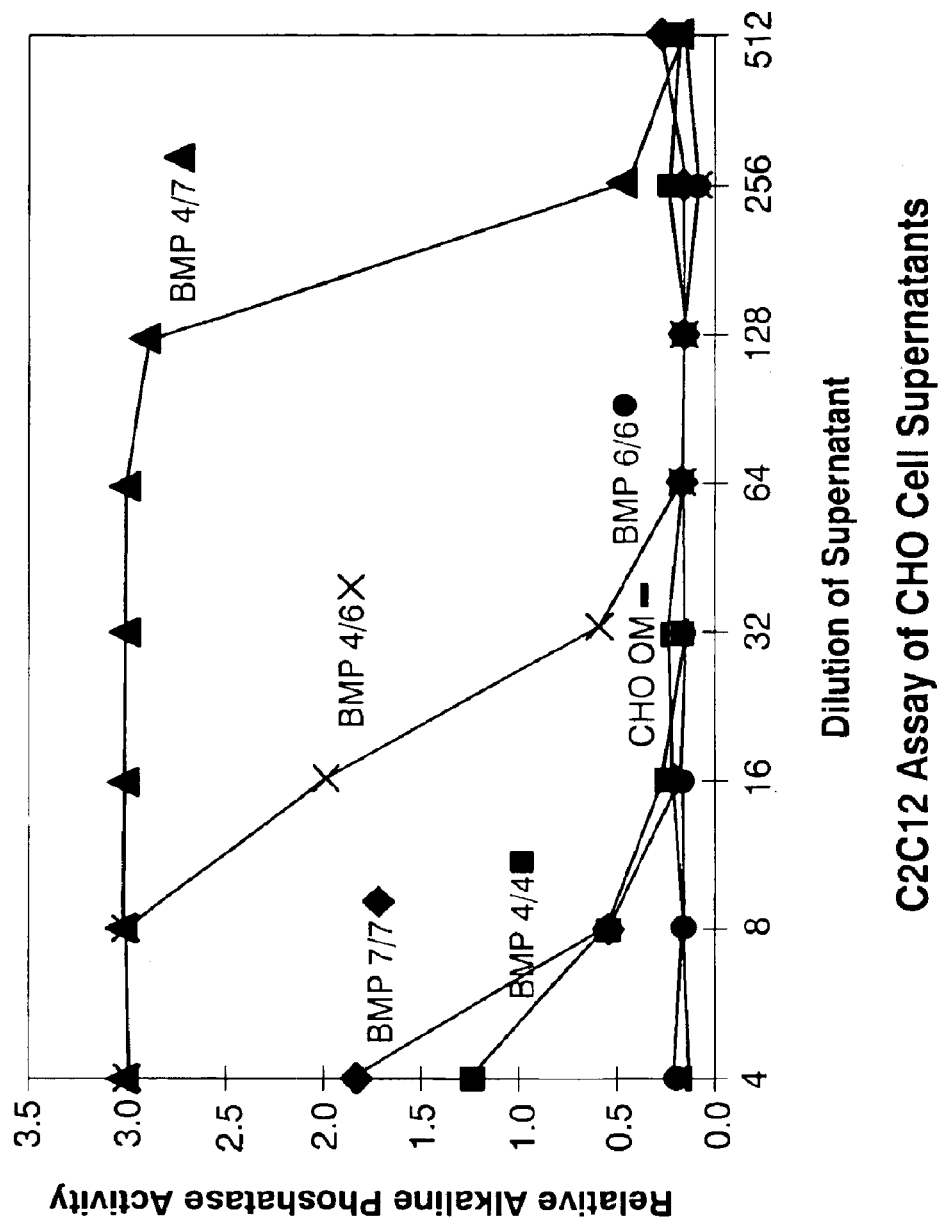
FIG. 3 is a graphical representation of BMP-induced osteoblast transformation (alkaline phosphatase activity) of C2C12 myoblast cells.

Transient transfections in COS cells were evaluated by immunoblotting (FIG. 2) to confirm that the vectors encoded proteins of the correct size, with BMP activity (see below). In order to secure a more reliable source of these factors, the inventors established CHO cell lines stably transfected with the vectors in the presence of a plasmid encoding puromycin resistance. Approximately 20 puromycin-resistant clones representing each vector type were isolated and conditioned medium from each clone was bioassayed for BMP activity to identify the highest producer cell line for each transfection. Media from cells expressing BMPs 4/4, 7/7, 4/6 and 4/7 contained significant activity, compared to medium conditioned to untransfected CHO cells (FIG. 3). Expression of BMP 3 has not yet been assayed. In the case of BMP 6, significant BMP activity was never detected so cell lines were selected on the basis of the level of myc epitope tagged protein in conditioned media.

EXAMPLE 3

BMP Bioassay

BMP activity was measured in the C2C12 cell bioassay, in which BMPs transform C2C12 myoblasts into alkaline phosphatase-containing osteoblasts (Katagiri et al., 1994). Briefly, CHO cells were plated at a density of around $5 \times 10^6$ per 75 $cm^2$ flask in serum-free HYBRIDOMA medium (Gibco BRL Life Technology) (SFHM) containing 10% v/v FCS. Once the cells had reached confluency, the medium was removed, the cells washed twice with SFHM and 10 ml of SFHM then added to each flask. The cells were cultured for four days and the conditioned medium collected, filtered through a 2 micron filter and stored at 4° C.

$2 \times 10^3$ C2C12 cells were plated into each well of a 96-well tissue culture plate in DME/10% v/v FCS. Twenty-four hours later, the medium was removed and replaced with 100 $\mu$l SFHM/1% v/v FCS. 50 $\mu$l of each conditioned medium was added in duplicate to the top row of the 96-well plate and the volume of these wells then made up to 200 $\mu$l. Using a multi-channel pipette, 100 $\mu$l from each well was then serially transferred to subsequent rows thus diluting the conditioned medium 2-fold with each transfer. After incubation for five days, the media were discarded and the cells washed with normal saline. Cells were lysed for 10 mins at room temperature (RT) in 100 $\mu$l 0.5% v/v TritonX-100 and 100 mM diethanolamine (pH 9.5) in normal saline. To each well was then added an aqueous solution containing 10 mM diethanolamine, 1 mg/ml p-nitrophenyl phosphate (PNPP) and 0.5 mM $MgCl_2$. The yellow reaction product catalyzed by alkaline phosphatase was allowed to develop for 10–60 mins before reading absorption at 415 nm.

EXAMPLE 4

Preparation and Culture of Fetal Mouse Pancreatic Cells

Dissociated fetal pancreas cells were prepared from 13.5 dpc CBA mice. Pregnant mice at 13.5 dpc were killed by cervical dislocation and fetuses collected into ice cold sterile mouse tonicity phosphate-buffered saline (MTPBS). Fetal pancreata were harvested under an Olympus dissection microscope into RPMI 1640 medium and dissociated in a shaking water bath at 37° C. for 11 mins in $Ca^{2+}/Mg^{2+}$-free PBS containing 0.5% v/v trypsin/EDTA as described for testis by Bucci et al. (1986). After dissociation, trypsin was inactivated by addition of 8% w/v bovine serum albumin (BSA, fraction V) (Sigma, St. Louis, USA). The tissue was aspirated several times in a pipette, passed through a 27 gauge needle to make a single cell suspension and then rinsed in 10 $\mu$g/ml DNAse I (Promega, Madison, USA) in RPMI 1640 for 10 mins to reduce cellular aggregates. Cell suspensions were filtered through a 70–100 $\mu$m steel mesh, centrifuged at 400×g for 5 mins and the supernatant discarded. The cell pellet was resuspended in HYBRIDOMA medium and stored on ice. Cells were counted under a haemocytometer and viability was determined by exclusion of 0.2% v/v trypan blue dye. Pancreatic cells were plated in 8 chamber slides (Nunc) at $1.5 \times 10^4$ cells/well in 0.3 ml HYBRIDOMA medium 500 UI/ml penicillin and 500 $\mu$g/ml streptomycin. The cells were cultured in 10% v/v $CO_2$, 90% v/v air at 37° C. with 100% humidity for four days in the presence of factors such as laminin-1 and BMPs.

EXAMPLE 5

Laminin-1

Laminin-1, prepared from murine Englebreth-Holm-Swarm (EHS) tumour cell basement membrane was purchased from Gibco BRL. To prevent polymerization, it was manipulated at 4° C., dialyzed at 4° C. against HYBRIDOMA medium and diluted directly into chilled medium before addition to pancreas cells in culture.

EXAMPLE 6

Antibodies

Guinea pig anti-porcine insulin antiserum was from Chemicon. Mouse monoclonal anti-bromodeoxyuridine (BrdU) IgG2a (Clone BU-1) was from Amersham Life Science. Rabbit antisera to porcine glucagon, human somatostatin and human pancreatic polypeptide were from Dako.

Rat monoclonal antibody (clone NKI-GoH3, IgG2a) that specifically blocks laminin-1 binding to $\alpha_6$ integrins (Sonnenberg et al., 1990; Almeida et al., 1995; Falk et al., 1996) was from Chemicon International (Temucula, USA). Goat polyclonal immunoglobulin to $\alpha_6$ (clone P1B5) and integrin $\beta_4$ (clone 3E1) were from Gibco BRL. Mouse monoclonal IgM antibody to $\alpha$-DG, IIH6, was provided as hybridoma supernatant from Howard Hughes Medical Institute, University of Iowa, College of Medicine (Iowa City, USA). The total protein concentration of IIH6 hybridoma supernatant was measured by the Bradford method (Bio-Rad, Hercules, USA). A non-blocking mouse monoclonal antibody to $\alpha$-DG (clone V1A4-1) was from Upstate Biotech (Lake Placid, USA). Rat monoclonal IgG2a (control for NKl-GoH3), mouse IgM (control for IIH6) and rat monoclonal IgG2a to integrin $\beta_1$ (clone 9EG7) from Pharmingen (San Diego, USA) were dialyzed against HYBRIDOMA medium at 4° C. prior to use. Guinea pig antiserum to porcine insulin was from Dako (Glostrup, Denmark). Mouse monoclonal IgG2a to BrdU (clone BU-1) was from Amersham Life Science (Buckinghamshire, England). Rabbit antiserum to porcine glucagon and to human somatostatin and pancreatic polypeptide were from Dako. Fractionated rabbit antiserum to human α-amylase, a marker of acinar cells, and to laminin, were from Sigma Chemicals (St. Louis, USA).

Heparin, a known blocker of laminin-1 binding to α-DG (Ervasti and Campbell, 1993; Pall et al., 1996) was from Sigma. Wormannin and Ly294002, inhibitors of P13K (Powis et al., 1994; Vlahos et al., 1994), genistein and herbimycin, inhibitors of Src family tyrosine kinases (Uehara et al., 1986) associated with focal adhesion kinase (FAK) (reviewed by Clarke and Brugge, 1995; Ilic et al., 1997), and PD98059, an inhibitor of MEK1 (Dudley et al., 1995) were from Calbiochem (La Jolla, USA). Cytochalasin D, an inhibitor of actin polymerization was from Sigma.

EXAMPLE 7

Immunocytochemistry

After four days in culture, cells were washed twice with warm MT-PBS and fixed with a 4% v/v paraformaldehyde for 10 mins. In some cases, 100 μM BrdU was added to label proliferating cells 12 hours before fixation and detection with monoclonal antibody to BrdU and FITC-labelled rabbit anti-mouse immunoglobulin. For immunoperoxidase staining, endogenous peroxidase was blocked by 3% v/v $H_2O_2$ in methanol for 8 mins and, prior to addition of primary antibody, non-specific protein binding was blocked by incubation for at least 30 mins in MTPBS containing 2% w/v BSA or 2% v/v normal rabbit serum. Controls were performed by replacing primary antibody with pre-immune serum from the appropriate species. Tissue sections or cells were incubated with primary antibodies for 90 min RT, followed by three thorough washes with MTPBS. For immunoperoxidase staining, horseradish peroxidase-conjugated rabbit anti-guinea pig, swine anti-rabbit or rabbit anti-mouse immunoglobulins (Dako) diluted 1:80 were added for 30 mins at RT followed by thorough washes; colour was developed with 3,3'-diaminobenzidine/$H_2O_2$ for 4–8 mins and slides counterstained with haematoxylin.

EXAMPLE 8

Pancreatic Cell Colonies

A pancreatic cell colony was defined as a spherical collection of 20 cells. Colonies were counted under a×10 power objective with an eyepiece graticule.

EXAMPLE 9

Cell Immunoperoxidase Staining and Quantitation

Fetuses at 15.5 and 18.5 dpc from homozygous (−/−) or heterozygous (+/−) $α_6$ integrin gene targeted (Georges-Labouesse et al., 1996) or wild type mice were fixed overnight in Bouin[]s solution. After standard dehydration processing, fetuses were embedded into paraffin and sectioned at 7 μm. Cultured pancreatic cells were washed three times with warm mouse tonicity phosphate buffered saline (MT-PBS) and fixed with 4% paraformaldehyde (PFA) for 10 mins. Endogenous peroxidase was blocked by 3% v/v $H_2O_2$ in methanol for 8 mins. Prior to antibody staining, non-specific protein binding was blocked by incubation for at least 30 mins with MT-PBS containing 2% w/v bovine serum albumin or 2% v/v normal rabbit serum. Controls were performed by replacing first antibody with pre-immune serum from the appropriate species. Cell were incubated with primary antibodies for 90 mins at room temperature, followed by three thorough washes with MT-PBS. Horse-radish peroxidase-conjugated rabbit anti-guinea pig or swine anti-rabbit immunoglobulins (Dako) were added for 30 mins at room temperature followed by thorough washes. Immunoperoxidase was detected with 3,3'-diamninobenzidine/$H_2O_2$ for 4–8 mins, and slides were counterstained with haematoxylin.

Immunoperoxidase positive and negative cells were quantitated in the central strip of each culture chamber (a 90×90 mm square) under a microscope equipped with an eyepiece graticule (Olympus, Japan) at ×40 power and calibrated with a micrometer (Olympus). All data are presented as mean±s.e.m of at least three independent experiments.

EXAMPLE 10

Immunofluorescence Sliding

In some cultures, 100 μM BrdU (Sigma) was included to label proliferating cells; cells were fixed by 4% PFA at days 1, 2, 3 and 4 for insulin and BrdU double immunofluorescence staining. Fetuses were directly snap-frozen in liquid nitrogen, section at 8 μm, the sections air-dried for 40–60 mins and fixed in cold (−20° C.) acetone for 10 mins. Pre-treatment and primary antibody incubations were as described above, followed by incubation with Texas Red-conjugated goat anti-guinea pig immunoglobulins (Vector Laboratories, Burlingame, USA) or fluorescein isothiocyanate (FITC)-conjugated rabbit anti-mouse, -rat or -goat or swine anti-rabbit immunoglobulins (Dako) for 30 mins at room temperature and three thorough washes. Slides were observed and photomicrographed under a Zeis Axiopot fluorescence microscope.

EXAMPLE 11

Statistics

Differences between groups were analyzed by the non-parametric Mann-Whitney U test.

EXAMPLE 12

Effect of BMP

The bioactivity of BMPs (FIG. 3) was both a function of their concentration and composition. For example, 4/7 heterodimers were more active than 4/4 homodomers (Aono et al, 1995).

Figure 4:
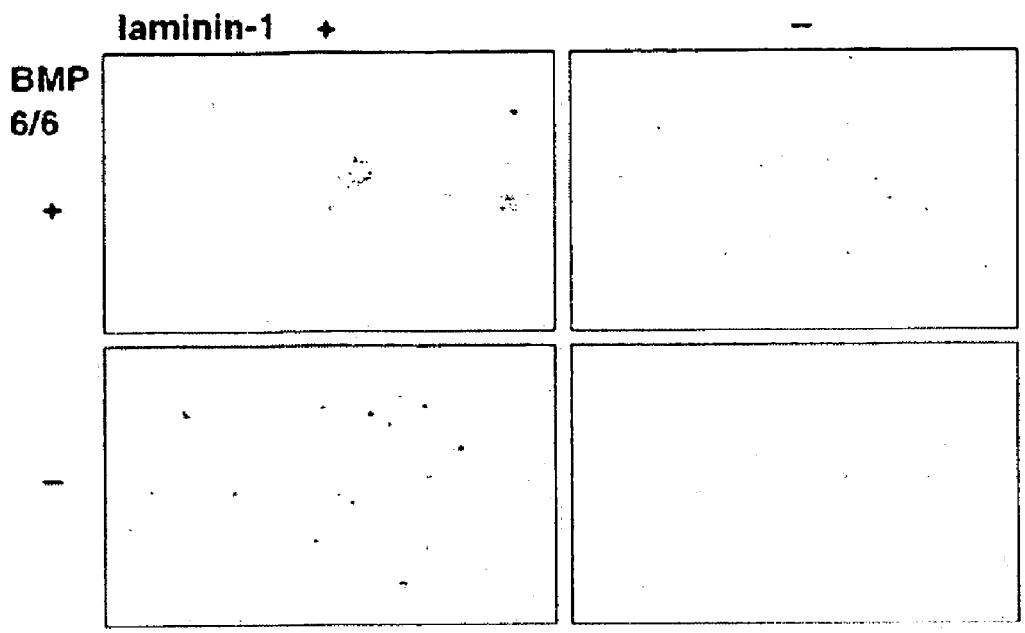
FIG. 4 is a photographic representation of BMP 6/6 (A) and BMP 7/7 (B) stimulated colony formation of 13.5 dpc fetal mouse pancreas cells cultured for four days in the presence of 200 μg/ml laminin-1. Cells were stained with polyclonal guinea pig anti-insulin immunoglobulins and visualized by peroxidase-conjugated rabbit anti-guinea pig immunoglobulins. The bottom left panels display many insulin-positive (brown) cells.
Figure 4:
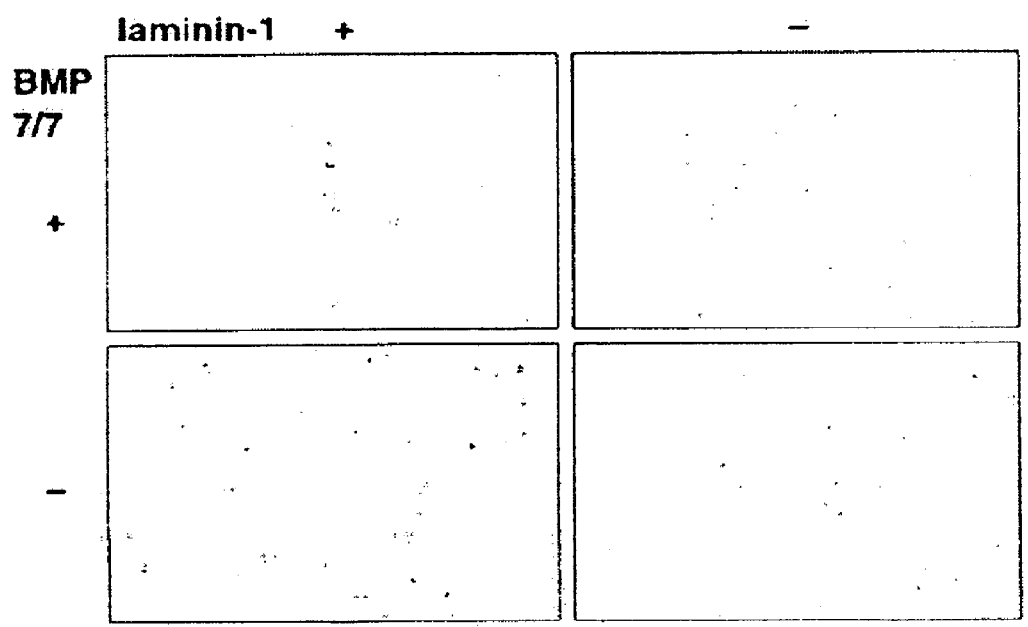
Figure 5:
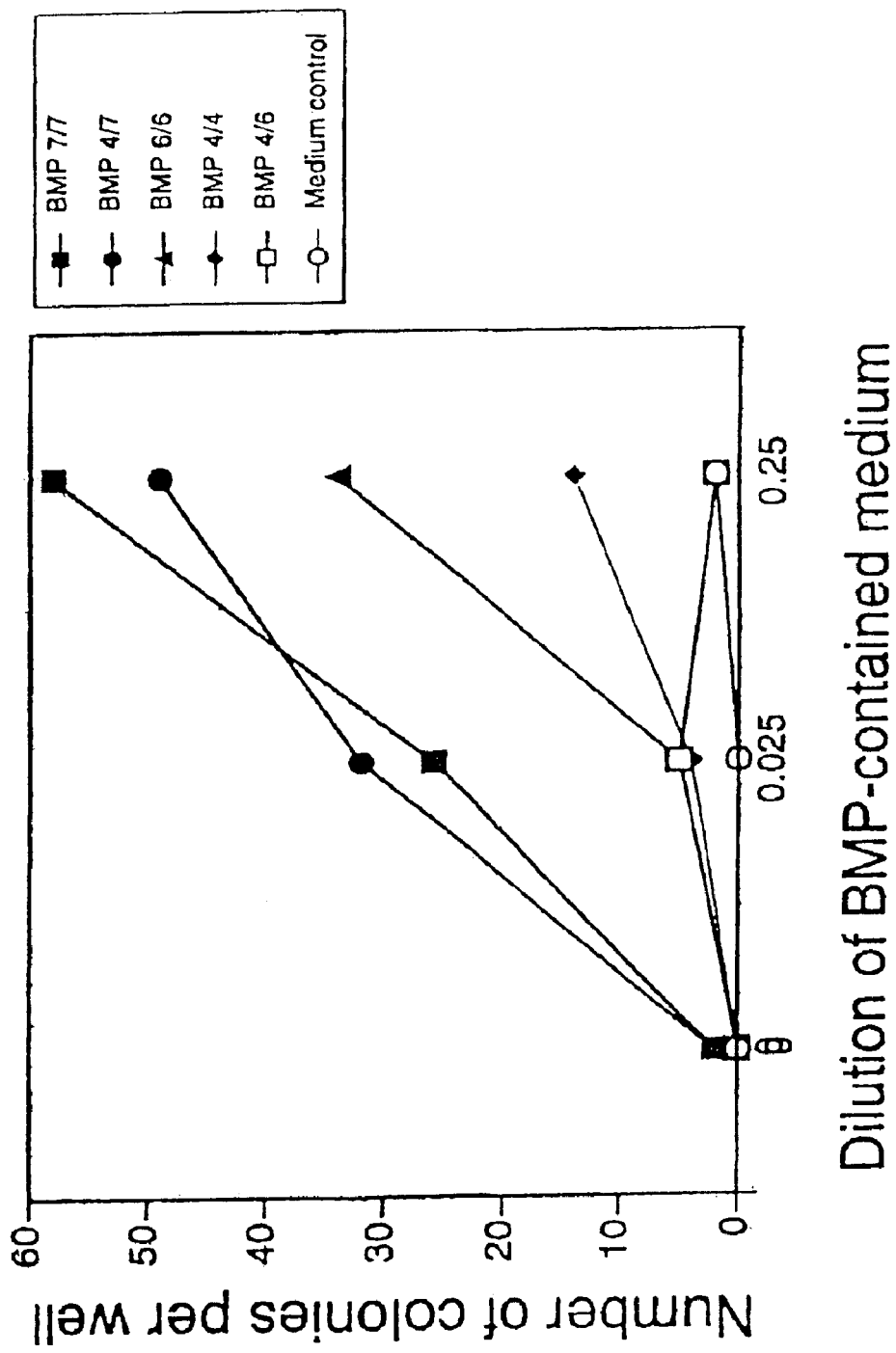
FIG. 5 is a graphical representation of BMP dose-dependence of colony formation of 13.5 dpc fetal mouse pancreas cells cultured for four days.
Figure 6:
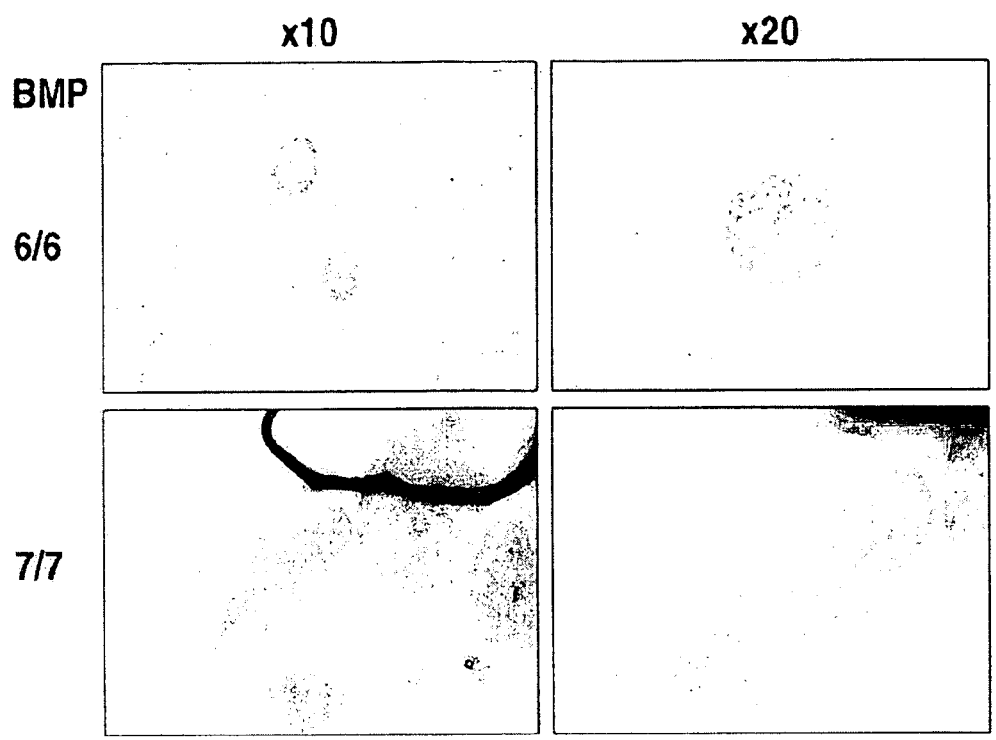
FIG. 6 is a photographic representation of colonies induced by culture of 13.5 dpc fetal pancreas cells for eight days in the presence of BMP 6/6 or BMP 7/7, and laminin-1. Immunoperoxidase staining (brown) for insulin is evident.
Figure 7:
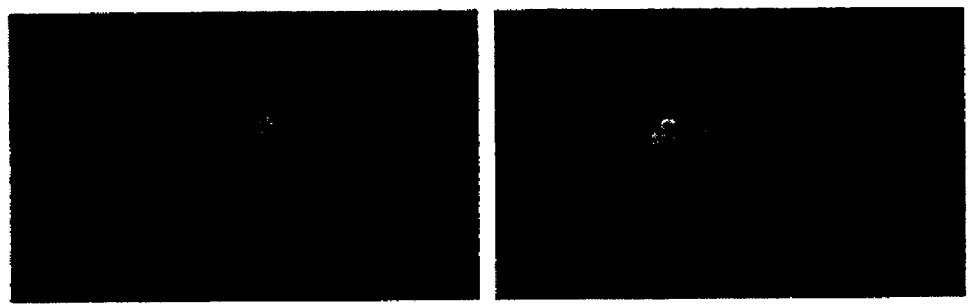
FIG. 7 is a photographic representation of immunofluorescence staining (yellow) for BrdU incorporated into the nuclei of cells in colonies of fetal mouse pancreas cells induced by BMP 7.

In the presence (but not absence) of laminin-1, BMP 6/6, BMP 7/7 and BMP 4/7 stimulated fetal pancreas cells to proliferate and form colonies, which were mainly insulin-negative after four days culture (FIG. 4). BMP 4/4 and BMP 4/6 did not promote colony formation. The effect on colony formation was dose-dependent (FIG. 5). After eight days in culture the colonies had grown much larger and contained central, insulin-positive cells (FIG. 6). BrdU added for 12 hrs in culture labelled cells in the colonies (FIG. 7), providing evidence that the colonies were formed by cell proliferation rather than cell aggregation. A range of candidate growth factors including IGF, TGF and, HGF, EGF, KGF, Activin A, betacellulin, PTrP, gastrin, PYY and TRH were individually unable to promote proliferation or colony formation of these cells.

In summary, BMP 7/7, 4/7 and 6/6 are growth factors for fetal pancreas cells that stimulate formation of colonies containing insulin-positive cells. The inventors propose that the BMPs can be used to generate insulin-secreting bells in the presence of laminin-1 and possibly other differentiation inducers. β cells generated in vivo with these BMPs could be transplanted to treat people with type 1 diabetes, in conduction with appropriate treatment to prevent recurrent autoimmunity and immune-mediated rejection. These BMPs could also be delivered in vivo to patients with type 1 diabetes to stimulate the proliferation and differentiation of cells and thereby restore insulin secretion in the host pancreas.

EXAMPLE 13

$\alpha_6$ Integrin Blockade Stimulates Cell Development

To investigate the role of $\alpha_6$ integrin in laminin-1 induced β cell differentiation, pancreatic cells were cultured with laminin-1 and rat monoclonal IgG2a antibody GoH3, which specifically blocks laminin-1 binding to $\alpha_6$ integrins. GoH3 caused cells to appear more uniformly spherical rather than flattened with laminin-1 alone and resulted in a dose-dependent increase in the number of both total cells and β cells. The increase in total cell number was due to the increase in β cell number. For example, at 40 μg/ml GoH3, β cell number per well increased from 2265±240 (mean±s.e.m n=3) to 6886±364 and total cell number from 4016±650 to 7188±228. Rat IgG2a control antibody had no effect on cell number. β cell number in the presence of GoH3 alone was similar to that in medium only. Thus, the effect of GoH3 to increase β cell differentiation depended on the presence of laminin-1 and GoH3 did not mimic the effect of laminin-1. The proportion of glucagon-positive cells was no higher in the presence of GoH3 and somatostatin- and PP-positive cells and acinar cells were not detected.

To determine if GoH3 affected cell proliferation, 100 μM BrdU was added with laminin-1 (200 μg/ml), with and without GoH3 and BrdU-positive cells analyzed at days 1–4. In the absence of GoH3, 2.5% of cells were BrdU-positive; in the presence of GoH3, BrdU-positive cells could not be detected.

EXAMPLE 14

Inhibition of PI3K, Actin Polymerization or MEK1 Stimulates Cell Development Specific inhibitors were used to block $\alpha_6$ integrin downstream signalling. To determine if P13K has a role in laminin-1 mediated β cell differentiation, 13.5 dpc fetal mouse pancreas cells were cultured for four days with the P13K inhibitors, Wortmannin or Ly294002, at concentrations (0.1–100 μM) reported to be non-toxic for pancreas cells (Gao et al., 1996). Both Wortmannin and Ly294002 significantly increased total and β cell numbers in a dose-dependent manner. Without laminin-1, the number of β cell was not affected by either agent, indicating that differentiation in the presence of laminin-1 requires inhibition of P13K Blocking formation of F-actin by ecytochalasin D may inhibit the Ras-P13K-MEK1 signalling cascade. Cytochalasin D increased laminin-1 induced β cell differentiation, similar to Wortmannin or Ly294002 consistent with a role for the actin cytoskeleton in cell differentiation. MEK1 is downstream from P13K. Inhibition of MEK1 by PD98059 also increased laminin-1 mediated β cell differentiation. Src family tyrosine kinases are associated with focal adhesion kinase (FAK), which may signal MAP kinase via Ras. However, inhibiting Src kinases by genistein or herbimycin A did not affect laminin-1 mediated β cell differentiation.

EXAMPLE 15

$\alpha_6$Integrin Blockade Stimulates Expression of $\alpha_6$ Integrin and α-DG To examine $\alpha_6$ integrin and α-DG expression under different conditions, cultured cells were studied by indirect immunofluorescence. In the absence of laminin-1, cells positive for $\alpha_6$ integrin or α-DG were not observed after two or four days in culture. In the absence of laminin-1, approximately 10% of cells were positive for both $\alpha_6$ integrin and α-DG at day 2 and four. However, at day 2 in the presence of laminin-1 and GoH3, the proportion of cells positive for both $\alpha_6$ integrin and -DG markedly increased to 60–70%.

EXAMPLE 16

Islet Cell Development in $\alpha_6$ Integrin-deficient Mice

The morphology of the pancreas at 15.5 and 18.5 dpc appeared normal in $\alpha_6$ integrin-deficient mouse fetuses. Immunostaining for glucagon, insulin, somatostatin and pancreatic polypeptide revealed that the distribution and number of islet cells were similar in homozygous (−/−) and heterozygous (+/−) mutants and wild type (+/+) fetuses at 18.5 dpc. At 15.5 dpc, the numbers of α- and β-cells were similar among −/−, −/+ and +/+ fetuses, and PP cells were not observed.

EXAMPLE 17

α-Dystroglycan Blockade Inhibits Cell Development

To investigate the role of α-DG in laminin-1 induced β cell differentiation, 13.5 dpc fetal mouse pancreas cells were cultured with laminin-1 and either the mouse IgM monoclonal antibody (IIH6) which blocks laminin-1 binding to α-DG (Ervasti and Campbell, 1993; Durbeej et al., 1995; Brown et al., 1999) or heparin which also blocks laminin-1 binding to α-DG (Ervasti and Campbell, 1993), IIH6 significantly decreased (p<0.01) the number of both total and β cells whereas mouse IgM control antibody (1–20 μg/ml) had no effect. Heparin at 100 μM also significantly decreased (p<0.05) the number of total and β bells. Moreover, at this concentration, heparin blocked the effect of $\alpha_6$ integrin antibody GoH3 to increase β cell differentiation. These findings indicate that laminin-1 signalling via α-DG promotes islet-cell survival and β cell differentiation but that this effect is inhibited by laminin-1 signalling via $\alpha_6$.

EXAMPLE 18

In vitro Culture of Pancreatic Progenitor Cells

Pancreata were dissected from embryonic day (E)15.5 CBA mouse fetuses and dissociated into single cells as described (Jiang et al., 1999). Briefly, dissected pancreas was digested with trypsin/EDTA for 15 minutes at 37° C. in a shaking water bath. Cells were counted in a haemocytometer and viability determined by trypan blue dye exclusion. Each fetal pancreas yielded 50,000 viable cells (48,509±11, 299, n=14). Dissociated cells were plated in 8 well chamber slides (Nunc, Naperville, USA) at 7.5×104 cells/well in 0.3 ml AIM V medium supplemented with N-2 (1:100, Gibco BRL Life Technologies, Gaithersburg, USA), 500 UI/ml penicillin and 500 μg/ml streptomycin. Laminin-1 (160 μg/ml), purified from murine Engelbreth-Holm-Swarm tumor basement membrane (Becton Dickinson Labware, Bedford, USA), was overlayed on cells in the presence of various growth factors. Cultures were incubated in 10% $CO_2$ 90% air at 37° C., for up to 6 days. Recombinant human BMP 6 and BMP 5, recombinant human TGF-β1 and recombinant activin A were purchased from R&D Systems (Minneapolis, USA). These factors, dissolved at a concentration of 10 ng/µl in mouse tonicity phosphate buffered saline (PBS) containing 0.1% w/v bovine serum albumin (BSA), were added at the start of culture. Phase contrast images of colonies were photographed with Olympus IX70 digitized camera.

EXAMPLE 19

Colony Quantitation

Colony formation was assessed at day 6 of culture. A colony was defined as a cellular sphere $\geq 30$ µm in diameter, which contained more than 20 cells. The number of colonies per well was counted directly under a inverted microscope at ×10. Colony counts were performed using a blind design.

EXAMPLE 20

Immunocytochemistry and Histocytochemistry

After 6 days of culture, pancreas cell colonies were harvested by digestion with dispase (Becton Dickinson Labware). Following inactivation of dispase by addition of 8% w/v BSA, the colonies were fixed in 4% w/v paraformaldehyde (PFA), embedded into 1% low melting point agarose gel and processed for histological sections (5 µm) using standard procedures.

For immunoperoxidase staining, endogenous peroxidase was blocked by 3% $H_2O_2$ in methanol for 8 minutes. Before addition of antibody, non-specific protein binding was blocked by incubation of tissues for at least 30 minutes with PBS containing 2% w/v BSA or 2% normal rabbit serum Negative controls were performed by replacing first antibody with pre-immune serum from the appropriate species. Colony sections were incubated with primary antibodies for 90 minutes at 25° C., followed by three washes with PBS. Horseradish peroxidase conjugated rabbit anti-guinea pig, swine anti-rabbit and rabbit anti-mouse immunoglobulins (Dako, Glostrup, Denmark; 1:80) were added for 30 minutes at 25° C., followed by thorough washes. Immunoperoxidase was detected with 3,3'-diaminobenzidine/$H_2O_2$ for 4–8 minutes and slides counterstained with haematoxylin.

For immunofluorescence staining, fluorescein isothyocyanate-conjugated rabbit anti-mouse immunoglobulins (Dako) were added for 30 minutes at 25° C., followed by three thorough washes.

Guinea pig anti-porcine insulin antiserum (final 1:200), rat monoclonal anti-E-cadherin IgG2a (clone ECCD-2) (1:100) and rabbit antiserum to porcine glucagon (1:100) and to human somatostatin (1:200) were purchased from Dako (Glostrup, Denmark). Fractionated rabbit antiserum to human α-amylase, a marker of acinar cells, was from Sigma Bromodeoxyuridine (BrdU) at 100 µM was added to medium for the last 16 hr of cell culture and mouse monoclonal anti-BrdU IgG1 (Clone BU-33) was purchased from Amersham Pharmacia Biotech (Buckinghamshire, UK).

The periodic acid Schiff (PAS) reaction (Bancroft and Stevens, 1982) was used to stain basement membranes.

EXAMPLE 21

RT-PCR Analysis of mRNA Transcripts

Fetal pancreata were removed under a dissection microscope and snap-frozen on dry-ice. Total RNA was extracted with phenol/guanidine isothiocyanate-based RNAzol B (Cinna/Biotex, Hoston, USA). RNA was treated by DNAse I and then reverse transcribed with Superscript II reverse transcriptase (GibcoBRL) in 1× transcription buffer containing 0.5 µM oligo(dT)16–18 primer (GibcoBRL) and 400 µM dNTPs. Aliquots of the cDNAs were amplified by PCR in 1×PCR buffer (Perkin, Elmer, USA) containing 200 µM dNTPs, 1 µM of each primer pair, 1.5 mM $Mg^{++}$ and 1 U Taq polymerase. The following primers were employed: BMP-2 (5' GTGGAGGAACTTCCAGAGATGAGTG 3' [<400>15]; 5' ATTTATTCTTGCTGTGCTAACGACAC 3' [<400>16], 852 bp), BMP-4 (5' CATCCCAGGGACCAGT-GAGAGCTCTG 3' [<400>17]; 5' TCCGCCCTCCGGACT-GCCTGATCTC 3' [<400>18], 863 bp), BMP-5 (5' GAG-CACAGCAAGGCTTGGGAACATG 3' [<400>19]; 5' GCTGGAGATTATAATACCAGTGAAC 3' [<400>20], 240 bp), BMP-6 (5' GTTCTTCAGACTACAACGGCAGTGAG 3' [<400>21]; 5' GTTAGGAATCCAAGGCAGAACCATG 3' [<400>22], 402 bp), BMP-7 (5' GTGTGGCAGAAAA-CAGCAGCAGTGAC 3' [<400>23]; 5' GACATCGAA-GATTTGGAAAGGTGTG 3' [<400>24], 401 bp), TGFβ-1 (5' ACCAACTATTGCTTCAGCTCCACAG 3' [<400>25]; 5' GCAGGAGCGCACAATCATGTTGGAC 3' [<400>26], 317 bp), activin A (5' CTTGGAGTGCGACGGCAAGGT-CAAC 3' [<400>27]; 5' CATTTTCTCTGGGACCTGGC-GACTC 3' [<400>28], 372 bp) and the "housekeeping" gene β actin (5' GTGGGCCGCCCTAGGCACCA 3' [<400>29], 5' CTCTTTGATGTCACGCACGATTTC 3' [<400>30], 530 bp). PCR reactions were performed for 35 cycles (94° C., 30 seconds; 55° C., 30 seconds; 72° C., 30 seconds) and amplified products separated in 1.5% wv/v agarose gels.

EXAMPLE 23

Statistics

Multi-variable experiments were analyZed by ANOVA and differences between groups by Student t test. Data are presented as mean±s.d. of at least three experiments.

EXAMPLE 24

Effects of Growth Factors on Pancreatic Cells

Figure 8:
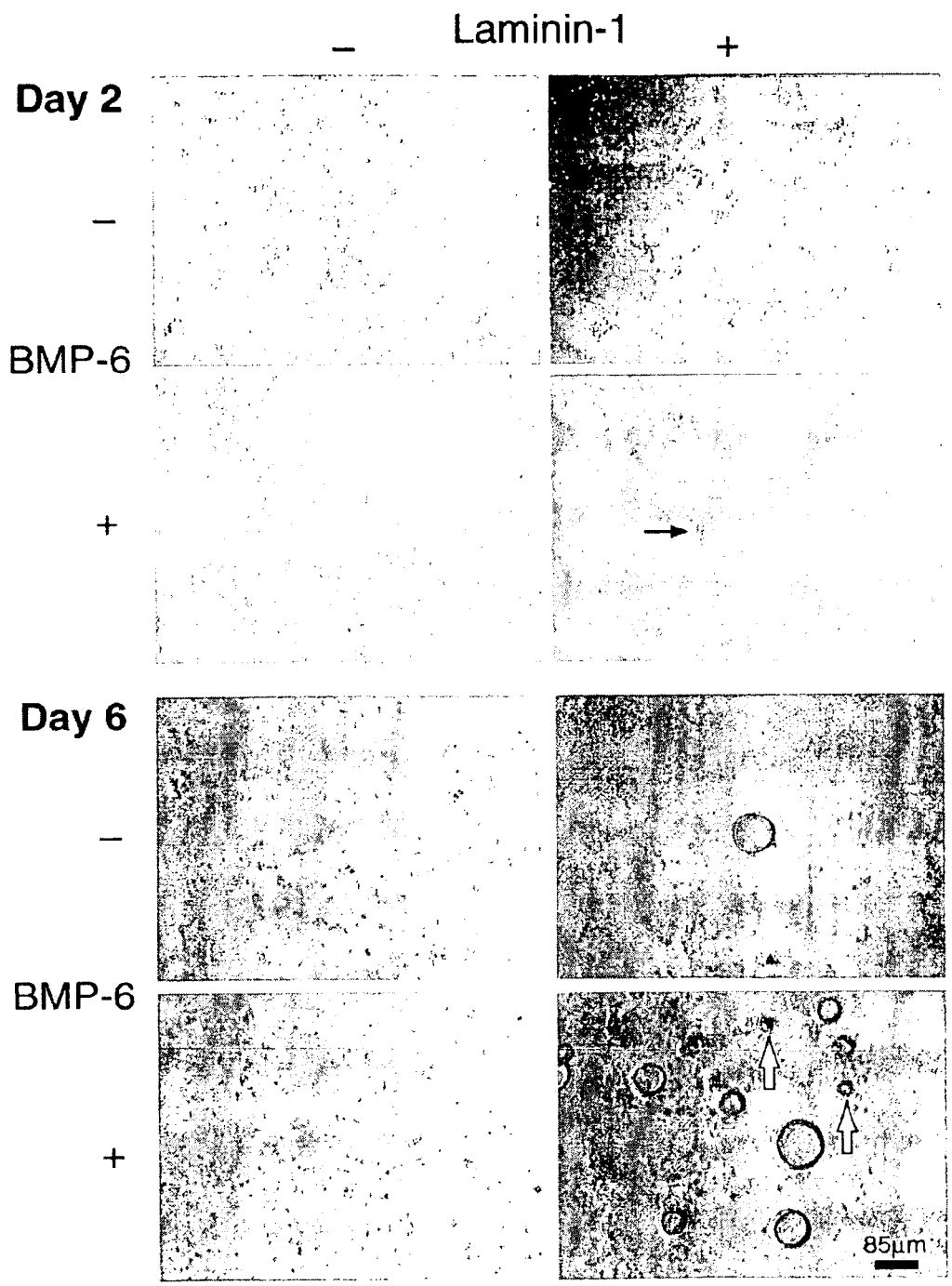
FIG. 8 is a photographic representation showing that BMP 6 (10 ng/ml) synergizes with laminin-1 (160 μg/ml) to promote cystic colony formation by fetal mouse pancreas epithelial cells. Phase contrast images show dissociated cells cultured for 2 or 6 days in the absence or presence of laminin-1 and BMP 6. By day 2, small colonies and some tubular-like structures (closed arrow) were observed in the presence of BMP 6 in cultures containing laminin-1. At day 6, in the presence of both laminin-1 and BMP 6, colonies were increased in numbers and variable size. Colonies ≦30 μm (open arrow) were excluded from the quantitation of colony numbers in FIG. 9 below.

A low cell density culture system was used to demonstrate that fetal pancreas progenitor cells differentiate into insulin-positive β cells in the presence of laminin-1 (Jiang et al., 1999). When this system was modified by replacing HYBIRDOMA medium with AM V medium supplemented with N-2, increasing the cell density to 925 cells/mm$^2$ and decreasing laminin-1 concentration from 200 µg/ml to 160 µg/ml, a low frequency of cystic colonies was observed (FIG. 8). These conditions established a baseline on which the effects of other factors were studied.

In order to ascertain which members of the TGF-β super-family might be relevant to pancreas development, the inventors first performed RT-PCR analysis on mRNAs from E13.5, E15.5 and E17.5 fetal mouse pancreas. BMP 6 and BMP 7 and TGF-β1 were expressed at each age, whereas BMP 5 was detected only at E15.5 and E17.5 and Activin A only at El 7.5; BMP 2 and BMP 4 were not detected at any age.

Figure 9:
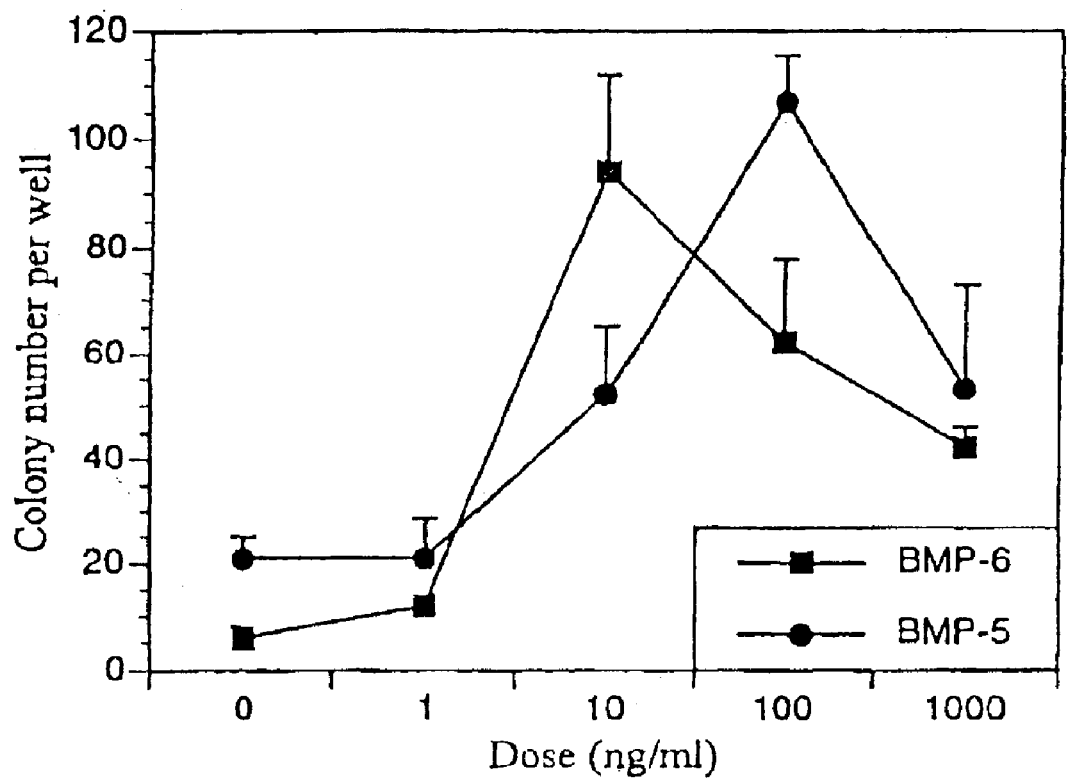
FIG. 9 is a diagrammatic representation showing frequency of colonies (mean+s.d.) as a function of increasing concentrations of BMP 6 or BMP 5 in the presence of 160 μg/ml of laminin-1. Colonies were directly counted under a phase contrast microscope (×10). Colonies ≦30 μm (see FIG. 8) were not counted.

BMP 6 and BMP 5, the BMPs expressed in E15.5 pancreas from which cells were isolated, synergized with laminin-1 to promote formation of cystic colonies (FIG. 8). In the absence of laminin-1, BMP 6 or BMP 5 alone had no effect. Initially, some colonies appeared to be tubular by day 2 although most were cystic (FIG. 8). At day 6, tubular colonies were hardly ever observed. Most of the colonies were 50–60 µm in diameter although a few larger colonies of 100–200 µm were also observed. Maximal stimulation of colony formation occurred at concentrations of 10 and 100 ng/ml BMP 6 and BMP 5, respectively; at higher concentrations, fewer colonies were observed (FIG. 9).

Figure 10A:
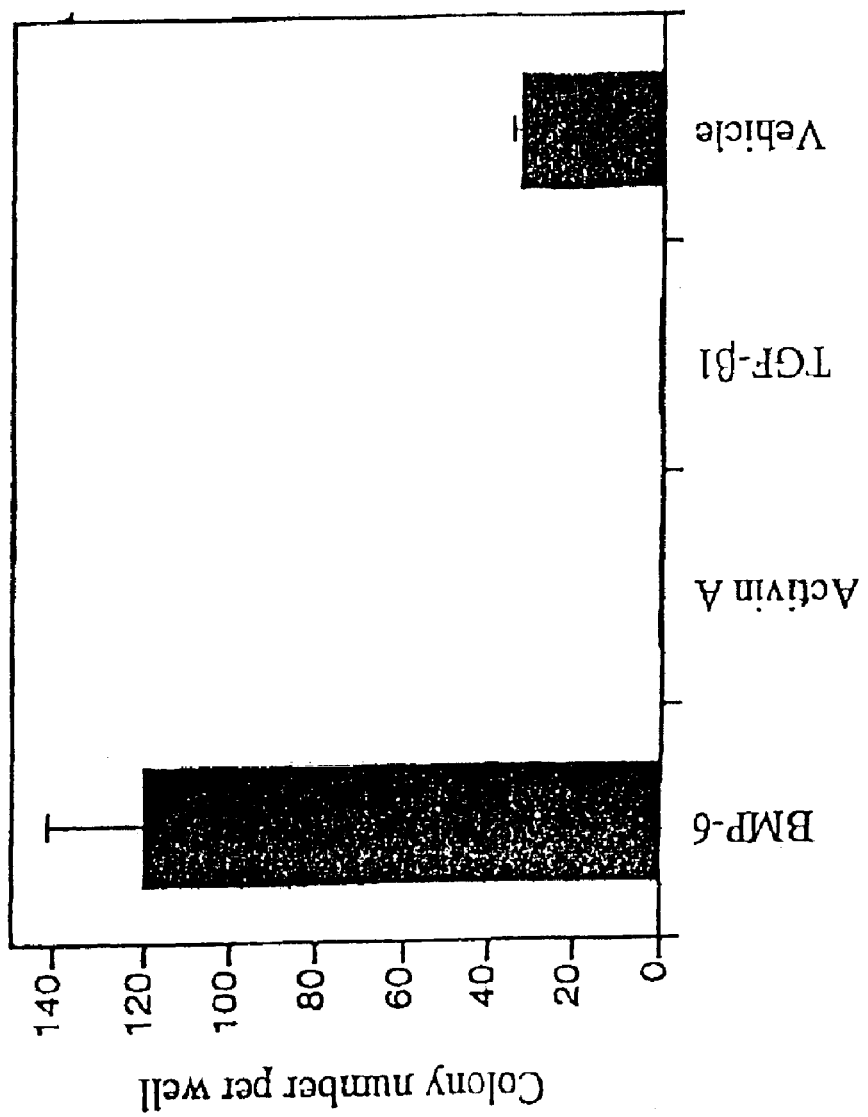
FIG. 10 is a diagrammatic representation showing the effect of TGF-β superfamily members on BMP 6 induced colonies (mean+s.d.) in the presence of 160 μg/ml laminin-1. (A) Effect of BMP 6, TGF-β1 or Activin A (all 100 ng/ml) and laminin-1 alone ("vehicle") on colony numbers. (B) Effect of BMP 5, TGF-β1 or Activin A (all 100 ng/ml) on BMP 6 (10 ng/ml)-induced colony numbers. (C) Dose-dependent inhibition of TGF-β1 (square) and Activin A (circle) of BMP 6 (10 ng/ml)-induced colony numbers.
Figure 10B:
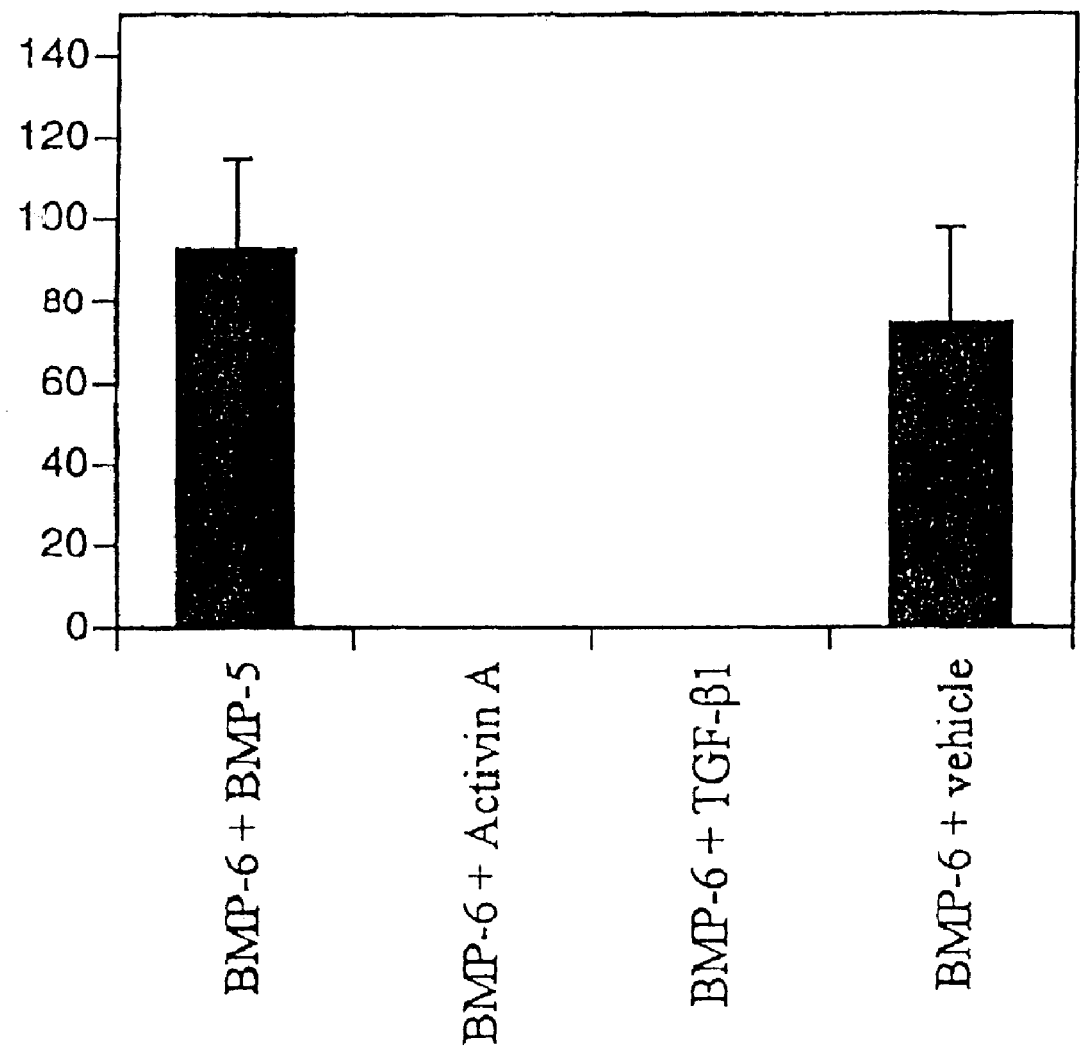
Figure 10C:
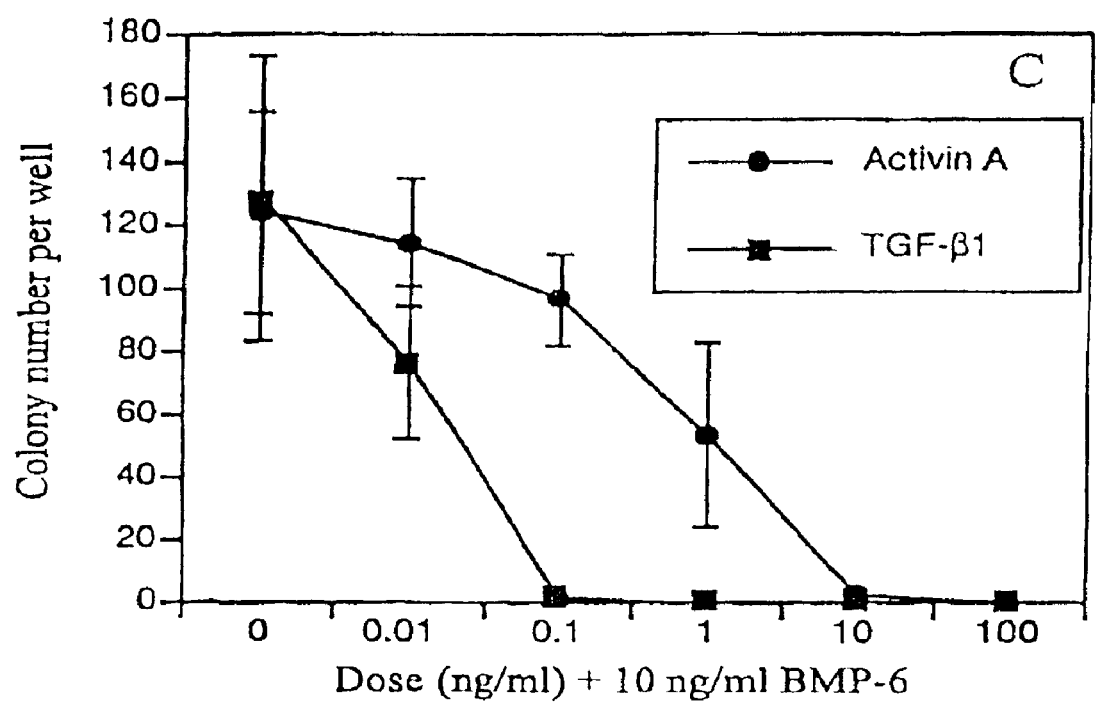

In a number of diverse developmental settings the activity of BMPs is opposed by other members of the TGF-β superfamily, most notably TGF-β1 itself and activins. Both TGF-β1 and Activin A suppressed colony formation to levels below that observed with laminin-1 alone (FIG. 10A). Furthermore, both molecules antagonized BMP 6-induced colony formation (p<0.01) (FIG. 10B). The dose-dependency of inhibition demonstrated that TGF-β1 was 100-fold more potent than Activin A (FIG. 10C). These results indicate that an interplay between TGF-β1, Activin and BMP signaling may be critical for pancreas epithelial cell development.

Figure 11:
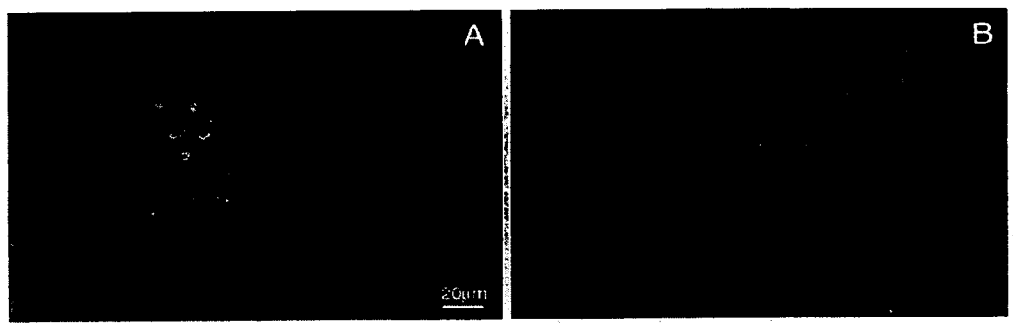
FIG. 11 is a photographic representation showing fluorescence images of fetal pancreas cell colonies generated by culture for 6 days in the presence of laminin-1 and BMP 6, labeled with BrdU and stained with (A) and without (B) mouse monoclonal anti-BrdU antibody.

Having established conditions that favor the formation of cystic colonies, the inventors next examined the nature of the colonies themselves. To determine if the cysts contained proliferating cells, BrdU labeling was performed during the last 16 hrs of culture. Up to 10 BrdU-positive cells per colony were detected (FIG. 11), providing evidence that cellular proliferation contributed to colony formation.

Figure 12:
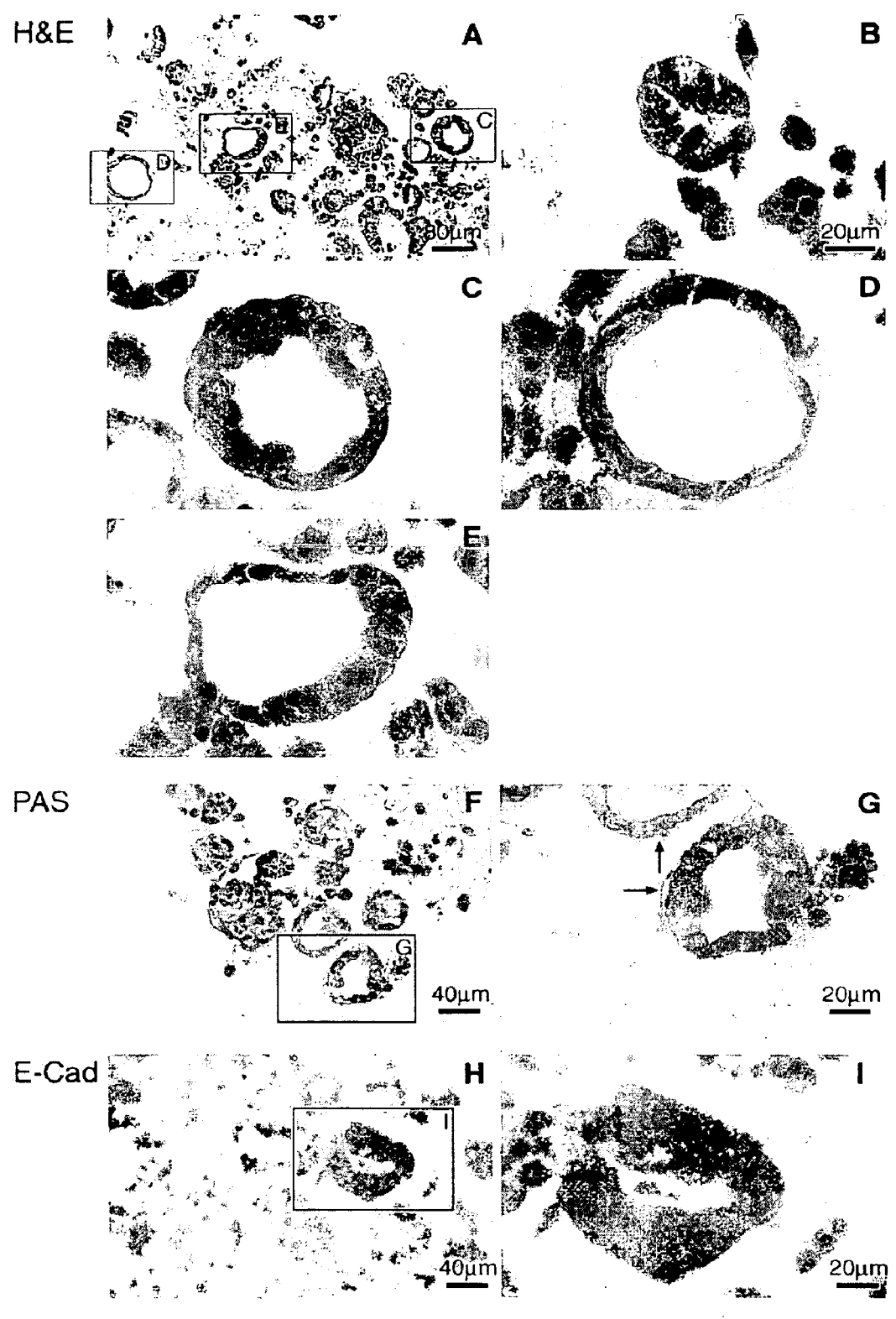
FIG. 12 is a photographic representation showing characterization of colony cells. (A–E) H & E staining showing colonies lined by various types of epithelia (FIG. 12A). Under a higher magnification (oil lens) several types of epithelia are shown: (B) columnar, (C) cuboidal, (D) squamous or (E) a mixture. (F, G) Periodic acid Schiff (PAS) reaction staining of polysaccharides (pink, arrow) in the basement membrane surrounding the colong cells. (H, I) E-cadherin (E-cad), a marker of epithelial cells, detected by rat anti-mouse E-cadherin antibody and visualized by peroxidase-conjugated rabbit anti-rat immunoglobulins (brown).

Histology revealed the colonies to be duct-like in structure, containing various forms of epithelial cells surrounding a central lumen (FIGS. 12A–E). Some colonies were predominantly composed of columnar epithelial cells (FIG. 12B), others of cuboidal cells (FIG. 12C), squamous epithelial cells (FIG. 12D) or a mixture of both columnar and squamous epithelial cells (FIG. 12E). The majority of colonies were surrounded by a PAS-positive basement membrane (FIGS. 12F, 12G). Colony cells stained for E-cadherin, a specific epithelial cell marker involved in cell-cell interactions (FIGS. 12H, 12I) indicating that the colonies most likely originated from ductal progenitor epithelial cells.

Figure 13:
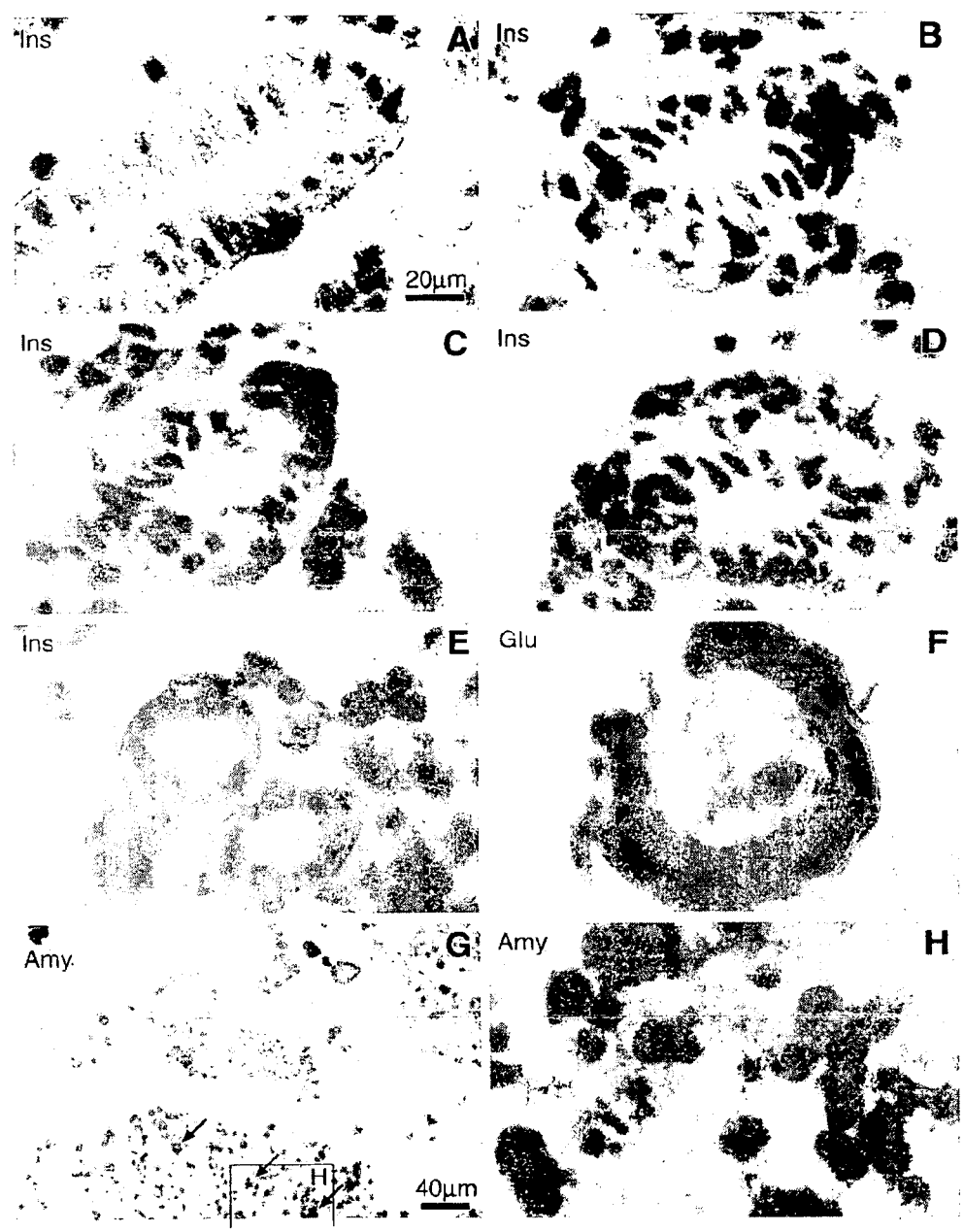
FIG. 13 is a photographic representation showing immunocytochemistry for insulin, glucagon and amylase. Insulin (Ins)-positive cells were stained with guinea pig anti-insulin serum and visualized by peroxidase-conjugated rabbit anti-guinea pit immunoglobulins. Ins-positive cells constituted and in some cases appeared to bud off from colonies (A–E). Glucagon (Glu)-positive cells (F) and amylase (Amy)-positive cells (G, H, arrows) stained with rabbit anti-glucagon and anti-α-amylase antibodies, respectively.

Having identified cells in the colonies as epithelial in nature, the then sought to determine if the colonies contained differentiated cell types or only immature ductal epithelial cells. Insulin-positive cells were always observed in the areas where cystic epithelial cells appeared to be delaminating or segregating from the main body of the colony (FIGS. 13A–E). In addition, some individual insulin-positive cells were also observed between colonies. Glucagon-positive cells were also present in colonies, but were less frequent than insulin-positive cells (FIG. 13F) and somatostatin-positive cells were not detected. Although scattered α-amylase-positive cells were present, they were not associated with the colonies (FIGS. 13G, 13H).

This Example demonstrates an in vitro laminin-1 overlay system which allows single fetal pancreas progenitor cells to proliferate, differentiate and form cystic colonies containing hormone-positive cells. BMP 6 or BMP 5 were shown to synergize with laminin-1 to promote colony formation, whereas TGF-β1, and to a markedly lesser extent Activin A, inhibited colony formation.

Pancreas duct cells and islets have previously been shown to be capable of forming cystic structures when cultured with ECM molecules. Adult human pancreas islet cells, for example, were found to "dedifferentiate" into ductal epithelial cells and form cystic structures when cultured in collagen I gel (Kerr-Conte et al., 1996; Yuan et al., 1996). These cells proliferated in a three dimensional culture, especially in presence of Matrigel (Kerr-Conte et al., 1996). In addition, isolated human pancreas duct cells cultured with a high density Matrigel overlay were also shown to form ductal cysts (Bonner-Weir et al., 2000). However, because Matrigel contains a number of ECM proteins and growth factors (McGuire and Seeds, 1989) it is difficult to identify the contribution made by individual molecules. The inventors circumvented this by using purified laminin-1 to establish a baseline from which to study the effect of specific extrinsic factors on pancreatic cell lineage development. Moreover, the endpoint of this culture system, the formation of cystic epithelial colonies containing differentiated endocrine cells, allowed the inventors to quantitate the effect of alterations in the culture parameters.

The findings herein suggest that TGF-β superfamily members play an important role in pancreas cell lineage development, reflected by the fact that BMP 6 or BMP 5 promote, and TGF-β or Activin A inhibit, colony formation. BMP 6 and BMP 5, as well as BMP 7, constitute the 60A subgroup of BMPs. RT-PCR revealed that all members of 60A subgroup of BMPs, and TGF-β1 and Activin A, were expressed in the developing mouse pancreas. By immunocytochemistry, activin was detected in the E12.5 mouse pancreas epithelium and was restricted to developing islets at E18.5. The ability of fetal pancreas progenitor cells to proliferate, differentiate and form cystic epithelial colonies in vitro also indicates that the instant culture system partially recapitulates development in vivo.

In summary, the inventors demonstrate that specific BMPs promote growth and differentiation of fetal pancreas epithelial cells into cystic colonies containing insulin-positive β cells, an effect antagonized by two other members of the TGF-β superfamily, TGF-β1 and Activin A. Characterization of extracellular factors that promote β-cell development has important implications for the treatment of type 1 diabetes.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Almeida et al. *Cell* 81:1095–1104, 1995
Aono et al. *Biochem. Biophys. Res. Commun.* 210:670–677, 1995
Bancroft, J D and Sevens, A, in *Theory and Practice of Histological Techniques* (Churchill Livingstone, Edinburgh), pp. 188–190
Bonner-Weir et al. *Proc. Natl. Acad. Sci. USA* 97:7999–8004, 2000
Bottinger et al. *EMBO J.* 16: 2621–33, 1997
Brown et al. J. Cell. Sci. 112:209–216, 1999
Bucci et al. *Biol. Reprod.* 34:195–206, 1986
Chan et al. *J. Cell. Biol* 143:2033–2044, 1998
Dudley et al. *Genes Dev.* 9:2795–2807, 1995
Dudley et al. *Proc. Natl. Acad. Sci. USA* 92;7686–7689, 1995
Durbeej et al. *J. Cell Biol.* 130:79–91, 1995
Durbeej et al. Curr. Opin. Cell. Biol. 10:549–601, 1995
Ekblom, P *Curr. Opin. Cell Biol.* 8:700–706, 1996
Ervasti, J. M. and Campbell, K. P. *J. Cell. Biol.* 122:809–823
Falk et al. *J. Cell. Sci.* 109:2801–2810, 1996
Frade et al. *Exp. Cell Res.* 222:140–149, 1996
Gao et al. *Diabetes* 45:854–862, 1996
Georges et al. *Nature Genet.* 13:370–373, 1996

Hebrok et al. *Genes Dev.* 12: 1705–1713, 1998
Hogan, B. L. *Curr. Opin. Genet Dev.* 6: 432–438, 1996
Jiang et al. *Diabetes* 48:722–730, 1999
Jonsson et al. *Nature* 371: 606–609, 1994
Katagiri et al. *J. Cell. Biol* 127:1755–1766, 1994 [erratum appears in *J. Cell. Biol.* 128:713, 1995]
Kerr-Conte et al. *Diabetes* 45: 1108–1114, 1996
Lelievre et al. et al. *Recent Prog. Horm. Res.* 54:417–432, 1996
Luo et al. *Genes Dev.* 9:2808–2820, 1995
Lyons et al. *Mech. Dev.* 50: 71–83, 1995
McGuire, P G and Seeds, N W *J. Cell Biochem.* 40:215–227, 1989
Offield et al. *Develoment* 122: 983–995, 1996
Pall et al. *J. Biol. Chem.* 271:3817–3821, 1996
Powis et al. *Cancer Res.* 54:2419–2423, 1994
Schuger et al. *Dev. Biol.* 179:264–273, 1996
Slack J. M. W. *Development*121:1569–1580, 1995
Sonnenberg et al. *J. Cell. Biol.* 110:2145–2155, 1990
Streuli et al. *J. Cell Biol.* 129:591–603, 1995
Uehara et al. *Mol. Cell. Biol.* 6:2198–2206, 1986
Vlahos et al. *J. Biol. Chem.* 269:5241–5248
Vukicevic et al.*Biochem. Biophys. Res. Commun.* 198: 693–700, 1994
Weaver et al. *Development* 126: 4005–4015, 1999
Winnier et al. *Genes Dev.* 9:2015–2116, 1995
Wozney et al. *Science* 242;1528–1534, 1988
Yamaoka et al. *J. Clin. Invest.* 102: 294–301, 1998
Yuan et al. *Differentiation* 61:67–75, 1996
Zhang and Bradley *Development* 122:2977–2986, 1996

What is claimed is:

1. A method of stimulating growth and differentiation of mammalian pancreatic epithelial cells into three-dimensional cystic-ductular structures containing insulin-secreting cells wherein said pancreatic epithelial cells are isolated from fetal pancreas, said method comprising culturing said pancreatic epithelial cells in the presence of a bone morphogenetic protein (BMP) and at least one of laminin-1 or laminin-1-containing extracellular matrix ECM for a time and under conditions sufficient for colonies to form wherein said colonies comprise three-dimensional cystic-ductular structures containing insulin-secreting cells.

2. The method of claim 1 wherein the BMP molecule is a member of the TGF-β family.

3. The method of claim 2 wherein the BMP molecule is a heterodimer from two or more BMP molecules.

4. The method of claim 1 wherein laminin-1 is provided at a concentration of from about 1 μg/ml to about 1000 μg/ml.

5. A method of stimulating or otherwise facilitating formation of colonies of mammalian pancreatic epithelial cells, wherein said pancreatic epithelial cells are isolated from fetal pancreas and said colonies comprise three-dimensional cystic-ductular structures containing insulin-secreting cells, said method comprising culturing said pancreatic epithelial cells in the presence of a bone morphogenetic protein (BMP) and at least one of laminin-1 or laminin-1-containing extracellular matrix ECM for a time and under conditions sufficient for said colonies to form.

6. The method of claim 5 wherein the BMP molecule is a member of the TGF-β family.

7. The method of claim 6 wherein the BMP molecule is a heterodimer from two or more BMP molecules.

8. The method of claim 5 wherein laminin-1 is provided at a concentration of from about 1 μg/ml to about 1000 μg/ml.

9. A method of stimulating or otherwise facilitating formation of cystic epithelial colonies containing insulin-secreting cells, said method comprising culturing mammalian pancreatic epithelial cells in the presence of a BMP and at least one of laminin-1 or laminin-1-containing extracellular matrix ECM for a time and under conditions sufficient for said colonies to form, wherein said pancreatic epithelial cells are isolated from fetal pancreas, and wherein said colonies comprise existing detected structures containing insulin-secreting cells.

10. The method of claim 9 wherein the BMP molecule is a member of the TGF-β family.

11. The method of claim 10 wherein the BMP molecule is a heterodimer from two or more BMP molecules.

12. The method of claim 9 wherein laminin-1 is provided at a concentration of from about 1 μg/ml to about 1000 μg/ml.

* * * * *